United States Patent
Sabbadini et al.

(10) Patent No.: US 9,274,130 B2
(45) Date of Patent: Mar. 1, 2016

(54) PREVENTION AND TREATMENT OF PAIN USING ANTIBODIES TO LYSOPHOSPHATIDIC ACID

(75) Inventors: Roger A. Sabbadini, Lakeside, CA (US); Rosalia Matteo, Chula Vista, CA (US)

(73) Assignee: Lpath, Inc., San Diego, CA (US)

( * ) Notice: Subject to any disclaimer, the term of this patent is extended or adjusted under 35 U.S.C. 154(b) by 0 days.

(21) Appl. No.: 13/182,644

(22) Filed: Jul. 14, 2011

(65) Prior Publication Data

US 2012/0014944 A1  Jan. 19, 2012

Related U.S. Application Data

(63) Continuation-in-part of application No. 11/755,721, filed on May 30, 2007, now Pat. No. 9,217,749.

(60) Provisional application No. 60/835,569, filed on Aug. 4, 2006, provisional application No. 60/923,644, filed on Apr. 16, 2007.

(51) Int. Cl.
*G01N 33/92* (2006.01)
*C07K 16/18* (2006.01)
*C07K 16/30* (2006.01)
*A61K 39/395* (2006.01)
*A61K 39/00* (2006.01)

(52) U.S. Cl.
CPC ............... *G01N 33/92* (2013.01); *C07K 16/18* (2013.01); *C07K 16/30* (2013.01); *A61K 2039/505* (2013.01); *C07K 2317/24* (2013.01); *C07K 2317/33* (2013.01); *C07K 2317/56* (2013.01); *C07K 2317/76* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | |
|---|---|---|
| 3,773,919 A | 11/1973 | Boswell et al. |
| 4,150,949 A | 4/1979 | Smith |
| 4,275,149 A | 6/1981 | Litman et al. |
| 4,816,397 A | 3/1989 | Boss et al. |
| 4,816,450 A | 3/1989 | Bell et al. |
| 4,816,567 A | 3/1989 | Cabilly et al. |
| 4,937,232 A | 6/1990 | Bell et al. |
| 5,061,626 A | 10/1991 | Baldo et al. |
| 5,079,263 A | 1/1992 | Zeeck et al. |
| 5,110,987 A | 5/1992 | Liotta et al. |
| 5,137,919 A | 8/1992 | Igarashi et al. |
| 5,151,360 A | 9/1992 | Handa et al. |
| 5,225,539 A | 7/1993 | Winter |
| 5,248,824 A | 9/1993 | Igarashi et al. |
| 5,260,288 A | 11/1993 | Igarashi et al. |
| 5,331,014 A | 7/1994 | Kimura et al. |
| 5,369,030 A | 11/1994 | Hannun et al. |
| 5,391,800 A | 2/1995 | Igarashi et al. |
| 5,430,169 A | 7/1995 | Boumendiel et al. |
| 5,444,087 A | 8/1995 | Patel et al. |
| 5,585,476 A | 12/1996 | MacLennan et al. |
| 5,620,689 A | 4/1997 | Allen |
| 5,627,171 A | 5/1997 | Park et al. |
| 5,663,404 A | 9/1997 | Igarashi et al. |
| 5,677,288 A | 10/1997 | Marangos |
| 5,677,337 A | 10/1997 | Wei et al. |
| 5,851,782 A | 12/1998 | Hannun et al. |
| 5,877,167 A | 3/1999 | Igarashi et al. |
| 5,888,793 A | 3/1999 | Hillman |
| 5,919,687 A | 7/1999 | Chatterjee |
| 5,929,039 A | 7/1999 | Woodcock et al. |
| 5,989,803 A | 11/1999 | Tabas et al. |
| 6,051,598 A | 4/2000 | Shayman et al. |
| 6,057,126 A | 5/2000 | Munroe et al. |
| 6,130,067 A | 10/2000 | Tsui |
| 6,140,060 A | 10/2000 | Chun et al. |
| 6,187,562 B1 | 2/2001 | Duckworth et al. |
| 6,210,976 B1 | 4/2001 | Sabbadini |
| 6,248,553 B1 | 6/2001 | Small et al. |
| 6,255,063 B1 | 7/2001 | Small et al. |
| 6,284,798 B1 | 9/2001 | Amtmann et al. |
| 6,300,308 B1 | 10/2001 | Schroit |
| 6,306,911 B1 | 10/2001 | Wachter et al. |
| 6,312,294 B1 | 11/2001 | Lai |
| 6,323,201 B1 | 11/2001 | Carson et al. |
| 6,352,844 B1 | 3/2002 | Maurer et al. |
| 6,423,527 B1 | 7/2002 | Saba et al. |
| 6,500,633 B1 | 12/2002 | Compton et al. |
| 6,534,322 B1 | 3/2003 | Sabbadini |

(Continued)

FOREIGN PATENT DOCUMENTS

| | | | |
|---|---|---|---|
| EP | 0173648 | A2 | 3/1986 |
| EP | 0404097 | A2 | 12/1990 |
| EP | 0125023 | B1 | 6/1991 |
| EP | 0173663 | B1 | 1/1992 |
| EP | 0519596 | A1 | 12/1992 |
| EP | 0120694 | B1 | 7/1993 |
| EP | 0194276 | B1 | 8/1993 |
| EP | 0239400 | B1 | 8/1994 |
| EP | 0736770 | A2 | 10/1996 |
| JP | 09-110722 | A | 4/1987 |

(Continued)

OTHER PUBLICATIONS

Arthritis Research UK (http://www.arthritisresearchuk.org/arthritis-information/drugs/painkillers/medications-for-nerve-pain.aspx Aug. 11, 2015).*

(Continued)

*Primary Examiner* — Peter J Reddig
(74) *Attorney, Agent, or Firm* — Acuity Law Group, P.C.; Daniel M. Chambers

(57) ABSTRACT

Methods for preventing or treating pain are provided. Such methods comprise administering to a subject (e.g., a human subject) an antibody or antibody fragment that binds LPA. The antibody may be a humanized monoclonal antibody.

4 Claims, 15 Drawing Sheets

(56) References Cited

U.S. PATENT DOCUMENTS

| | | | |
|---|---|---|---|
| 6,534,323 | B1 | 3/2003 | Sabbadini |
| 6,610,835 | B1 | 8/2003 | Liotta et al. |
| 6,613,322 | B2 | 9/2003 | Tabas et al. |
| 6,649,362 | B2 | 11/2003 | Gamble et al. |
| 6,783,760 | B1 | 8/2004 | Thorpe et al. |
| 6,806,354 | B2 | 10/2004 | Schroit |
| 6,818,213 | B1 | 11/2004 | Thorpe et al. |
| 6,858,383 | B2 | 2/2005 | Sabbadini |
| 6,881,546 | B2 | 4/2005 | Sabbadini |
| 6,967,022 | B1 | 11/2005 | Livingston et al. |
| 7,060,808 | B1 | 6/2006 | Goldstein et al. |
| 7,169,390 | B2 | 1/2007 | Sabbadini |
| 7,700,792 | B2 | 4/2010 | Hayashi et al. |
| 8,158,124 | B2 | 4/2012 | Sabbadini et al. |
| 2001/0041688 | A1 | 11/2001 | Waeber et al. |
| 2002/0123084 | A1 | 9/2002 | Mills et al. |
| 2002/0150582 | A1 | 10/2002 | Friedrichs et al. |
| 2003/0096022 | A1 | 5/2003 | Sabbadini |
| 2003/0125533 | A1 | 7/2003 | Kossida et al. |
| 2003/0219782 | A1 | 11/2003 | Saba et al. |
| 2005/0226862 | A1 | 10/2005 | Sabbadini |
| 2006/0258616 | A1 | 11/2006 | Wolf et al. |
| 2007/0148168 | A1 | 6/2007 | Sabbadini et al. |
| 2007/0161604 | A1* | 7/2007 | Hayashi et al. ............... 514/100 |
| 2009/0136483 | A1* | 5/2009 | Sabbadini et al. ......... 424/130.1 |
| 2010/0034814 | A1 | 2/2010 | Sabbadini et al. |
| 2011/0064744 | A1 | 3/2011 | Sabbadini et al. |
| 2014/0199293 | A1 | 7/2014 | Sabbadini et al. |

FOREIGN PATENT DOCUMENTS

| | | | |
|---|---|---|---|
| JP | 2000-293181 | A | 10/2000 |
| JP | 2002-243737 | A | 8/2002 |
| WO | 86/01533 | A1 | 3/1986 |
| WO | 93/11161 | A1 | 6/1993 |
| WO | 93/21528 | A1 | 10/1993 |
| WO | 94/07593 | A1 | 4/1994 |
| WO | 97/44019 | A1 | 11/1997 |
| WO | 98/03529 | A1 | 1/1998 |
| WO | 98/28445 | A1 | 7/1998 |
| WO | 98/40349 | A1 | 9/1998 |
| WO | 98/57179 | A1 | 12/1998 |
| WO | 99/07855 | A1 | 2/1999 |
| WO | 99/12890 | A1 | 3/1999 |
| WO | 99/16888 | A2 | 4/1999 |
| WO | 99/33522 | A2 | 7/1999 |
| WO | 99/33972 | A1 | 7/1999 |
| WO | 99/38983 | A1 | 8/1999 |
| WO | 99/41265 | A1 | 8/1999 |
| WO | 99/41266 | A1 | 8/1999 |
| WO | 99/46277 | A1 | 9/1999 |
| WO | 99/61581 | A2 | 12/1999 |
| WO | 00/00593 | A2 | 1/2000 |
| WO | 00/21919 | A1 | 4/2000 |
| WO | 00/40262 | A1 | 7/2000 |
| WO | 00/52173 | A2 | 9/2000 |
| WO | 00/56135 | A2 | 9/2000 |
| WO | 00/58448 | A1 | 10/2000 |
| WO | 00/58491 | A1 | 10/2000 |
| WO | 00/59517 | A1 | 10/2000 |
| WO | 00/70028 | A1 | 11/2000 |
| WO | 00/72833 | A2 | 12/2000 |
| WO | 01/04108 | A1 | 1/2001 |
| WO | 01/04139 | A1 | 1/2001 |
| WO | 01/07418 | A2 | 2/2001 |
| WO | 01/31029 | A2 | 5/2001 |
| WO | 01/38295 | A1 | 5/2001 |
| WO | 01/55410 | A2 | 8/2001 |
| WO | 01/57057 | A1 | 8/2001 |
| WO | 01/60990 | A2 | 8/2001 |
| WO | 01/71045 | A2 | 9/2001 |
| WO | 01/72701 | A1 | 10/2001 |
| WO | 01/80903 | A1 | 11/2001 |
| WO | 01/85953 | A1 | 11/2001 |
| WO | 02/17899 | A2 | 3/2002 |
| WO | 02/051439 | A2 | 7/2002 |
| WO | 03/000701 | A1 | 1/2003 |
| WO | 2004/006847 | A2 | 1/2004 |
| WO | 2005/064332 | A1 | 7/2005 |
| WO | WO 2005/064332 | A1 * | 7/2005 ............. G01N 33/50 |
| WO | 2006/105062 | A2 | 10/2006 |
| WO | 2007/140434 | A2 | 12/2007 |
| WO | 2008/150841 | A1 | 12/2008 |
| WO | 2012/009576 | A2 | 1/2012 |

OTHER PUBLICATIONS

Abe et al., J. Lipid Res., 1995, 611-621, 36(3).
Abe et al., Anal. Biochem., 2000, 344-347, 287(2).
Abe et al., Kidney Int., 2000, 446-454, 57(2).
Ambati, Surv. Ophthalmol., 2003, 257-293, 48(3).
An et al., FEBS Letts., 1997, 279-282, 417(3).
An et al., J. Biol. Chem., 1998, 7906-7910, 273 (14).
An et al., J. Biol. Chem., 2000, 288-296, 275(1).
Ancellin et al., J. Biol. Chem., 2001, 6667-6675, 277(8).
Andrieu-Abadie et al., FASEB J., 1999, 1501-1510, 13(12).
Arenz et al., Angew Chem., 2000, 1498-1500, 112 (German); Angew. Chem. Int. Ed., 2000, 1440-1442, 39(8) (English Equivalent).
Arenz et al., Bioorg. Medicinal Chem., 2001, 2901-2904, 9(11).
Arenz et al., Chem. Biochem., 2001, 141-143, 2(2).
Arenz et al., Eur. J. Org. Chem., 2001, 137-140, 2001(1).
Ariga et al., J. Lip. Res., 1998, 1-16, 39(1).
Bajjalieh et al., Methods Enzymol., 1999, 207-215, 311.
Barbone et al., Methods Enzymol., 1999,168-176, 311.
Bawab et al., J. Biol. Chem., 2000, 21508-21513, 275(28).
Bernardo et al., J. Biol. Chem., 2000, 7641-7647, 275(11).
Betto et al., Biochem. J., 1997, 327-333, 322(1).
Bielawska et al., J. Biol. Chem., 1996, 12646-12654, 271(21).
Bielawska et al., Am. J. Pathol., 1997, 1257-1263, 151(5).
Boudker et al., J. Biol. Chem., 1993, 22150-22155, 268(29).
Brady et al., Proc. Natl. Acad. Sci. USA, 1966, 366-369, 55(2).
Brindley et al., Methods Enzymol., 1999, 233-244, 311.
Brownlee, Current Biol., R535-R538, 2001, 11(13).
Burton et al., Adv. Immunol., 1994, 191-280, 57.
Byers, CA Canc. J., 1999, 353-361, 49(6).
Cain et al., J. Mol. Cell. Cardiol., 1999, 931-947, 31(5).
Caligan et al., Anal. Biochem., 2000, 36-44, 281(1).
Campbell, Lab. Techniques Biochem. Mol. Biol., 1984, 1-33, 13, Ch. 1.
Chan et al., Am. J. Respir. Cell Mol. Biol., 2000, 460-468, 22(4).
Chan et al., Biochemistry, 2000, 4838-4845, 39(16).
Chatterjee, Adv. Lip. Res., 1993, 25-48, 26.
Chatterjee, Arterioscler. Throm. Vasc. Biol., 1998, 1523-1533, 18(10).
Chatterjee, Chem. Phys. Lipids, 1999, 79-96, 102(1).
Chatterjee et al., J. Biol. Chem., 1999, 37407-37412, 274(52).
Chen et al., Anal. Chem. 2000, 2949-2956, 72(13).
Chen et al., Bioorg. Medic. Chem. Lett., 2000, 1691-1693, 10(15).
Chun, Crit. Rev. Neuro., 1999, 151-168, 13(2) (Abstract Only).
Chun et al., Cell Biochem. Biophys., 1999, 213-242, 30(2).
Cordis et al., J. Pharm. Biomed. Anal., 1998, 1189-1193, 16(7).
Cuvlilier et al., Nature, 1996, 800-803, 381(6585).
Dickson et al., Methods and Enzymol., 1999, 3-9, 311.
Edsall et al., Biochemistry, 1998, 12892-12898, 37(37).
Edson et al., Mayo Clin. Proc., 1999, 519-528, 74(5).
Eichler et al., Med. Res. Rev., 1995, 481-496, 15(6) (Abstract Only).
Fensome et al., J. Biol. Chem., 2000, 1128-1136, 275(2).
Fujii et al., J. Biochem (Tokyo), 1998, 1178-1187, 124(6).
Fukushima et al., Proc. Natl. Acad. Sci. USA , 1998, 6151-6156, 95(11).
Furneisen et al., Biochim. Biophys. Acta , 2000, 71-82, 1484(1).
Garcia-Ruiz, Hepatology, 2000, 56-65, 32(1).
Gates et al., Toxicon., 1990, 1303-1315, 28(11).
Gatt et al., J. Neurochem., 1978, 547-550, 31(2).
Gavrilenko et al., Bioorg. Khim., 1993, 133-138, 19(1) (English Abstract Only).
Geeraert et al., Biochem. J., 1997, 125-132, 327(1).
Ghosh et al., J. Biol. Chem., 1987, 12550-12556, 262(26).

(56) References Cited

OTHER PUBLICATIONS

Ghosh et al., Mol. Cell. Biochem., 1998, 161-168, 189(1-2).
Gilmore et al., J. Bacterial., 1989, 744-753, 171(2).
Glickman et al., Mol. Cel. Neurosci., 1999, 141-152, 14(2).
Goetzl et al., Faseb J., 1998, 1589-1598, 12(15).
Goetzl et al., J. Clin. Invest., 2004, 1531-1537, 114(11).
Gonda, et al., Biochem. J., 1999, 67-75, 337(1).
Gonzalez-Zorn et al., Mol. Microbial., 1999, 510-523, 33(3).
Xu et al., J. Biol. Chem., 1998, 16521-16526, 273(26).
Xu et al., Nat. Cell Biol., 2000, 261-267, 2(5).
Yada et al., J. Biol. Chem., 1995, 12677-12684, 270(21).
Yamada et al., Eur. J. Biochem., 1988, 213-220, 175(2).
Yamaji et al., J. Biol. Chem., 1998, 5300-5306, 273(9).
Yamanaka et al., J. Neurochem., 1982, 1753-1764, 38(6).
Yamazaki et al., Biochem. Biophys. Res. Commun., 2000, 583-589, 268(2).
Yatomi et al., Blood, 1995, 193-202, 86(1).
Yatomi et al., J. Biochem., 1997, 969-973, 121(5).
Yatomi et al., J. Biol. Chem., 1997, 5291-5297, 272(8).
Yellon et al., Cardiovasc. Res., 1992, 983-987, 26(10).
Yoshimura et al., J. Neurochem., 1999, 675-683, 73(2).
Yu et al., J. Mol. Neurosci., 2000, 85-97, 15(2).
Zager et al., Kidney Int., 1997, 942-952, 52(4).
Zechner et al., J. Biol. Chem., 1998, 8232-8239, 273(14).
Zelinski et al., J. Biol. Chem., 1980, 11423-11428, 255(23).
Zhang et al., Gene, 1999, 89-99, 227(1).
Zhang et al., Mol. Genet. Metab., 2000, 301-309, 70(4).
Zhou et al., Biochem. Biophys. Res. Comm., 1998, 502-507, 242(3).
Zweerink et al., J. Biol. Chem., 1992, 25032-25038, 267(35).
Graler et al., Genomics, 1998, 164-169, 53(2).
Granziero et al., Eur. J. Immunol., 1999, 1127-1138, 29(4).
Gunther, Eur. J. Pharma., 2000, 123-126, 406(1).
Hakogi et al., Org. Lett., 2000, 2627-2629, 2(17).
Hanada et al., Biochem. Pharmacol., 2000, 1211-1216, 59(10).
Hannun, Science, 1996, 1855-1859, 274(5294).
Hannun et al., Science, 1989, 500-507, 243(4890).
Hannun et al., Adv. Lipid Res., 1993, 27-41, 25.
Hannun at al., Trends Cell Biol., 2000, 73-80, 10(2).
He et al., Anal. Biochem., 1999, 264-269, 274(2).
Heringdorf et al., Eur. J. Pharmacol., 2001, 145-154, 414(2-3).
Hernandez et al., Circ. Res., 2000, 198-204, 86(2).
Hetland et al., Scand. J. Clin. Lab. Invest., 1982, 57-61, 42(1).
Higuchi et al., J. Immunol., 1996, 297-304, 157(1).
Hinkovska-Glacheva et al., Blood, 1998, 4761-4769, 91(12).
Hise et al., J. Clin. Invest., 1986, 768-773, 77(3).
Hla et al., J. Biol. Chem., 1990, 9308-9313, 265(16).
Hofmann et al., Proc. Natl. Acad. Sci. USA, 2000, 5895-5900, 97(11).
Hofstadler et al., Anal. Chem., 1999, 3436-3440, 71(16).
Holopainen et al., J Biol. Chem., 2000, 16484-16489, 275(22).
Horgan et al., Biochem. Biophys. Res. Comm., 2004, 83-94, 319(1).
Horn et al., J. Antibiot. (Tokyo), 1992, 1692-1696, 45(10).
Hoye et al., Organic Letts., 2000, 1481-1483, 2(10).
Hudson, Curr. Op. Biotechnol., 1999, 395-402, 9(4).
Humpf et al., J. Biol. Chem., 1998, 19060-19064, 273(30).
Huwiler et al., Biochim. Biophys. Acta, 2000, 63-99, 1485(2-3).
Igarashi, J. Biochem., 1997, 1080-1087, 122(6).
Igarashi, Ann. NY Acad. Sci.,1998, 19-31, 845.
Ikezawa et al., Biochim. Biophys. Acta, 1978, 247-256, 528(2).
Im et al., J. Biol. Chem., 2000, 14281-14286, 275(19).
Im et al., Mol. Pharmacol., 2000, 753-759, 57(4).
Izuhara et al., Organic Lett., 2001,1653-1656, 3(11).
Jimbo et al., J. Biochem., 2000, 485-491, 127(3).
Johansen et al., Nucl. Acids Res., 1998, 10370, 16(21).
Jonghe et al., Bioorg. Medicinal Chem. Lett., 1999, 3175-3180, 9(21).
Kajstura et al., Lab. Invest., 1996, 86-107, 74(1).
Kanfer et al., J. Biol. Chem., 1966, 1081-1084, 241(5).
Katircioglu et al., J. Cardiovasc. Surg. (Torino), 1999, 45-50, 41(1).
Sucheck et al., Curr. Opin. Drug Disc. Develop., 2001, 462-470, 4(4) (Abstract Only).
Sugita at al, Biochim. Biophys. Acta, 1975, 125-131, 398(1).
Sugiyama et al., Cardiovasc. Res., 2000, 119-125, 46(1).
Sumnicht et al., Arch. Biochem. Biophys., 1982, 628-637, 215(2).
Szulc et al., Tetrahedron Lett., 2000, 7821-7824, 41(41).
Tamamura et al., Jpn. J. Exp. Med., 1971, 31-38, 41(1).
Tamura et al., J. Biochem. (Tokyo), 1992, 488-491, 112(4).
Tanaka et al., J. Am. Chem. Soc., 1997, 7871-7872, 199(33).
Tani et al., J. Biol. Chem., 2000, 3462-3468, 275(5).
Tazabekova et al., Bioorg. Khim., 1987, 648-653, 13(5) (English Abstract Only).
Tomita et al.., J. Biochem. (Tokyo), 1990, 811-815, 108(5).
Tomiuk et al., Proc. Natl. Acad. Sci. USA, 1998, 3638-3643, 95(7).
Torley et al., Anal. Biochem., 1994, 461-464, 222(2).
Tosaka et al., Stroke, 2001, 2913-2919, 32(12).
Triola et al., Angew. Chem. Int. Ed., 2001, 1960-1962, 40(10).
Tsunoda et al., J. Biochem. Mol. Toxicol., 1998, 281-289, 12(5).
Uchida et al., J. Antibiot. (Tokyo), 1999, 572-574, 52(6).
Urdal, Dissertation Abstracts Int., 1980, 4062-4063,41(11B) (Abstract Only).
Usta et al., Biochemistry, 2000, 9657-9668, 40(32).
Van Brocklyn et al., J. Biol. Chem., 1999, 4626-4632, 274(8).
Van Veldhoven et al., Adv. Lipid Res., 1993,69-98,26.
Van Veldhoven, Methods Enzymol. 1999,244-254,311.
Van Veldhoven et al., Biochim. Biophys. Acta, 2000, 128-134, 1487(2-3).
Visentin et al., Cancer Cell., 2006, 225-238, 9(3).
Vivekananda et al., Am. J. Physiol. Lung Cell. Mol. Physiol., 2001, L98-L107, 228(1).
Walev et al., Infect. Immun., 1996, 2974-2979, 64(8).
Wang et al., J. Biol. Chem., 2001, 49213-49220, 276(52).
Webster's Dictionary, 1990, 1135.
Winter et al., Annu. Rev. Immunol., 1994, 433-455, 12.
Wright et al., Crit. Rev. Immunol., 1992, 125-168, 12(3-4).
Xia et al., Proc. Natl. Acad. Sci. USA, 1988, 14196-14201, 95(24).
Xia et al., J. Biol. Chem., 1999, 33143-33147, 274(46).
Kay et al., Comb. Chem. High Throughput Screen, 2001 ,535-543, 4(7) (Abstract Only).
Kester, Trends Glycosci. Glycotechnol., 1997, 447-460, 9(50).
Kihara et al., Circ. Res., 1989, 1029-1044, 65(4).
Kimura et al., J. Biol. Chem., 2001, 15208-15215, 276(18).
Kita et al., Biochim. Biophys. Acta, 2000, 111-120, 1485(2-3).
Kohama et al., J. Biol. Chem., 1998, 23722-23728, 273(37).
Kolesnick, J. Clin. Inv., 2002, 3-8, 110(1).
Kolesnick et al., J. Biol. Chem., 1990, 18803-18808, 265(31).
Krown et al., J. Clin. Invest., 1996, 2854-2865, 98(12).
Kubota et al., Japan J. Exp. Med., 1989, 59-64, 59(2).
Kubota et al., Neurol. Res., 1996, 337-341, 18(4).
Lanterman et al., Biochem. J., 1998, 525-531, 332(2).
Lee et al., Circulation, 1988, 1047-1051, 78(4).
Lee et al., Biochem. J., 1998, 457-461, 334(2).
Lee et al., Biochem. Biophys. Res. Commun., 1999, 743-755, 264(3).
Lee et al., J. Bio. Chem., 1999, 14662-14669, 274(21).
Lee et al., Am. J. Physiol. Cell Physiol., 2000, C612-C618, 278(3).
Levade, et al., J. Clin. Chem. Clin. Biochem., 1986, 205-220, 24(4).
Li et al., Genomics, 1999, 223-231, 62(2).
Liliom et al., Biochem. J., 2001, 189-197, 355(1).
Lin et al., FEBS Lett., 1998, 249-253, 423(2).
Linn et al., Biochem. Soc., 2001, 831-835, 29(6).
Lister et al., Biochim. Biophys. Acta, 1995, 25-30, 1256(1).
Little at al, Biotech. Adv., 1994, 539-555, 12(3).
Liu et al., J. Biol. Chem., 1997, 16281-16287, 272(26).
Liu et al., J. Biol. Chem., 1998, 11313-11320, 273(18).
Liu et al., J. Biol. Chem., 1998, 34472-34479, 273(51).
Liu et al., Crit. Rev. Clin. Lab. Sci., 1999, 511-573, 36(6).
Liu et al., J. Biol. Chem., 2000, 19513-19520, 275(26).
Liu et al., Methods Enzymol., 2000, 164-167, 311.
Lochhead at al, Kidney Int., 1998, 373-381, 54(2).
Luberto et al., J. Biol. Chem., 1998, 14550-14559, 273(23).
Luberto at al., Lipids, 1999, S5-S11, 34(1).
Luster et al., J. Biol. Chem., 2006, 29863-29871, 281(40).
Lynch at al., Trends Pharmacol. Sci., 1999, 473-475, 20(12).

(56) References Cited

OTHER PUBLICATIONS

Magnelli et al., Biochem. Biophys. Res. Comm., 1994, 84-90, 204(1).
Mandala et al., J. Antibiot. (Tokyo), 1994, 376-379, 47(3).
Mandala et al., J. Antibiot. (Tokyo), 1995, 349-356, 48(5).
Mandala et al., J. Antibiot. (Tokyo), 1997, 339-343, 50(4).
Mandala et al., J. Biol. Chem., 1997, 32709-32714, 272(51).
Mandala et al., Proc. Natl. Acad. Sci. USA, 1998, 150-155, 95(1).
Mandala et al., Methods Enzymol., 1999, 335-348, 311.
Mandala et al., Proc. Natl. Acad. Sci. USA, 2000, 7859-7864, 97(14).
Mandala et al., Prostaglandins Other Lipid Mediat., 2001, 143-156, 64(1-4).
Mao et al., Proc. Natl. Acad. Sci. USA, 1996, 1993-1996, 93(5).
Mao et al., J. Biol. Chem., 2000, 31369-31378, 275(40).
Mao et al., J. Biol. Chem., 2000, 6876-6884, 275(10).
Mao et al., J. Biol. Chem., 2001, 26577-26588, 276(28).
Marks et al., Methods Enzymol., 1999, 50-59, 311.
Martin et al., J. Bioenerg. Biomember., 2001, 143-153, 33(2).
Meacci et al., FEBS Lett., 1999, 184-188, 457(2).
Meldrum, Am. J. Physiol., 1998, R577-R595, 274(3).
Melendez et al., Gene, 2000, 19-26, 251(1).
Meroni et al., J. Androl., 1999, 619-625, 20(5).
Merrill Jr. et al., Adv. Lipid Res., 1993, 215-234, 26.
Merrill Jr. et al., J. Lipid Res., 1993, 617-622, 26(5).
Michel et al., J. Biol. Chem., 1997, 22432-22437, 272(36).
Milstien et al., Cancer Cell., 2006, 148-150, 9(3).
Mingeot-Leclercq et al., Antimicrob. Agents Chemother., 1999, 727-734, 43(4).
Mingeot-Leclercq et al., Antimicrob. Agents Chemother., 1999, 1003-1012, 43(5).
Mitsutake et al., J. Biol. Chem., 2001, 26249-26259, 276(28).
Miyake, Biochem. Biophys. Res. Commun., 1995, 396-403, 211(2).
Mohan et al., Biochem. Biophys. Acta, 1984, 339-342, 777(2).
Mohler et al., J. Immunol., 1993, 1548-1561, 151(3).
Nakajima et al., Eur. J. Biochem., 2000, 5679-5686, 267(18).
Napoli et al., J. Clin. Bas. Cardiol., 1998, 37-42, 1(1).
Nikolova-Karakashian et al., Methods Enzymol., 1999, 194-201, 311.
Ohta et al., FEBS Lett., 1994, 267-270, 355(3).
Ohta et al., Cancer Res., 1995, 691-697, 55(3).
Okamoto et al., J. Biol. Chem., 1998, 27104-27110, 273(42).
Okamoto et al., Biochem. Biophys. Res. Commun., 1999, 203-208, 260(1).
Okazaki et al., J. Biol. Chem., 1994, 4070-4077, 269(6).
Okino et al., J. Biol. Chem., 1999, 36616-36622, 274(51).
Olivera et al., Nature, 1993, 557-560, 365(6446).
Olivera et al., Methods Enzymol., 1999, 215-223, 311.
Olshefski et al., Int. J. Cancer, 2001, 131-138, 93(1).
Oral et al., J. Biol. Chem., 1997, 4836-4842, 272(8).
Parrill et al., J. Biol. Chem., 2000, 39379-39384, 275(50).
Pitson et al., J. Biol. Chem., 2000, 33945-33950, 275(43).
Presta et al., Canc. Res., 1997, 4593-4599, 57(20).
Queen et al., Proc. Natl. Acad. Sci. USA, 1989, 10029-10033, 86(24).
Raag et al., FASEB J., 1995, 73-80, 9(1).
Rani et al., J. Biol. Chem., 1995, 2859-2867, 270(6).
Riley et al., Toxicol. Appl. Pharmacol., 1993, 105-112, 118(1) (Abstract Only).
Riley et al., Methods Enzymol., 1999, 348-361, 311.
Romiti et al., Mol. Cell. Biochem., 2000, 75-81, 205(1-2).
Runcie at al, Organic Lett., 2001, 3237-3239, 3(21).
Sabbadini et al., Biochem. Biophys. Res. Comm., 1993, 752-758, 193(2).
Sabbadini et al., Circulation, 2000, II699,102(18 Suppl.).
Saito et al., Organic Letts, 2000, 505-506, 2(4).
Sakai et al., Jpn J. Pharmacol., 1978, 223-229, 28(2).
Sato, J. Clin. Invest., 2000, 939-940, 106(8).
Sawada et al., Cell Death Differ., 2000, 761-772, 7(9).
Sawai et al., J. Biol. Chem., 1999, 38131-38139, 274(53).
Sawai et al., J. Biol. Chem., 2000, 39793-39798, 275(50).
Schissel et al., J. Biol. Chem., 1996, 18431-18436, 271(31).
Sergeyev et al., Kosm. Biol. Aviakosm. Med. (Russian), 1981, 71-74, 15(6) (English Translation pp. 104-108).
Shayman et al., Methods Enzymol., 1999, 42-49, 311.
Shayman et al., Methods Enzymol., 1999, 373-387, 311.
Shinghal et al., J. Neurochem., 1993, 2279-2285, 61(6).
Siehler et al., J. Biol. Chem., 2001, 48733-48739, 276(52).
Siess et al., IUBMB Life, 2000, 161-171, 49(3).
Smith et al., Am. Heart J., 1982, 716-723, 103(4, Pt. 2).
Smith et al., Toxicol. Sci., 2000, 240-249, 56(1).
Spence, Sphingomyelinases, Adv. Lipid Res., 1993, 3-23, 26.
Spence et al., J. Biol. Chem., 1989, 5358-5363, 264(10).
Spiegel et al., FASEB J., 1996, 1388-1397, 10(12).
Spiegel et al., Biochemistry (Mosc)., 1998, 69-73, 63(1).
Spiegel et al., Biochim. Biophys. Acta, 2000, 107-116, 1484(2-3).
Sutphen, Cancer Epidemiol. Biomarkers Prev., 2004, 1185-1191, 13(7).
Svetlov et al., Biochim. Biophys. Acta, 2002, 251-256, 1582(1-3).
Thoreson et al., Invest. Opthalamol. Vis. Sci., 2002, 2450-2461, 43(7).
Tigyi et al., J. Biol. Chem., 1992, 21360-21367, 267(30).
Tomii et al., Jpn J. Med. Sci. Biol., 1991, 75-80, 44(2).
Ueda, Pharmacol. Ther., 2006, 57-77, 109(1-2).
Umeda et al., J. Mol. Biol., 1989, 601-614, 208(4).
Van Leeuwen et al., Biochem. Soc. Trans., 2003, 1209-1212, 31(6).
Vaswani et al., Ann. Allergy Asthma Immunol., 1998, 105-119, 81(2).
Vemuri et al., Lepr. Rev., 1996, 95-103, 67(2).
Vielhaber et al., Glycobiology, 2001, 451-457, 11(6).
Weiner et al., J. Neurosci., 2001, 7069-7078, 21(18).
Wu, Methods, 2005, 1-2, 36(1).
Wu et al., Endocrinology, 2005, 3387-3400, 146(8).
Xiao et al., Anal. Biochem., 2001, 302-313, 29(2).
Xu et al., Cytokine, 1997, 1028-1033, 9(12).
Xu et al., JAMA, 1998, 719-723, 280(8).
Yadav et al., Tetrahedron Lett., 2003, 2983-2985, 44(14).
Yuan et al. Nat. Cell Biol., 2003, 38-45, 5(1).
Zapata et al., Protein Eng., 1995, 1057-1062, 8(10).
Zwaal et al., Blood, 1997, 1121-1132, 89(4).
Qian, Dissertation U. of Utah, 2004, 1-131.
Xu et al., Clin. Cancer Res., 1995, 1223-1232, 1(10).
Adzick et al., Ann. Surg., 1994, 10-18, 220(1).
Anliker et al., J. Biol. Chem., 2001, 20555-20558, 279(20).
Arruda et al., Brain Res., 2000, 216-225, 879(1-2).
Baker et al., Anal. Biochem., 2001, 287-295, 292(2).
Banerji et al., Biochem. Cell Biol., 1990, 96-101, 68(1).
Baranauskas et al., Prog. Neurobiol., 1998, 349-365, 54(3).
Baudhuin et al., FASEB J., 2004, 341-343, 18(2).
Berge et al., J. Pharm. Sci., 1977, 1-19, 66(1).
Brazma et al., FEBS Lett., 2000, 17-24, 480(1).
Brindley, J. Cell. Biochem., 2004, 900-912, 92(5).
Calcutt et al., Anesthesiology, 2000, 1271-1278, 93(5).
Carmeliet, Nature, 2005, 932-936, 438(7070).
Celts et al., FEBS Lett., 2000, 2-16, 480(1).
Chau et al., 221st ACS Natl. Mtg., San Diego, CA, USA, 2001, Am. Chem. Soc. (Abstract Only).
Chen et al., Lipid Mediat., 2005, 65-76, 77(1-4).
Chintalacharuvu et al., Methods, 1995, 73-82, 8.
Chothia et al., J. Mol. Biol., 1985, 651-663, 186(3).
Chothia et al., J. Mol. Biol., 1987, 901-917, 196(4).
Chun et al., Curr. Pharm. Des., 2006, 161-171, 12(2).
Clackson et al., Nature, 1991, 624-628, 352(6336).
Coderre et al., J. Neurosci, 1992, 3665-3670, 12(9).
Coyle et al., Chem. Mater., 1989, 606-611, 1(6).
Desgeorges et al., J. Rheumatol., 1997, 1510-1516, 24(8).
Deutschman et al., Am. Heart J., 2003, 62-68, 146(1).
Diaz et al., Bioconjug. Chem., 1998, 250-254, 9(2).
Dubner et al., Trends Neurosci., 1992, 96-103, 15(3).
Fabianowski et al., Langmuir, 1989, 35-41, 5(1).
Fang et al., Biochim. Biophys. Acta, 2002, 257-264, 1582(1-3).
Flatters et al., Pain, 2006, 245-257, 122(3).
French et al., Cancer Res., 2003, 5962-5969, 63(18).
Fujita et al., Neurochem. Int. 2007, 351-355, 50(2).
Fujiwara et al., J. Biol. Chem., 2005, 35038-35050, 280(41).

(56) References Cited

OTHER PUBLICATIONS

Fukushima et al., Dev Biol., 2000, 6-18, 228(1).
Fukushima et al., Neurochem. Int., 2007, 302-307, 50(2).
Gardell et al., Trends Mol. Med., 2006, 65-75, 12(2).
George et al., Pain, 2000, 267-275, 88(3).
Goetzl et al., Adv. Exp. Med. Biol., 1999, 259-264, 469.
Goetzl et al., Scientific World J., 2002, 324-338, 2.
Hargreaves et al., Pain, 1988, 77-88, 32(1).
Holliger et al., Proc. Natl. Acad. Sci. USA, 1993, 6444-6448, 90(14).
Huang et al., Cancer Res., 2005, 4408-4416, 65(10).
Igarashi et al., Proc. Natl. Acad. Sci. USA, 2003, 10664-10669, 100(19).
Inoue et al., Nat. Med., 2004, 712-718, 10(7).
Inoue et al., J. Neurochem., 2008, 1556-1565, 107(6).
Jalink et al., Cell Growth Differ., 1993, 247-255, 4(4).
Jin et al., Exp. Neurol., 2008, 229-237, 210(1).
Jolivalt et al., Pain, 2006, 14-21, 121(1-2).
Jones et al., Nature, 1986, 522-525, 321(6069).
Jozwiak et al., Eur. J. Cancer Clin. Oncol., 1982, 617-621, 18(7).
Kabat, Pharmacol. Rev., 1982, 23-38, 34(1).
Khachigan, Circ. Res., 2006, 186-191, 98(2).
Kingsbury et al., Nat. Neurosci., 2003, 1292-1299, 6(12).
Kohler et al., Nature, 1975, 495-497, 256(5517).
Kotani et al., New Engl. J. Med., 2000, 1514-1519, 343(21).
Krishnamurthy et al., J. Lipid Res., 2007, 968-975, 48(4).
Lagerqvist et al., Br. Heart J., 1992, 282-285, 68(9).
Lam et al., J. Pharm. Sci., 1997, 1250-1255, 86(11).
Larson et al., Cytometry, 2000, 203-208, 41(3).
Lebrun-Julien et al., Invest. Opthalmol. Vis. Sci., 2005, 46(5), E-Abstract 1319.
Lee et al., Cancer Res., 2006, 2740-2748, 66(5).
Leung et al., J. Neuroinflamm., 2010, 27, 7(1).
Ma et al., J. Pharmacol. Exp. Ther., 2010, 540-546, 333(2).
Maceyka et al., Biochim. Biophys. Acta, 2002, 192-201, 1585(2-3).
Maneta-Peyret et al., J. Immunol. Methods, 1988, 123-127, 108(1-2).
Maneta-Peyret et al., J. Immunol. Methods, 1989, 155-159, 122(2).
Marks et al., J. Mol. Biol., 1991, 581-597, 222(3).
Matsumoto et al., Rheumatol. Int., 2006, 1096-1100, 26(12).
Matteo et al., Proc. Ann. Meeting Am. Assoc. Canc. Res., 2007, 971, 48.
Millan, Prog. Neurobiol., 1999, 1-164, 57(1).
Mills, DTIC [online], 2006, 1-17, 125-138.
Mills et al., Nat. Rev. Cancer, 2003, 582-591, 3(8).
Moolenaar, Exp. Cell Res., 1999, 230-238, 253(1).
Moolenaar et al., BioEssays, 2004, 870-881, 26(8).
Morrison et al., Proc. Natl. Acad. Sci. USA, 1984, 6851-6855, 81(21).
Moulin, Pain Res. Manag., 2006, 30A-36A, 11(Suppl. A).
Mueller et al., Nat. Rev. Drug Discov., 2005, 387-398, 4(5).
Murphy et al. (Ed.), Janeway's Immunobiology, Fifth Edition, 2001, Garland Publishing, London, UK (Electronic Table of Contents Only).
Myers et al., Drug Disc. Today, (2006), 8-20, 11(1-2).
Nakajima et al., Biophysical J., 2000, 319A,78(1, Pt. 2).
Nolli et al., Ann. 1st Super Sanita, 1991, 149-154, 27(1).
Ohlsson et al., Tetrahedron, 2000, 9975-9984, 56(51).
Osol et al. (Ed.), Remington's Pharmaceutical Sciences 19th edition, 1990 (Table of Contents).
Pitson et al., Biochem J., 2000, 429-441, 350(2).
Polomano et al., Pain, 2001, 293-304, 94(3).
Presta, Curr. Opin. Struct. Biol., 1992, 593-596, 2(4).
Pyne et al., Biochem. J., 2000, 385-402, 349(Pt. 2).
Ramakers et al., Exp. Cell Res., 1998, 252-262, 245(2).
Ramer et al. J. Neurosci., 2004, 10796-10805, 24(48).
Ran et al., Clin. Cancer Res., 2005, 1551-1562, 11(4).
Riechmann et al., Nature, 1988, 323-329, 332(6162).
Scherer et al., Cardiovasc. Res., 2006, 79-87, 70(1).
Schousboe, Biochim. Biophys. Acta, 1979, 396-408, 579(2).
Seltzer et al., Pain, 1990, 205-218, 43(2).
Shen et al., Gynecol. Oncol., 2001, 25-30, 83(1).
Simard et al., Nat. Med., 2006, 433-440, 12(4).
Simon et al., J. Biol. Chem., 2005, 14656-14662, 280(15).
Spiegel et al., Leukemia, 2002, 1596-1602, 16(9).
Spiegel et al., Nat. Rev. Mol. Cell Biol., 2003, 397-407, 4(5).
Suomalainen et al., Am. J. Pathol., 2005, 773-781, 166(3).
Sutcliffe et al., Proc. Natl. Acad. Sci. USA, 2000, 1976-1981, 97(5).
He et al., Phospholipid-Stabalized Au-Nanoparticles, Biomacromolecules, 2005, 1224-1225, 6(3).
Matteo et al., Anti-tumor effects of several monoclonal antibodies that bind all the principal isoforms of lysophosphatidic acid, 2007, 2007 AACR Annual Meeting, 1 (Abstract).

\* cited by examiner

PREVENTION AND TREATMENT OF PAIN USING ANTIBODIES TO LYSOPHOSPHATIDIC ACID

This application claims the benefit of and priority to U.S. patent application Ser. No. 11/755,721, filed 30 May 2007, issued as U.S. Pat. No. 9,217,749, of which this application is a continuation-in-part, as well as to U.S. provisional patent application Ser. No. 60/835,569, filed 4 Aug. 2006, and U.S. provisional patent application Ser. No. 60/923,644, filed 16 Apr. 2007, to which the Ser. No. 11/755,721 application claims priority. Each of the foregoing applications is commonly owned with the instant application, and each is hereby incorporated by reference in its entirety for any and all purposes.

TECHNICAL FIELD

The present invention relates to agents that bind lysophosphatidic acid (LPA) and its variants, particularly to monoclonal antibodies, antibody fragments, and antibody derivatives specifically reactive to LPA under physiological conditions. Such agents can be used in the treatment and/or prevention of various diseases or disorders through the delivery of pharmaceutical compositions that contain such agents.

LPA is a bioactive lipid mediating multiple cellular responses including proliferation, differentiation, angiogenesis, motility, and protection from apoptosis in a variety of cell types.

LPA is involved in the establishment and progression of cancer by providing a pro-growth tumor microenvironment and promoting angiogenesis. In addition, LPA has been implicated in fibrosis, ocular diseases such as macular degeneration, and pain-related disorders. Therefore, an antibody-based approach to the neutralization of LPA offers the potential to increase the arsenal of current therapies for these indications.

The assignee has invented a family of high-affinity, specific monoclonal antibodies to LPA, one of which is known as Lpathomab. The efficacy of Lpathomab in various animal models of cancer, fibrosis, and ocular disorders highlights the utility of this class of anti-LPA antibodies (and molecules derived therefrom), for example, in the treatment of malignancies, angiogenesis, and fibrosis-related disorders.

BACKGROUND OF THE INVENTION

1. Introduction

The following description includes information that may be useful in understanding the present invention. It is not an admission that any of the information provided herein, or any publication specifically or implicitly referenced herein, is prior art, or even particularly relevant, to the presently claimed invention.

2. Background

A. Bioactive Signaling Lipids

Certain lipids and their derivatives are now recognized as important targets for medical research, not as just simple structural elements in cell membranes or as a source of energy for—oxidation, glycolysis or other metabolic processes. In particular, certain lipids function as signaling mediators important in animal and human disease. Although most of the lipids of the plasma membrane play an exclusively structural role, a small proportion of them are involved in relaying extracellular stimuli into cells. These lipids are referred to as "bioactive lipids" or, alternatively, "bioactive signaling lipids." "Lipid signaling" refers to any of a number of cellular signal transduction pathways that use cell membrane lipids as second messengers, as well as referring to direct interaction of a lipid signaling molecule with its own specific receptor. Lipid signaling pathways are activated by a variety of extracellular stimuli, ranging from growth factors to inflammatory cytokines, and regulate cell fate decisions such as apoptosis, differentiation and proliferation. Research into bioactive lipid signaling is an area of intense scientific investigation as more and more bioactive lipids are identified and their actions characterized.

Examples of bioactive lipids include the eicosanoids (including the cannabinoids, leukotrienes, prostaglandins, lipoxins, epoxyeicosatrienoic acids, and isoeicosanoids), non-eicosanoid cannabinoid mediators, phospholipids and their derivatives such as phosphatidic acid (PA) and phosphatidylglycerol (PG), platelet activating factor (PAF) and cardiolipins as well as lysophospholipids such as lysophosphatidyl choline (LPC) and various lysophosphatidic acids (LPA). Bioactive signaling lipids also include the sphingolipids such as sphingomyelin, ceramide, ceramide-1-phosphate, sphingosine, sphingosylphosphoryl choline, sphinganine, sphinganine-1-phosphate (dihydro-S1P) and sphingosine-1-phosphate. Sphingolipids and their derivatives represent a group of extracellular and intracellular signaling molecules with pleiotropic effects on important cellular processes. Other examples of bioactive signaling lipids include phosphatidylinositol (PI), phosphatidylethanolamine (PEA), diacylglyceride (DG), sulfatides, gangliosides, and cerebrosides.

1. Lysolipids

Lysophospholipids (LPLs), also known as lysolipids, are low molecular weight (typically less than about 500 dalton) lipids that contain a single hydrocarbon backbone and a polar head group containing a phosphate group. Some lysolipids are bioactive signaling lipids. Two particular examples of medically important bioactive lysolipids are LPA (glycerol backbone) and S1P (sphingoid backbone). The structures of selected LPAs, S1P, and dihydro S1P are presented below.

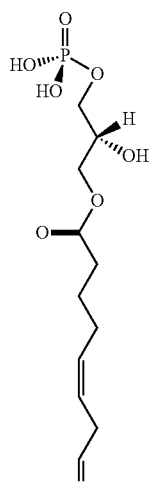

LPA (20:4)

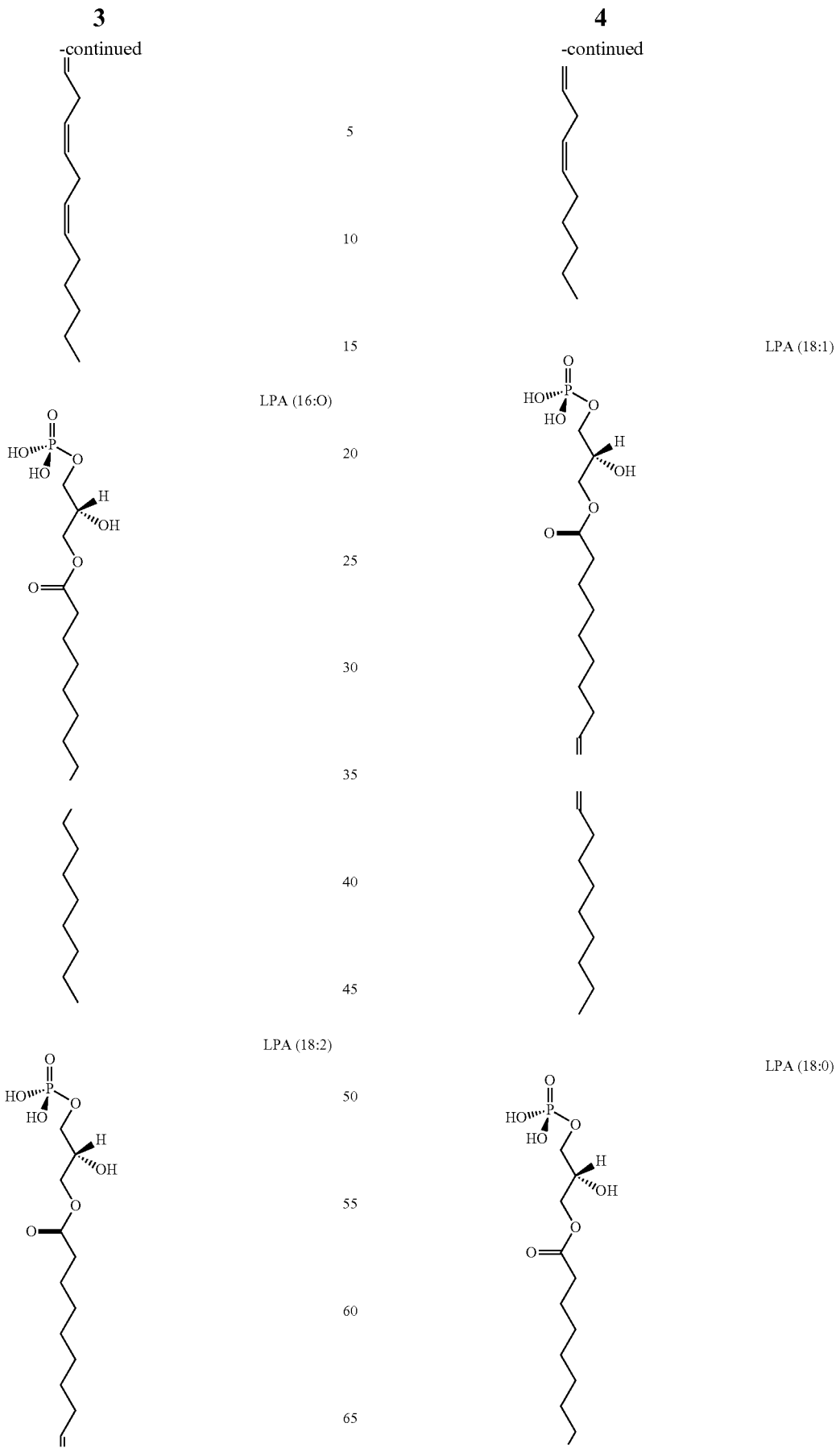
LPA (16:0)
LPA (18:2)
LPA (18:1)
LPA (18:0)

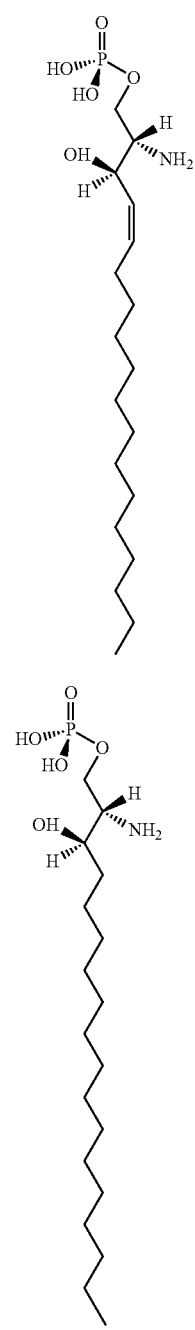

S1P

Dihydo-S1P

The structural backbone of LPA is derived from glycerol-based phospholipids such as phosphatidylcholine (PC) or phosphatidic acid (PA). In the case of lysosphingolipids such as S1P, the fatty acid of the ceramide backbone is missing. The structural backbone of S1P, dihydro S1P (DHS1P), and sphingosylphosphorylcholine (SPC) is based on sphingosine, which is derived from sphingomyelin.

LPA and S1P regulate various cellular signaling pathways by binding to the same class of multiple transmembrane domain G protein-coupled (GPCR) receptors. The S1P receptors are designated as S1P1, S1P2, S1P3, S1P4 and S1P5 (formerly EDG-1, EDG-5/AGR16, EDG-3, EDG-6 and EDG-8) and the LPA receptors designated as LPA1, LPA2, LPA3 (formerly, EDG-2, EDG-4, and EDG-7). A fourth LPA receptor of this family has been identified for LPA (LPA4), and other putative receptors for these lysophospholipids have also been reported.

LPA and S1P have been shown to play a role in the immune response through modulation of immune-related cells such as T- and B-lymphocytes. These lipids promote T-cell migration to sites of immune response and regulate proliferation of T cells as well as secretion of various cytokines. In particular, S1P is thought to control egress of lymphocytes into the peripheral circulation. Thus agents which bind LPA and S1P are believed to be useful in methods for decreasing an undesired, excessive or aberrant immune response, and for treating diseases and conditions, including certain hematological cancers and autoimmune disorders that are associated with an undesired, excessive or aberrant involvement of lymphocytes and or an aberrant immune response.

a. Lysophosphatic Acid (LPA)

Lysophosphatidic acid (mono-acylglycerol-3-phosphate, <500 Dalton) consists of a single hydrocarbon backbone and a polar head group containing a phosphate group. LPA is not a single molecular entity but a collection of endogenous structural variants with fatty acids of varied lengths and degrees of saturation. Thus, when used herein, "LPA" refers to the set of bioactive LPA variants, unless stated otherwise. Biologically relevant variants of LPA include 18:2, 18:1, 18:0, 16:0 and 20:4. LPA species with both saturated fatty acids (16:0 and 18:0) and unsaturated fatty acids (16:1, 18:1, 18:2, and 20:4) have been detected in serum and plasma. The 16:0, 18:1, 18:2 and 20:4 LPA isoforms are the predominant species in blood. Significant levels (>1 µM) of bioactive LPA are detectable in various body fluids, including serum, saliva, follicular fluid and malignant effusions.

The present invention provides among its aspects anti-LPA agents that are useful for treating or preventing hyperproliferative disorders and various other disorders, as described in greater detail below. In particular, certain embodiments of the invention is drawn to antibodies targeted to LPA including but not limited to 18:2, 18:1, 18:0, 16:0, and 20:4 variants of LPA.

LPA has long been known as precursors of phospholipid biosynthesis in both eukaryotic and prokaryotic cells, but LPA has emerged only recently as a signaling molecule that are rapidly produced and released by activated cells, notably platelets, to influence target cells by acting on specific cell-surface receptor. Besides being synthesized and processed to more complex phospholipids in the endoplasmic reticulum, LPA can be generated through the hydrolysis of pre-existing phospholipids following cell activation; for example, the sn-2 position is commonly missing a fatty acid residue due to de-acylation, leaving only the sn-3 hydroxyl esterified to a fatty acid. Moreover, a key enzyme in the production of LPA, autotaxin (lysoPLD/NPP2), may be the product of an oncogene, as many tumor types up-regulate autotoxin. The concentrations of LPA in human plasma and serum have been reported, including determinations made using sensitive and specific LC/MS procedures. For example, in freshly prepared human serum allowed to sit at 25° C. for one hour, LPA concentrations have been estimated to be approximately 1.2 mM, with the LPA analogs 16:0, 18:1, 18:2, and 20:4 being the predominant species. Similarly, in freshly prepared human plasma allowed to sit at 25° C. for one hour, LPA concentrations have been estimated to be approximately 0.7 mM, with 18:1 and 18:2 LPA being the predominant species.

LPA mediates its biological functions predominantly by binding to a class of multiple transmembrane G protein-coupled receptors (GPCR). Five LPA-specific GPCRs, termed LPA1-5, have been identified to date; they show both overlapping and distinct signaling properties and tissue expression. The LPA1-3 receptors belong to the so-called EDG subfamily (EGD2/LPA1, EDG4/LPA2, and EDG7/LPA3) of GPCRs with 50% sequence similarity to each other. Their closest relative is the cannabinoid CB1 receptor, which binds the bioactive lipids 2-arachidonoyl-glycerol (2-AG) and arachidonoyl-ethanolamine. Two newly identified LPA receptors, termed LPA4 (formerly GPR23/p2y9) and LPA5 (formerly GPR92) are more closely related to the P2Y nucleotide receptors. In addition, LPA recognizes the intracellular receptor, PPRgamma.

LPA1 is expressed in a wide range of tissues and organs whereas LPA2 and LPA3 show more restricted expression profile. However, LPA2 and LPA3 expressions were shown to be increased in ovarian and colon cancers and inflammation, suggesting that the main role of LPA2 and LPA3 is in pathophysiological conditions.

The role of these receptors has been in part elucidated by receptor knockout studies in mice. LPA1-deficient mice show partial postnatal lethality due to a suckling defect resulting from impaired olfaction. LPA1-deficient mice are also protected from lung fibrosis in response to bleomycin-induced lung injury. Furthermore, mice lacking the LPA1 receptor gene lose the nerve injury-induced neuropathic pain behaviors and phenomena.

In contrast, mice lacking LPA2 receptors appear to be normal. LPA3 receptor knockout mice have reduced litter size due to delayed blastocyst implantation and altered embryo spacing, and LPA3-deficient uteri show reduced cyclooxygenase-2 (COX-2) expression and prostaglandin synthesis; while exogenous administration of PGE2 into LPA3-deficient female mice has been reported to rescue the implantation defect.

LPAs influence a wide range of biological responses, including induction of cell proliferation, stimulation of cell migration and neurite retraction, gap junction closure, and even slime mold chemotaxis. The body of knowledge about the biology of LPA continues to grow as more and more cellular systems are tested for LPA responsiveness. The major physiological and pathophysiological effects of LPA include, for example:

Wound healing: It is now known that, in addition to stimulating cell growth and proliferation, LPA promote cellular tension and cell-surface fibronectin binding, which are important events in wound repair and regeneration.

Apoptosis: Recently, anti-apoptotic activity has also been ascribed to LPA, and it has recently been reported that peroxisome proliferation receptor gamma is a receptor/target for LPA.

Blood vessel maturation: Autotaxin, a secreted lysophospholipase D responsible for producing LPAs, is essential for blood vessel formation during development. In addition, unsaturated LPAs were identified as major contributors to the induction of vascular smooth muscle cell dedifferentiation.

Edema and vascular permeability: LPA induces plasma exudation and histamine release in mice.

Inflammation: LPA acts as inflammatory mediator in human corneal epithelial cells. LPA participates in corneal wound healing and stimulates the release of ROS in lens. LPA can also re-activate HSV-1 in rabbit cornea.

The bite of the venomous spider, *Loxosceles reclusa* (brown recluse spider), causes necrotic ulcers that can cause serious and long lasting tissue damage, and occasionally death. The pathology of wounds generated from the bite of this spider consists of an intense inflammatory response mediated by AA and prostaglandins. The major component of the *L. reclusa* spider venom is the phospholipase D enzyme often referred to as sphingomyelinase D (SMase D), which hydrolyzes sphingomyelin to produce C1P. It has been found, however, that lysophospholipids with a variety of headgroups are hydrolysed by the *L. reclusa* enzyme to release LPA. It is believed that anti-LPA agents such as those of the invention will be useful in reducing or treating inflammation of various types, including but not limited to inflammation resulting from *L. reclusa* envenomation.

Fibrosis and scar formation: LPA inhibits TGF-mediated stimulation of type I collagen mRNA stability via an ERK-dependent pathway in dermal fibroblasts. Moreover, LPA have some direct fibrogenic effects by stimulating collagen gene expression and proliferation of fibroblasts.

Immune response: LPA, like S1P, has been shown to play a role in the immune response through modulation of immune-related cells. These lipids promote T-cell migration to sites of immune response and regulate proliferation of T cells as well as secretion of various cytokines.

Neurodegeneration: Following events which damage the blood brain barrier, LPA activity is increased within the cerebrospinal fluid and levels of LPA within the CNS are hypothesized to increase up to 10 μM. Normally undetectable, levels of the LPA-producing enzyme autotaxin increase in astrocytes neighbouring a lesion of the adult brain, supporting a role for LPA in CNS injury responses. LPA injections into mouse brain induce astrocyte reactivity at the site of the injury, while in the spinal cord, LPA induces neuropathic pain and demyelination. LPA can stimulate astrocytic proliferation and depending on its concentration, it can promote death of hippocampal neurons by apoptosis or by necrosis. Moreover, LPA mediates microglial activation and is cytotoxic to the neuromicrovascular endothelium. Furthermore, LPA induces death of neural stem/progenitor cells (NS/PC) and inhibits their differentiation towards neurons, an effect not suppressed by the addition of other inflammatory molecules. In addition, LPA maintains neural stem cell differentiation towards glial cells, hence contributes to gliogenesis and inflammation. Our data, together with the literature, strongly suggest that LPA is a key player on the outcome of neural damage and/or repair following injuries, including traumatic brain injury, spinal cord injury and neurodegenerative disorder such as Parkinson's disease, Alzheimer's disease and multiple sclerosis.

Pain: There is a growing wealth of scientific studies strongly suggest that LPA may be dysregulated in neuropathic pain and that LPA may be causal and not coincidental in pain responses. Consequently, drugs targeting LPA itself or the LPA pathway may have the potential to mitigate neuropathic pain. LPA has been shown to be an important mediator in the nervous system influencing processes such as growth cone and process retraction and cell survival, migration, adhesion, and proliferation. A significant role of LPA in the development of neuropathic pain was established using various pharmacological and genetic approaches. Thus, antagonizing LPA could have benefit in the treatment of neuropathic pain, inflammatory pain, chemotherapeutic-induced pain and pain resulting from nerve injury or trauma.

Thus agents that reduce the effective concentration of LPA, such as Lpath's anti-LPA monoclonal antibodies, are believed to be useful in methods for treating diseases and conditions such as those associated with wound healing and fibrosis, apoptosis, angiogenesis and neovascularization, vascular permeability and inflammation. Diseases associated with aberrant levels of LPA are believed to be particularly suitable for treatment with antibodies that bind and neutralize LPA.

Although polyclonal antibodies against naturally-occurring LPA have been reported in the literature (Chen, et al. (2000), Bioorg Med Chem Lett., August 7; 10(15):1691-3), monoclonal antibodies had not been described until the applicants developed several monoclonal antibodies, including humanized monoclonal antibodies, against LPAs. For example, see U.S. Patent Application Publication No. 20100034814, which is commonly owned with the instant application and is incorporated herein in its entirety. These anti-LPA antibodies can bind to and neutralize various LPAs and mitigate their biologic and pharmacologic action. Anti-LPA antibodies are, therefore, believed to be useful in prevention and/or treatment of various diseases and conditions associated with excessive, unwanted or aberrant levels of LPA.

Rapid and specific methods of detecting LPA are also desired. Methods for separating and semi-quantitatively measuring phospholipids such as LPA using techniques such as thin-layer chromatography (TLC) followed by gas chromatography (GC) and/or mass spectrometry (MS) are known. For example, lipids may be extracted from the test sample of bodily fluid. Alternatively, thin-layer chromatography may be used to separate various phospholipids. Phospholipids and lysophospholipids can then be visualized on plates, for example, using ultraviolet light. Alternatively, lysophospholipid concentrations can be identified by NMR or HPLC following isolation from phospholipids or as part of the phospholipid. LPA levels have also been determined in ascites from ovarian cancer patients using an assay that relies on LysoPA-specific effects on eukaryotic cells in culture. However, these prior procedures are time-consuming, expensive and variable and typically only semi-quantitative. Enzymatic methods for detecting lysophospholipids such as LPA in biological fluids, and for correlating and detecting conditions associated with altered levels of lysophospholipids, are also known, e.g., as disclosed in U.S. Pat. Nos. 6,255,063 and 6,248,553. The antibodies disclosed herein provide the basis for sensitive and specific methods for detection of LPA.

3. Definitions

Before describing the instant invention in detail, several terms used in the context of the present invention will be defined. In addition to these terms, others are defined elsewhere in the specification, as necessary. Unless otherwise expressly defined herein, terms of art used in this specification will have their art-recognized meanings.

The term "aberrant" means excessive or unwanted, for example in reference to levels or effective concentrations of a cellular target such as a protein or bioactive lipid.

The term "antibody" ("Ab") or "immunoglobulin" (Ig) refers to any form of a peptide, polypeptide derived from, modeled after or encoded by, an immunoglobulin gene, or fragment thereof, that is capable of binding an antigen or epitope. See, e.g., Immunobiology, Fifth Edition, C. A. Janeway, P. Travers, M., Walport, M. J. Shlomchiked., ed. Garland Publishing (2001). The term "antibody" is used herein in the broadest sense, and encompasses monoclonal, polyclonal or multispecific antibodies, minibodies, heteroconjugates, diabodies, triabodies, chimeric, antibodies, synthetic antibodies, antibody fragments, and binding agents that employ the complementarity determining regions (CDRs) (or variants thereof that retain antigen binding activity) of the parent antibody. Antibodies are defined herein as retaining at least one desired activity of the parent antibody. Desired activities can include the ability to bind the antigen specifically, the ability to inhibit proleration in vitro, the ability to inhibit angiogenesis in vivo, and the ability to alter cytokine profile(s) in vitro. Herein, antibodies and antibody fragments, variants, and derivatives may also be referred to as "immune-derived moieties", in that such molecules, or at least the antigen-binding portion(s) thereof, have been derived from an anti-LPA antibody.

Native antibodies (native immunoglobulins) are usually heterotetrameric glycoproteins of about 150,000 Daltons, typically composed of two identical light (L) chains and two identical heavy (H) chains. Each light chain is typically linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain (VH), also referred to as the variable domain, followed by a number of constant domains. Each light chain has a variable domain at one end (VL) and a constant domain at its other end; the constant domain of the light chain is aligned with the first constant domain of the heavy chain, and the light-chain variable domain is aligned with the variable domain of the heavy chain. Particular amino acid residues form an interface between the light- and heavy-chain variable domains. The terms "variable domain" and "variable region" are used interchangeably. The terms "constant domain" and "constant region" are also interchangeable with each other.

Three hypervariable regions (also known as complementarity determining regions or CDRs) in each of the VH and VL regions form the unique antigen binding site of the molecule. Most of the amino acid sequence variation in the antibody molecule is within the CDRs, giving the antibody its specificity for its antigen.

The light chains of antibodies (immunoglobulins) from any vertebrate species can be assigned to one of two clearly distinct types, called kappa ( ) and lambda ( ) based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

An "antibody derivative" is an immune-derived moiety, i.e., a molecule that is derived from an antibody. This comprehends, for example, antibody variants, antibody fragments, chimeric antibodies, humanized antibodies, multivalent antibodies, antibody conjugates and the like, which retain a desired level of binding activity for antigen.

As used herein, "antibody fragment" refers to a portion of an intact antibody that includes the antigen binding site or variable domains of an intact antibody, wherein the portion can be free of the constant heavy chain domains (e.g., CH2, CH3, and CH4) of the Fc region of the intact antibody. Alternatively, portions of the constant heavy chain domains (e.g., CH2, CH3, and CH4) can be included in the "antibody fragment". Antibody fragments retain antigen-binding and include Fab, Fab', F(ab')2, Fd, and Fv fragments; diabodies; triabodies; single-chain antibody molecules (sc-Fv); minibodies, nanobodies, and multispecific antibodies formed from antibody fragments. Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two antigen-combining sites and is still capable of cross-linking antigen. By way of example, a Fab fragment also contains the constant domain of a light chain and the first constant domain (CH1) of a heavy chain. "Fv" is the minimum antibody fragment that contains a complete antigen-recognition and -binding site. This region consists of a dimer of one heavy chain and one light chain variable domain in tight, non-covalent association. It is in this configuration that the three hypervariable regions of each variable domain interact to define an antigen-binding site on the surface of the VH-VL dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site. "Single-chain Fv" or "sFv" antibody fragments comprise the VH and VL domains of antibody, wherein these domains are present in a single polypeptide chain. Generally, the Fv polypeptide further comprises a polypeptide linker between the VH and VL domains that enables the sFv to form the desired structure for antigen binding. For a review of sFv, see Pluckthun in The Pharmacology of Monoclonal Antibodies, vol. 113, Rosenburg and Moore eds. Springer-Verlag, New York, pp. 269-315 (1994).

The Fab fragment also contains the constant domain of the light chain and the first constant domain (CH1) of the heavy chain. Fab' fragments differ from Fab fragments by the addition of a few residues at the carboxyl terminus of the heavy chain CH1 domain including one or more cysteine(s) from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them. Other chemical couplings of antibody fragments are also known.

An "antibody variant," in this case an anti-LPA antibody variant, refers herein to a molecule which differs in amino acid sequence from a native anti-LPA antibody amino acid sequence by virtue of addition, deletion and/or substitution of one or more amino acid residue(s) in the antibody sequence and which retains at least one desired activity of the parent anti-binding antibody. Desired activities can include the ability to bind the antigen specifically, the ability to inhibit proliferation in vitro, the ability to inhibit angiogenesis in vivo, and the ability to alter cytokine profile in vitro. The amino acid change(s) in an antibody variant may be within a variable domain or a constant region of a light chain and/or a heavy chain, including in the Fc region, the Fab region, the CH1 domain, the CH2 domain, the CH3 domain, and the hinge region. In one embodiment, the variant comprises one or more amino acid substitution(s) in one or more hypervariable region(s) of the parent antibody. For example, the variant may comprise at least one, e.g. from about one to about ten, and preferably from about two to about five, substitutions in one or more hypervariable regions of the parent antibody. Ordinarily, the variant will have an amino acid sequence having at least 65% amino acid sequence identity with the parent antibody heavy or light chain variable domain sequences, more preferably at least 75%, more preferably at 80%, more preferably at least 85%, more preferably at least 90%, and most preferably at least 95%. In some situations a sequence identity of at least 50% is preferred, where other characteristics of the molecule convey desired attributes such as binding and specificity. Identity or homology with respect to this sequence is defined herein as the percentage of amino acid residues in the candidate sequence that are identical with the parent antibody residues, after aligning the sequences and introducing gaps, if necessary, to achieve the maximum percent sequence identity. None of N-terminal, C-terminal, or internal extensions, deletions, or insertions into the antibody sequence shall be construed as affecting sequence identity or homology. The variant retains the ability to bind LPA and preferably has desired activities which are superior to those of the parent antibody. For example, the variant may have a stronger binding affinity, enhanced ability to reduce angiogenesis and/or halt tumor progression. To analyze such desired properties (for example les immunogenic, longer half-life, enhanced stability, enhanced potency), one should compare a Fab form of the variant to a Fab form of the parent antibody or a full length form of the variant to a full length form of the parent antibody, for example, since it has been found that the format of the anti-sphingolipid antibody impacts its activity in the biological activity assays disclosed herein. The variant antibody of particular interest herein can be one which displays at least about 10 fold, preferably at least about % 5, 25, 59, or more of at least one desired activity. The preferred variant is one that has superior biophysical properties as measured in vitro or superior activities biological as measured in vitro or in vivo when compared to the parent antibody.

An "anti-LPA agent" refers to any therapeutic agent that binds LPA, and includes antibodies, antibody variants, antibody-derived molecules or non-antibody-derived moieties that bind LPA and its variants.

A "bioactive lipid" refers to a lipid signaling molecule. Bioactive lipids are distinguished from structural lipids (e.g., membrane-bound phospholipids) in that they mediate extracellular and/or intracellular signaling and thus are involved in controlling the function of many types of cells by modulating differentiation, migration, proliferation, secretion, survival, and other processes. In vivo, bioactive lipids can be found in extracellular fluids, where they can be complexed with other molecules, for example serum proteins such as albumin and lipoproteins, or in "free" form, i.e., not complexed with another molecule species. As extracellular mediators, some bioactive lipids alter cell signaling by activating membrane-bound ion channels or GPCRs or enzymes or factors that, in turn, activate complex signaling systems that result in changes in cell function or survival. As intracellular mediators, bioactive lipids can exert their actions by directly interacting with intracellular components such as enzymes, ion channels, or structural elements such as actin.

Examples of bioactive lipids include sphingolipids such as ceramide, ceramide-1-phosphate (C1P), sphingosine, sphinganine, sphingosylphosphorylcholine (SPC) and sphingosine-1-phosphate (S1P). Sphingolipids and their derivatives and metabolites are characterized by a sphingoid backbone (derived from sphingomyelin). Sphingolipids and their derivatives and metabolites represent a group of extracellular and intracellular signaling molecules with pleiotropic effects on important cellular processes. They include sulfatides, gangliosides and cerebrosides. Other bioactive lipids are characterized by a glycerol-based backbone; for example, lysophospholipids such as lysophosphatidyl choline (LPC) and various lysophosphatidic acids (LPA), as well as phosphatidylinositol (PI), phosphatidylethanolamine (PEA), phosphatidic acid, platelet activating factor (PAF), cardiolipin, phosphatidylglycerol (PG) and diacylglyceride (DG). Yet other bioactive lipids are derived from arachidonic acid; these include the eicosanoids (including the eicosanoid metabolites such as the HETEs, cannabinoids, leukotrienes, prostaglandins, lipoxins, epoxyeicosatrienoic acids, and isoeicosanoids), non-eicosanoid cannabinoid mediators. Other bioactive lipids, including other phospholipids and their derivatives, may also be used according to the instant invention.

In some embodiments of the invention it may be preferable to target glycerol-based bioactive lipids (those having a glycerol-derived backbone, such as the LPAs) for antibody production, as opposed to sphingosine-based bioactive lipids (those having a sphingoid backbone, such as sphingosine and S1P). In other embodiments it may be desired to target arachidonic acid-derived bioactive lipids for antibody generation, and in other embodiments arachidonic acid-derived and glycerol-derived bioactive lipids but not sphingoid-derived bioactive lipids are preferred. Together the arachidonic acid-derived and glycerol-derived bioactive lipids may be referred to herein as "non-sphingoid bioactive lipids."

Specifically excluded from the class of bioactive lipids according to the invention are phosphatidylcholine and phosphatidylserine, as well as their metabolites and derivatives that function primarily as structural members of the inner and/or outer leaflet of cellular membranes.

The term "biologically active," in the context of an antibody or antibody fragment or variant, refers to an antibody or antibody fragment or antibody variant that is capable of binding the desired epitope and in some ways exerting a biologic effect. Biological effects include, but are not limited to, the modulation of a growth signal, the modulation of an anti-apoptotic signal, the modulation of an apoptotic signal, the modulation of the effector function cascade, and modulation of other ligand interactions.

A "biomarker" is a specific biochemical in the body which has a particular molecular feature that makes it useful for measuring the progress of disease or the effects of treatment. For example, S1P is a biomarker for certain hyperproliferative and/or cardiovascular conditions.

"Cardiovascular therapy" encompasses cardiac therapy (treatment of myocardial ischemia and heart failure) as well as the prevention and/or treatment of other diseases associated with the cardiovascular system, such as heart disease. The term "heart disease" encompasses any type of disease, disorder, trauma, or surgical treatment that involves the heart or myocardial tissue. Of particular interest are conditions associated with tissue remodeling. The term "cardiotherapeutic agent" refers to an agent that is therapeutic to diseases and diseases caused by or associated with cardiac and myocardial diseases and disorders.

A "carrier" refers to a moiety adapted for conjugation to a hapten, thereby rendering the hapten immunogenic. A representative, non-limiting class of carriers is proteins, examples of which include albumin, keyhole limpet hemocyanin, hemaglutanin, tetanus, and diptheria toxoid. Other classes and examples of carriers suitable for use in accordance with the invention are known in the art. These, as well as later discovered or invented naturally occurring or synthetic carriers, can be adapted for application in accordance with the invention.

As used herein, the expressions "cell," "cell line," and "cell culture" are used interchangeably and all such designations include progeny. Thus, the words "transformants" and "transformed cells" include the primary subject cell and cultures derived there from without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

The term "chemotherapeutic agent" means anti-cancer and other anti-hyperproliferative agents. Thus chemotherapeutic agents are a subset of therapeutic agents in general. Chemotherapeutic agents include, but are not limited to: DNA damaging agents and agents that inhibit DNA synthesis: anthracyclines (doxorubicin, donorubicin, epirubicin), alkylating agents (bendamustine, busulfan, carboplatin, carmustine, chlorambucil, cyclophosphamide, dacarbazine, hexamethylmelamine, ifosphamide, lomustine, mechlorethamine, melphalan, mitotane, mytomycin, pipobroman, procarbazine, streptozocin, thiotepa, and triethylenemelamine), platinum derivatives (cisplatin, carboplatin, cis diammine-dichloroplatinum), and topoisomerase inhibitors (Camptosar); antimetabolites such as capecitabine, chlorodeoxyadenosine, cytarabine (and its activated form, ara-CMP), cytosine arabinoside, dacabazine, floxuridine, fludarabine, 5-fluorouracil, 5-DFUR, gemcitabine, hydroxyurea, 6-mercaptopurine, methotrexate, pentostatin, trimetrexate, 6-thioguanine); anti-angiogenics (bevacizumab, thalidomide, sunitinib, lenalidomide, TNP-470, 2-methoxyestradiol, ranibizumab, sorafenib, erlotinib, bortezomib, pegaptanib, endostatin); vascular disrupting agents (flavonoids/flavones, DMXAA, combretastatin derivatives such as CA4DP, ZD6126, AVE8062A, etc.); biologics such as antibodies (Herceptin, Avastin, Panorex, Rituxin, Zevalin, Mylotarg, Campath, Bexxar, Erbitux); endocrine therapy: aromatase inhibitors (4-hydroandrostendione, exemestane, aminoglutehimide, anastrazole, letozole), anti-estrogens (Tamoxifen, Toremifine, Raoxifene, Faslodex), steroids such as dexamethasone; immuno-modulators: cytokines such as IFN-beta and IL2), inhibitors to integrins, other adhesion proteins and matrix metalloproteinases); histone deacetylase inhibitors like suberoylanilide hydroxamic acid; inhibitors of signal transduction such as inhibitors of tyrosine kinases like imatinib (Gleevec); inhibitors of heat shock proteins like 17-N-allylamino-17-demethoxygeldanamycin; retinoids such as all trans retinoic acid; inhibitors of growth factor receptors or the growth factors themselves; anti-mitotic compounds and/or tubulin-depolymerizing agents such as the taxoids (paclitaxel, docetaxel, taxotere, BAY 59-8862), navelbine, vinblastine, vincristine, vindesine and vinorelbine; anti-inflammatories such as COX inhibitors and cell cycle regulators, e.g., check point regulators and telomerase inhibitors.

The term "chimeric" antibody (or immunoglobulin) refers to a molecule comprising a heavy and/or light chain which is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (Cabilly, et al., infra; Morrison et al., Proc. Natl. Acad. Sci. U.S.A., vol. 81:6851 (1984)). One example of a chimeric antibody is an antibody containing murine variable domains (VL and VH) and human constant domains. However, antibody sequences may be vertebrate or invertebrate in origin, e.g., from mammal, bird or fish, including cartilaginous fish, rodents, canines, felines, ungulate animals and primates, including humans.

The term "combination therapy" refers to a therapeutic regimen that involves the provision of at least two distinct therapies to achieve an indicated therapeutic effect. For example, a combination therapy may involve the administration of two or more chemically distinct active ingredients, for example, a fast-acting chemotherapeutic agent and an anti-lipid antibody. Alternatively, a combination therapy may involve the administration of an anti-lipid antibody and/or one or more chemotherapeutic agents, alone or together with the delivery of another treatment, such as radiation therapy and/or surgery. In the context of the administration of two or more chemically distinct active ingredients, it is understood that the active ingredients may be administered as part of the same composition or as different compositions. When administered as separate compositions, the compositions comprising the different active ingredients may be administered at the same or different times, by the same or different routes, using the same of different dosing regimens, all as the particular context requires and as determined by the attending physician. Similarly, when one or more anti-lipid antibody species, for example, an anti-LPA antibody, alone or in conjunction with one or more chemotherapeutic agents are combined with, for example, radiation and/or surgery, the drug(s) may be delivered before or after surgery or radiation treatment.

The expression "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

A "derivatized bioactive lipid" is a bioactive lipid, e.g., LPA, which has a polar head group and at least one hydrocarbon chain, wherein a carbon atom within the hydrocarbon chain is derivatized with a pendant reactive group (e.g., a sulfhydryl (thiol) group, a carboxylic acid group, a cyano group, an ester, a hydroxy group, an alkene, an alkyne, an acid chloride group or a halogen atom) that may or may not be protected. This derivatization serves to activate the bioactive lipid for reaction with a molecule, e.g., for conjugation to a carrier.

A "derivatized bioactive lipid conjugate" refers to a derivatized bioactive lipid that is covalently conjugated to a carrier. The carrier may be a protein molecule or may be a moiety such as polyethylene glycol, colloidal gold, adjuvants or silicone beads. A derivatized bioactive lipid conjugate may be used as an immunogen for generating an antibody response according to the instant invention, and the same or a different bioactive lipid conjugate may be used as a detection reagent for detecting the antibody thus produced. In some embodiments the derivatized bioactive lipid conjugate is attached to a solid support when used for detection.

The term "diabodies" refers to small antibody fragments with two antigen-binding sites, which fragments comprise a heavy chain variable domain (VH) connected to a light chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger, et al., Proc. Natl. Acad. Sci. USA 90:6444-6448 (1993).

"Effective concentration" refers to the absolute, relative, and/or available concentration and/or activity, for example of certain undesired bioactive lipids. In other words, the effective concentration of a bioactive lipid is the amount of lipid available, and able, to perform its biological function. In the present invention, an immune-derived moiety such as, for example, a monoclonal antibody directed to a bioactive lipid (such as, for example, C1P) is able to reduce the effective concentration of the lipid by binding to the lipid and rendering it unable to perform its biological function. In this example, the lipid itself is still present (it is not degraded by the antibody, in other words) but can no longer bind its receptor or other targets to cause a downstream effect, so "effective concentration" rather than absolute concentration is the appropriate measurement. Lowering the effective concentration of a bioactive lipid is also referred to as "neutralizing" the target lipid or its undesired effects, including downstream effects. Methods and assays exist for directly and/or indirectly measuring effective concentrations of bioactive lipids.

An "epitope" or "antigenic determinant" refers to that portion of an antigen that reacts with an antibody antigen-binding portion derived from an antibody.

The term "expression cassette" refers to a nucleotide molecule capable of affecting expression of a structural gene (i.e., a protein coding sequence, such as an antibody of the invention) in a host compatible with such sequences. Expression cassettes include at least a promoter operably linked with the polypeptide-coding sequence, and, optionally, with other sequences, e.g., transcription termination signals. Additional regulatory elements necessary or helpful in effecting expression may also be used, e.g., enhancers. Thus, expression cassettes include plasmids, expression vectors, recombinant viruses, any form of recombinant "naked DNA" vector, and the like.

A "fully human antibody" can refer to an antibody produced in a genetically engineered (i.e., transgenic) animal, typically a mammal, usually a mouse (e.g., as can be obtained from Medarex) that, when presented with a suitable immunogen, can produce a human antibody that does not necessarily require CDR grafting. These antibodies are fully "human" in that they generated from an animal (e.g., a transgenic mouse) in which the non-human antibody genes are replaced or suppressed and replaced with some or all of the human immunoglobulin genes. In other words, antibodies of the invention include those generated against bioactive lipids, specifically LPA, when presented in an immunogenic form to mice or other animals genetically engineered to produce human frameworks for relevant CDRs.

A "hapten" is a substance that is non-immunogenic but can react with an antibody or antigen-binding portion derived from an antibody. In other words, haptens have the property of antigenicity but not immunogenicity. A hapten is generally a small molecule that can, under most circumstances, elicit an immune response (i.e., act as an antigen) only when attached to a carrier, for example, a protein, polyethylene glycol (PEG), colloidal gold, silicone beads, or the like. The carrier may be one that also does not elicit an immune response by itself.

The term "heteroconjugate antibody" can refer to two covalently joined antibodies. Such antibodies can be prepared using known methods in synthetic protein chemistry, including using crosslinking agents. As used herein, the term "conjugate" refers to molecules formed by the covalent attachment of one or more antibody fragment(s) or binding moieties to one or more polymer molecule(s).

"Humanized" forms of non-human (e.g., murine) antibodies are chimeric antibodies that contain minimal sequence derived from non-human immunoglobulin. Or, looked at another way, a humanized antibody is a human antibody that also contains selected sequences from non-human (e.g., murine) antibodies in place of the human sequences. A humanized antibody can include conservative amino acid substitutions or non-natural residues from the same or different species that do not significantly alter its binding and/or biologic activity. Such antibodies are chimeric antibodies that contain minimal sequence derived from non-human immunoglobulins. For the most part, humanized antibodies are human immunoglobulins (recipient antibody) in which residues from a complementary-determining region (CDR) of the recipient are replaced by residues from a CDR of a non-human species (donor antibody) such as mouse, rat, camel, bovine, goat, or rabbit having the desired properties. In some instances, framework region (FR) residues of the human immunoglobulin are replaced by corresponding non-human residues.

Furthermore, humanized antibodies can comprise residues that are found neither in the recipient antibody nor in the imported CDR or framework sequences. These modifications are made to further refine and maximize antibody performance. Thus, in general, a humanized antibody will comprise all of at least one, and in one aspect two, variable domains, in which all or all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), or that of a human immunoglobulin. See, e.g., Cabilly, et al., U.S. Pat. No. 4,816,567; Cabilly, et al., European Patent No. 0,125,023 B1; Boss, et al., U.S. Pat. No. 4,816,397; Boss, et al., European Patent No. 0,120,694 B1; Neuberger, et al., WO 86/01533; Neuberger, et al., European Patent No. 0,194,276 B1; Winter, U.S. Pat. No. 5,225,539; Winter, European Patent No. 0,239,400 B1; Padlan, et al., European Patent Application No. 0,519,596 A1; Queen, et al. (1989), Proc. Nat'l Acad. Sci. USA, vol. 86:10029-10033). For further details, see Jones, et al., Nature 321:522-525 (1986); Reichmann, et al., Nature 332:323-329 (1988); and Presta, Curr. Op. Struct. Biol. 2:593-596 (1992), and Hansen, WO2006105062.

The term "hyperproliferative disorder" refers to diseases and disorders associated with, the uncontrolled proliferation of cells, including but not limited to uncontrolled growth of organ and tissue cells resulting in cancers and benign tumors. Hyperproliferative disorders associated with endothelial cells can result in diseases of angiogenesis such as angiomas, endometriosis, obesity, age-related macular degeneration and various retinopathies, as well as the proliferation of endothelial cells and smooth muscle cells that cause restenosis as a consequence of stenting in the treatment of atherosclerosis. Hyperproliferative disorders involving fibroblasts (i.e., fibrogenesis) include, without limitation, disorders of excessive scarring (i.e., fibrosis) such as age-related macular degeneration, cardiac remodeling and failure associated with myocardial infarction, as well as excessive wound healing such as commonly occurs as a consequence of surgery or injury, keloids, and fibroid tumors and stenting.

An "immunogen" is a molecule capable of inducing a specific immune response, particularly an antibody response in an animal to whom the immunogen has been administered. In the instant invention, the immunogen is a derivatized bioactive lipid conjugated to a carrier, i.e., a "derivatized bioactive lipid conjugate". The derivatized bioactive lipid conjugate used as the immunogen may be used as capture material for detection of the antibody generated in response to the immunogen. Thus the immunogen may also be used as a detection reagent. Alternatively, the derivatized bioactive lipid conjugate used as capture material may have a different linker and/or carrier moiety from that in the immunogen.

To "inhibit," particularly in the context of a biological phenomenon, means to decrease, suppress or delay. For example, a treatment yielding "inhibition of tumorigenesis" may mean that tumors do not form at all, or that they form more slowly, or are fewer in number than in the untreated control.

An "isolated" composition is one that has been identified and separated and/or recovered from a component of its natural environment. Contaminant components of its natural environment are materials that would interfere with diagnostic or therapeutic uses for the antibody, and may include enzymes, hormones, and other proteinaceous or nonproteinaceous solutes. In preferred embodiments, the composition is an antibody and will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The word "label" when used herein refers to a detectable compound or composition, such as one that is conjugated directly or indirectly to the antibody. The label may itself be detectable by itself (e.g., radioisotope labels or fluorescent labels) or, in the case of an enzymatic label, may catalyze chemical alteration of a substrate compound or composition that is detectable.

A "liposome" is a small vesicle composed of various types of lipids, phospholipids and/or surfactant that is useful for delivery of a drug (such as the anti-sphingolipid antibodies disclosed herein and, optionally, a chemotherapeutic agent) to a mammal. The components of the liposome are commonly arranged in a bilayer formation, similar to the lipid arrangement of biological membranes. An "isolated" nucleic acid molecule is a nucleic acid molecule that is identified and separated from at least one contaminant nucleic acid molecule with which it is ordinarily associated in the natural source of the antibody nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the antibody where, for example, the nucleic acid molecule is in a chromosomal location different from that of non-engineered cells.

In the context of this invention, a "liquid composition" refers to one that, in its filled and finished form as provided from a manufacturer to an end user (e.g., a doctor or nurse), is a liquid or solution, as opposed to a solid. Here, "solid" refers to compositions that are not liquids or solutions. For example, solids include dried compositions prepared by lyophilization, freeze-drying, precipitation, and similar procedures.

The expression "linear antibodies" when used throughout this application refers to the antibodies described in Zapata, et al. Protein Eng. 8(10):1057-1062 (1995). Briefly, these antibodies comprise a pair of tandem Fd segments (VH-CH1-VH-CH1) that form a pair of antigen binding regions. Linear antibodies can be bispecific or monospecific.

The term "metabolites" refers to compounds from which LPAs are made, as well as those that result from the degradation of LPAs; that is, compounds that are involved in the lysophospholipid metabolic pathways. The term "metabolic precursors" may be used to refer to compounds from which sphingolipids are made.

The term "monoclonal antibody" (mAb) as used herein refers to an antibody obtained from a population of substantially homogeneous antibodies, or to said population of antibodies. The individual antibodies comprising the population are essentially identical, except for possible naturally occurring mutations that may be present in minor amounts. Monoclonal antibodies are highly specific, being directed against a single antigenic site. Furthermore, in contrast to conventional (polyclonal) antibody preparations that typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler, et al., Nature 256:495 (1975), or may be made by recombinant DNA methods (see, e.g., U.S. Pat. No. 4,816,567). The "monoclonal antibodies" may also be isolated from phage antibody libraries using the techniques described in Clackson, et al., Nature 352:624-628 (1991) and Marks, et al., J. Mol. Biol. 222:581-597 (1991), for example, or by other methods known in the art. The monoclonal antibodies herein specifically include chimeric antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison, et al., Proc. Natl. Acad. Sci. USA 81:6851-6855 (1984)).

"Monotherapy" refers to a treatment regimen based on the delivery of one therapeutically effective compound, whether administered as a single dose or several doses over time.

The term "multispecific antibody" can refer to an antibody, or a monoclonal antibody, having binding properties for at least two different epitopes. In one embodiment, the epitopes are from the same antigen. In another embodiment, the epitopes are from two or more different antigens. Methods for making multispecific antibodies are known in the art. Multispecific antibodies include bispecific antibodies (having binding properties for two epitopes), trispecific antibodies (three epitopes) and so on. For example, multispecific antibodies can be produced recombinantly using the co-expression of two or more immunoglobulin heavy chain/light chain pairs. Alternatively, multispecific antibodies can be prepared using chemical linkage. One of skill can produce multispecific antibodies using these or other methods as may be known in the art. Multispecific antibodies include multispecific antibody fragments. One example of a multispecific (in this case, bispecific) antibody comprehended by this invention is an antibody having binding properties for an S1P epitope and a C1P epitope, which thus is able to recognize and bind to both S1P and C1P. Another example of a bispecific antibody comprehended by this invention is an antibody having binding properties for an epitope from a bioactive lipid and an epitope from a cell surface antigen. Thus the antibody is able to recognize and bind the bioactive lipid and is able to recognize and bind to cells, e.g., for targeting purposes.

"Neoplasia" or "cancer" refers to abnormal and uncontrolled cell growth. A "neoplasm", or tumor or cancer, is an abnormal, unregulated, and disorganized proliferation of cell growth, and is generally referred to as cancer. A neoplasm may be benign or malignant. A neoplasm is malignant, or cancerous, if it has properties of destructive growth, invasiveness, and metastasis. Invasiveness refers to the local spread of a neoplasm by infiltration or destruction of surrounding tissue, typically breaking through the basal laminas that define the boundaries of the tissues, thereby often entering the body's circulatory system. Metastasis typically refers to the dissemination of tumor cells by lymphatics or blood vessels. Metastasis also refers to the migration of tumor cells by direct extension through serous cavities, or subarachnoid or other spaces. Through the process of metastasis, tumor cell migration to other areas of the body establishes neoplasms in areas away from the site of initial appearance.

"Neuropathic pain" is the chronic pain state caused by pathologic changes in the nervous system.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The "parent" antibody herein is one that is encoded by an amino acid sequence used for the preparation of the variant. The parent antibody may be a native antibody or may already be a variant, e.g., a chimeric antibody. For example, the parent antibody may be a humanized or human antibody.

A "patentable" composition, process, machine, or article of manufacture according to the invention means that the subject matter satisfies all statutory requirements for patentability at the time the analysis is performed. For example, with regard to novelty, non-obviousness, or the like, if later investigation reveals that one or more claims encompass one or more embodiments that would negate novelty, non-obviousness, etc., the claim(s), being limited by definition to "patentable" embodiments, specifically exclude the non-patentable embodiment(s). Also, the claims appended hereto are to be interpreted both to provide the broadest reasonable scope, as well as to preserve their validity. Furthermore, the claims are to be interpreted in a way that (1) preserves their validity and (2) provides the broadest reasonable interpretation under the circumstances, if one or more of the statutory requirements for patentability are amended or if the standards change for assessing whether a particular statutory requirement for patentability is satisfied from the time this application is filed or issues as a patent to a time the validity of one or more of the appended claims is questioned.

The term "pharmaceutically acceptable salt" refers to a salt, such as used in formulation, which retains the biological effectiveness and properties of the agents and compounds of this invention and which are is biologically or otherwise undesirable. In many cases, the agents and compounds of this invention are capable of forming acid and/or base salts by virtue of the presence of charged groups, for example, charged amino and/or carboxyl groups or groups similar thereto. Pharmaceutically acceptable acid addition salts may be prepared from inorganic and organic acids, while pharmaceutically acceptable base addition salts can be prepared from inorganic and organic bases. For a review of pharmaceutically acceptable salts (see Berge, et al. (1977), J. Pharm. Sci., vol. 66, 1-19).

A "plurality" means more than one.

The term "promoter" includes all sequences capable of driving transcription of a coding sequence in a cell. Thus, promoters used in the constructs of the invention include cis-acting transcriptional control elements and regulatory sequences that are involved in regulating or modulating the timing and/or rate of transcription of a gene. For example, a promoter can be a cis-acting transcriptional control element, including an enhancer, a promoter, a transcription terminator, an origin of replication, a chromosomal integration sequence, 5' and 3' untranslated regions, or an intronic sequence, which are involved in transcriptional regulation. Transcriptional regulatory regions suitable for use in the present invention include but are not limited to the human cytomegalovirus (CMV) immediate-early enhancer/promoter, the SV40 early enhancer/promoter, the *E. coli* lac or trp promoters, and other promoters known to control expression of genes in prokaryotic or eukaryotic cells or their viruses.

The term "recombinant DNA" refers to nucleic acids and gene products expressed therefrom that have been engineered, created, or modified by man. "Recombinant" polypeptides or proteins are polypeptides or proteins produced by recombinant DNA techniques, for example, from cells transformed by an exogenous DNA construct encoding the desired polypeptide or protein. "Synthetic" polypeptides or proteins are those prepared by chemical synthesis.

The terms "separated", "purified", "isolated", and the like mean that one or more components of a sample contained in a sample-holding vessel are or have been physically removed from, or diluted in the presence of, one or more other sample components present in the vessel. Sample components that may be removed or diluted during a separating or purifying step include, chemical reaction products, non-reacted chemicals, proteins, carbohydrates, lipids, and unbound molecules.

By "solid phase" is meant a non-aqueous matrix such as one to which the antibody of the present invention can adhere. Examples of solid phases encompassed herein include those formed partially or entirely of glass (e.g. controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g. an affinity chromatography column). This term also includes a discontinuous solid phase of discrete particles, such as those described in U.S. Pat. No. 4,275,149.

The term "species" is used herein in various contexts, e.g., a particular species of chemotherapeutic agent. In each context, the term refers to a population of chemically indistinct molecules of the sort referred in the particular context.

The term "specific" or "specificity" in the context of antibody-antigen interactions refers to the selective, non-random interaction between an antibody and its target epitope. Here, the term "antigen" refers to a molecule that is recognized and bound by an antibody molecule or other immune-derived moiety. The specific portion of an antigen that is bound by an antibody is termed the "epitope". This interaction depends on the presence of structural, hydrophobic/hydrophilic, and/or electrostatic features that allow appropriate chemical or molecular interactions between the molecules. Thus an antibody is commonly said to "bind" (or "specifically bind") or be "reactive with" (or "specifically reactive with"), or, equivalently, "reactive against" (or "specifically reactive against") the epitope of its target antigen. Antibodies are commonly described in the art as being "against" or "to" their antigens as shorthand for antibody binding to the antigen. Thus an "antibody that binds C1P," an "antibody reactive against C1P," an "antibody reactive with C1P," an "antibody to C1P" and an "anti-C1P antibody" all have the same meaning in the art. Antibody molecules can be tested for specificity of binding by comparing binding to the desired antigen to binding to unrelated antigen or analogue antigen or antigen mixture under a given set of conditions. Preferably, an antibody according to the invention will lack significant binding to unrelated antigens, or even analogs of the target antigen.

Herein, "stable" refers to an interaction between two molecules (e.g., a peptide and a TLR molecule) that is sufficiently stable such that the molecules can be maintained for the desired purpose or manipulation. For example, a "stable" interaction between a peptide and a TLR molecule refers to one wherein the peptide becomes and remains associated with a TLR molecule for a period sufficient to achieve the desired effect.

A "subject" or "patient" refers to an animal in need of treatment that can be effected by molecules of the invention. Animals that can be treated in accordance with the invention include vertebrates, with mammals such as bovine, canine, equine, feline, ovine, porcine, and primate (including humans and non-human primates) animals being particularly preferred examples.

A "surrogate marker" refers to laboratory measurement of biological activity within the body that indirectly indicates the effect of treatment on disease state. Examples of surrogate markers for hyperproliferative and/or cardiovascular conditions include SPHK and/or S1PRs.

A "therapeutic agent" refers to a drug or compound that is intended to provide a therapeutic effect including, but not limited to: anti-inflammatory drugs including COX inhibitors and other NSAIDS, anti-angiogenic drugs, chemotherapeutic drugs as defined above, cardiovascular agents, immunomodulatory agents, agents that are used to treat neurodegenerative disorders, opthalmic drugs, etc.

A "therapeutically effective amount" (or "effective amount") refers to an amount of an active ingredient, e.g., an agent according to the invention, sufficient to effect treatment when administered to a subject in need of such treatment. Accordingly, what constitutes a therapeutically effective amount of a composition according to the invention may be readily determined by one of ordinary skill in the art. In the context of cancer therapy, a "therapeutically effective amount" is one that produces an objectively measured change in one or more parameters associated with cancer cell survival or metabolism, including an increase or decrease in the expression of one or more genes correlated with the particular cancer, reduction in tumor burden, cancer cell lysis, the detection of one or more cancer cell death markers in a biological sample (e.g., a biopsy and an aliquot of a bodily fluid such as whole blood, plasma, serum, urine, etc.), induction of induction apoptosis or other cell death pathways, etc. Of course, the therapeutically effective amount will vary depending upon the particular subject and condition being treated, the weight and age of the subject, the severity of the disease condition, the particular compound chosen, the dosing regimen to be followed, timing of administration, the manner of administration and the like, all of which can readily be determined by one of ordinary skill in the art. It will be appreciated that in the context of combination therapy, what constitutes a therapeutically effective amount of a particular active ingredient may differ from what constitutes a therapeutically effective amount of the active ingredient when administered as a monotherapy (i.e., a therapeutic regimen that employs only one chemical entity as the active ingredient).

The compositions of the invention are used in methods of bioactive lipid-based therapy. As used herein, the terms "therapy" and "therapeutic" encompasses the full spectrum of prevention and/or treatments for a disease, disorder or physical trauma. A "therapeutic" agent of the invention may act in a manner that is prophylactic or preventive, including those that incorporate procedures designed to target individuals that can be identified as being at risk (pharmacogenetics); or in a manner that is ameliorative or curative in nature; or may act to slow the rate or extent of the progression of at least one symptom of a disease or disorder being treated; or may act to minimize the time required, the occurrence or extent of any discomfort or pain, or physical limitations associated with recuperation from a disease, disorder or physical trauma; or may be used as an adjuvant to other therapies and treatments.

The term "treatment" or "treating" means any treatment of a disease or disorder, including preventing or protecting against the disease or disorder (that is, causing the clinical symptoms not to develop); inhibiting the disease or disorder (i.e., arresting, delaying or suppressing the development of clinical symptoms; and/or relieving the disease or disorder (i.e., causing the regression of clinical symptoms). As will be appreciated, it is not always possible to distinguish between "preventing" and "suppressing" a disease or disorder because the ultimate inductive event or events may be unknown or latent. Those "in need of treatment" include those already with the disorder as well as those in which the disorder is to be prevented. Accordingly, the term "prophylaxis" will be understood to constitute a type of "treatment" that encompasses both "preventing" and "suppressing". The term "protection" thus includes "prophylaxis".

The term "therapeutic regimen" means any treatment of a disease or disorder using chemotherapeutic and cytotoxic agents, radiation therapy, surgery, gene therapy, DNA vaccines and therapy, siRNA therapy, anti-angiogenic therapy, immunotherapy, bone marrow transplants, aptamers and other biologics such as antibodies and antibody variants, receptor decoys and other protein-based therapeutics.

The "variable" region of an antibody comprises framework and complementarity determining regions (CDRs, otherwise known as hypervariable regions). The variability is not evenly distributed throughout the variable domains of antibodies. It is concentrated in six CDR segments, three in each of the light chain and the heavy chain variable domains. The more highly conserved portions of variable domains are called the framework region (FR). The variable domains of native heavy and light chains each comprise four FRs (FR1, FR2, FR3 and FR4, respectively), largely adopting a β-sheet configuration, connected by three hypervariable regions, which form loops connecting, and in some cases forming part of, the beta-sheet structure. The term "hypervariable region" when used herein refers to the amino acid residues of an antibody which are responsible for antigen binding. The hypervariable region comprises amino acid residues from a "complementarity determining region" or "CDR" (for example residues 24-34 (L1), 50-56 (L2) and 89-97 (L3) in the light chain variable domain and 31-35 (H1), 50-65 (H2) and 95-102 (H3) in the heavy chain variable domain; Kabat, et al., Sequences of Proteins of Immunological Interest, 5th Ed. Public Health Service, National Institutes of Health, Bethesda, Md. (1991)) and/or those residues from a "hypervariable loop" (for example, residues 26-32 (L1), 50-52 (L2) and 91-96 (L3) in the light chain variable domain and 26-32 (H1), 53-55 (H2) and 96-101 (H3) in the heavy chain variable domain; Chothia and Lesk J. Mol. Biol. 196:901-917 (1987)). "Framework" or "FR" residues are those variable domain residues other than the hypervariable region residues as herein defined.

The hypervariable regions in each chain are held together in close proximity by the FRs and, with the hypervariable regions from the other chain, contribute to the formation of the antigen-binding site of antibodies (see Kabat, et al., Sequences of Proteins of Immunological Interest, 5th Ed. Public Health Service, National Institutes of Health, Bethesda, Md. (1991), pages 647-669). The constant domains are not involved directly in binding an antibody to an antigen, but exhibit various effector functions, such as participation of the antibody in antibody-dependent cellular toxicity.

A "vector" or "plasmid" or "expression vector" refers to a nucleic acid that can be maintained transiently or stably in a cell to effect expression of one or more recombinant genes. A vector can comprise nucleic acid, alone or complexed with other compounds. A vector optionally comprises viral or bacterial nucleic acids and/or proteins, and/or membranes. Vectors include, but are not limited to, replicons (e.g., RNA replicons, bacteriophages) to which fragments of DNA may be attached and become replicated. Thus, vectors include, but are not limited to, RNA, autonomous self-replicating circular or linear DNA or RNA and include both the expression and non-expression plasmids. Plasmids can be commercially available, publicly available on an unrestricted basis, or can be constructed from available plasmids as reported with published protocols. In addition, the expression vectors may also contain a gene to provide a phenotypic trait for selection of transformed host cells such as dihydrofolate reductase or neomycin resistance for eukaryotic cell culture, or such as tetracycline or ampicillin resistance in *E. coli*.

SUMMARY OF THE INVENTION

The present application describes methods of treating or preventing pain. The practice of the invention comprises administering to a subject, including a human subject, having or believed to be at risk of having pain, an antibody or antibody fragment that binds and neutralizes LPA. The antibody may be a polyclonal or monoclonal antibody, or an antibody fragment that retains LPA-binding activity. Preferred are human or humanized monoclonal antibodies or fragments thereof that bind LPA.

The pain treated in accordance with the instant methods can be acute or chronic pain. The instant methods are particularly useful for treating or preventing pain such as neuropathic pain, and pain (including neuropathic pain) due to injury, trauma, or damage to the central or peripheral nervous system, inflammation, drug exposure, diabetes, viral disease, metabolic disease, ischemic insult, nutrient deficiency, toxin exposure, cancer, or cancer treatment.

The foregoing and other aspects of the invention will become more apparent from the following detailed description, accompanying drawings, and the claims. Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

BRIEF DESCRIPTION OF THE DRAWINGS

A brief summary of each of the figures is provided below.

FIG. 1: FIG. 1 contains three parts.

FIG. 2: FIG. 2 contains three parts.

FIG. 3 is a bar graph showing the paw withdrawal threshold (PWT) for control or diabetic rats. Control rats received intrathecal and intravenous injection of vehicle (Veh). Diabetic (D) rats were randomized in the following groups: Veh+D, intrathecal and intravenous injection of vehicle, Low dose+D, intravenous injection anti-LPA-mAb (10 mg/kg)+intrathecal injection of anti-LPA-mAb (2 ug/10 µL) and High dose+D intravenous injection anti-LPA-mAb (10 mg/kg)+intrathecal injection of anti-LPA-mAb (10 ug/10 µL).

FIG. 4: FIG. 4 is a two-part figure showing the effect of anti-LPA antibody on paw withdrawal latency, a measure of pain, in an interventional study in diabetic rats.

FIG. 5: FIG. 5 is a two-part figure showing the effect of anti-LPA antibody on paw withdrawal latency, a measure of pain.

FIG. 6: FIG. 6 is a two-part line graph showing the effect of anti-LPA antibody on two measures of pain over time.

FIG. 7 is a bar graph showing inhibition of pain vocalization in arthritic rats after treatment with humanized anti-LPA antibody LT3015. The antibody was given at three doses (1.6, 8 and 40 mg/kg) in this preliminary study. The two higher doses decreased pain vocalization to the level seen after treatment with Naproxen, the positive control. The lowest dose (1.6 mg/kg) had an intermediate effect and the non-specific antibody had a minimal effect on pain vocalization.

FIG. 8 is a line graph showing the effects of murine anti-LPA antibody B3 (shown in this graph as 504B3) and LT1015 on paclitaxel-induced neuropathic pain. When compared to the vehicle group (□), administration of paclitaxel (●) led to a time-dependent development of mechano-allodynia, which was significantly attenuated at 16 h by intravenous delivery of 504B3 (▲), but not by LT1015 (▼). Results are expressed as mean±SEM. Behavioral data for 3 animals was analyzed by two-tailed, two-way ANOVA with Bonferroni post hoc comparisons to the paclitaxel group where $P<0.01$ and $P<0.001$ for paclitaxel vs vehicle and †$P<0.05$ for paclitaxel+504B3 vs paclitaxel.

DETAILED DESCRIPTION OF THE INVENTION

Anti-LPA Agents, Including Anti-LPA Antibodies

1. Introduction

Figure 1A:
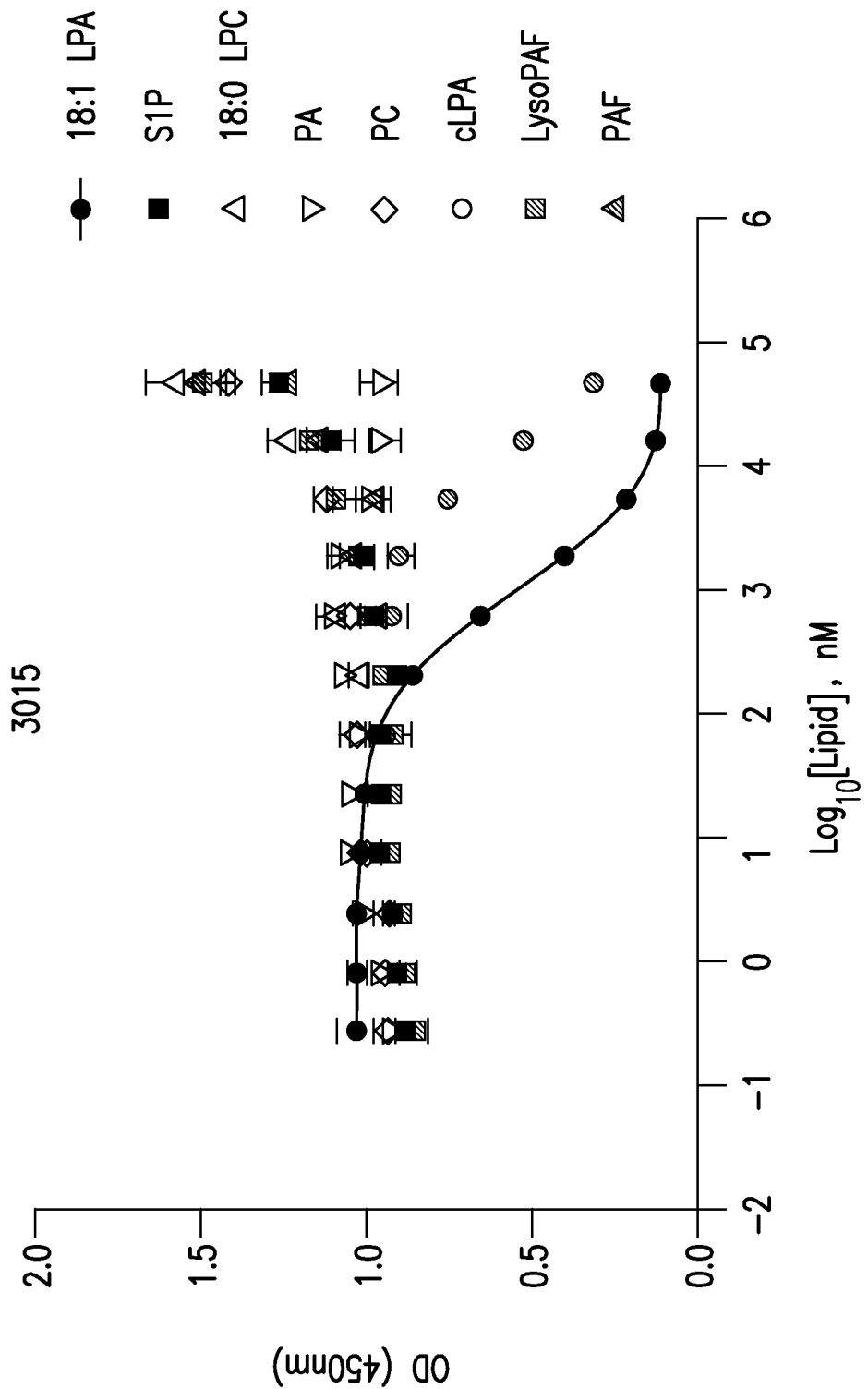
FIGS. 1a, 1b and 1c are line graphs showing the binding specificity of the humanized anti-LPA antibodies, LT3015, LT3114 and murine mAb, B3, respectively, as measured in an ELISA-based competition binding assay.

The use of monoclonal antibodies (mAbs) as a therapeutic treatment for a variety of diseases and disorders is rapidly increasing because they have been shown to be safe and efficacious therapeutic agents. Approved therapeutic monoclonal antibodies include Avastin™, Erbitux™, and Rituxan™. Additional monoclonal antibodies are in various phases of clinical development for a variety of diseases with the majority targeting various forms of cancer. In general, monoclonal antibodies are generated in non-human mammals. The therapeutic utility of murine monoclonal antibodies may be improved with chimerization or humanization of non-human mammalian antibodies. Humanization greatly lessens the development of an immune response against the administered therapeutic monoclonal antibodies and thereby avoids the reduction of half-life and therapeutic efficacy consequent on such a response. For the most part, the humanization process consists of grafting the murine complementary determining regions (CDRs) into the framework region (FR) of a human immunoglobulin. Backmutation to murine amino acid residues of selected residues in the FR is often required to improve or regain affinity that is lost in the initial grafted construct.

The manufacture of monoclonal antibodies is a complex process that stems from the variability of the immunoglobulin protein itself. The heterogeneity can be attributed to the formation of alternative disulfide pairings, deamidation and the formation of isoaspartyl residues, methionine and cysteine oxidation, cyclization of N-terminal glutamine residues to pyroglutamate and partial enzymatic cleavage of C-terminal lysines by mammalian carboxypeptidases. Engineering is commonly applied to antibody molecules to improve their properties, such as enhanced stability, resistance to proteases, aggregation behavior and enhance the expression level in heterologous systems.

2. Disease Associations of LPA and Therapeutic Uses for Anti-LPA Agents

LPA has been associated with a number of diseases and disorders, many of which are associated with aberrant levels of LPA. For review, see Gardell, et al., (2006) Trends Mol Med. 12(2):65-75, and Chun J. and Rosen, H., (2006) Curr. Pharma. Design 12:161-171. These include autoimmune disorders such as diabetes, multiple sclerosis and scleroderma; hyperproliferative disorders including cancer; pain, disorders associated with angiogenesis and neovascularization; obesity; neurodegenerative diseases including Alzheimer's disease; schizophrenia, immune-related disorders such as transplant rejection and graft-vs.-host disease, and others. The roles of LPA in many diseases and disorders is further described in, for example, U.S. Patent Application Publication No. 20100034814, which is commonly owned with the instant application and is incorporated herein in its entirety and for all purposes.

a. Pain

Pain is the most common reason for doctor visits in the US and is present as part of a broad spectrum of diseases, disorders and conditions. Pain may be acute or chronic and may be classified according to location in the body and/or by etiology, although in many cases the etiology of pain is not understood or may be due to several possible causes, which may overlap. Pain may also be described qualitatively, as allodynia (abnormal sensory perception of pain) or hyperalgesia (exaggerated pain sensations), for example.

Neuropathic pain is a complex, often chronic form of pain associated with damage or dysfunction of the nervous system. Simply stated, neuropathic pain is a chronic pain state caused by pathological changes in the nervous system. Myers, et al (2006) Drug Disc. Today 11: 8-20. Causes of acute and/or chronic neuropathic pain include, but are not limited to, injury, trauma, or damage to the central or peripheral nervous system (e.g., spinal cord injury, disc herniation, multiple sclerosis or other degenerative or neurodegenerative disease), inflammation, drug exposure (for example, cytotoxics such as paclitaxel (TAXOL), cisplatin, and other chemotherapeutic agents), diabetes, viral disease (such as, for example, HIV and herpes zoster), metabolic disease, severe ischemic insults, nutrient deficiency, toxin exposure, and cancer. Cancer neuropathic pain may result directly from tumor impingement on nerves, or indirectly such as from radiation, surgery, or drug treatment. Neuropathic pain is mediated through neuroinflammatory mechanisms controlled by inflammatory responses to the initial insult and affecting nervous system tissue. Myers, et al (2006), Drug Disc. Today 11: 8-20. Many inflammatory mediators, such as TNF, have been found to be pivotal in neuropathic pain. Leung L, Cahill C M. (2010) J Neuroinflamm., 7:27. Neuropathic pain is unresponsive to most common painkillers.

Inflammatory mediators are involved in the genesis, persistence, and severity of pain. IL-6 is a potent pain-generating inflammatory mediator. IL-6 is produced in the rat spinal cord following peripheral nerve injury, with levels of IL-6 levels correlating directly with the intensity of allodynia. Arruda, et al. (2000), Brain Res. 879:216-25. IL-6 levels increase during stress or inflammation, and rheumatoid arthritis is associated with increased levels of IL-6 in synovial fluid. Matsumoto, et al (2006), Rheumatol. Int. 26:1096-1100; Desgeorges, et al. (1997), J. Rheumatol. 24:1510-1516. Neuropathic pain is prevented in IL-6 knockout mice. Xu, et al (1997), Cytokine 9:1028-1033.

IL-8 is a pain-generating inflammatory mediator. Drug treatment of post-herpetic neuralgia showed a decrease of 50% in IL-8 concentrations, and this decrease correlated with pain relief. Kotani, et al. (2000), New Engl. J. Med. 343:1514-1519.

TNF– induces axonal damage, macrophage recruitment and ectopic activity in peripheral nerve fibers and plays a role in the generation of hyperalgesia. TNF is upregulated at the site of peripheral nerve lesions and in patients with neuropathic pain. Thalidomide, a selective blocker of TNF production, reduces hyperalgesia in an animal model of neuropathic pain (chronic constriction injury). George, et al. (2000), Pain 88:267-275.

Bioactive lipids are believed to play important roles in the pathogenesis of pain, including neuropathic pain and pain associated with chemotherapy. A significant role of LPA in the development of neuropathic pain was established using various pharmacological and genetic approaches. LPA is responsible for long-lasting mechanical allodynia and thermal hyperalgesia as well as demyelination and upregulation of pain-related proteins through the LPA1 receptor. In addition, intrathecal injections of LPA induce behavioral, morphological, and biochemical changes such as prolonged sensitivity to pain stimuli accompanied by demyelination of dorsal roots, similar to those observed after nerve ligation. Fujita, R., Kiguchi, N. & Ueda, H. (2007), Neurochem Int 50, 351-5. Wild-type animals with nerve injury develop behavioral allodynia and hyperalgesia paralleled by demyelination in the dorsal root and increased expression of both the protein kinase C isoform within the spinal cord dorsal horn and the 21 calcium channel subunit in dorsal root ganglia. It has been demonstrated that mice lacking the LPA1 receptor gene (Ipa1–/– mice) lose nerve injury-induced neuropathic pain behaviors and phenomena. Inoue, et al. (2004), Nat Med 10, 712-8. Heterozygous mutant mice for the autotaxin gene (atx+/–) showed approximately 50% recovery of nerve injury-induced neuropathic pain. The hyperalgesia was completely abolished in both Ipa1–/– and atx+/– mice. Furthermore, inhibitors of Rho and Rho kinase signaling pathways also prevented neuropathic pain. Mueller, B. K., Mack, H. & Teusch, N. (2005), Nat Rev Drug Discov 4, 387-98. Therefore, targeting LPA biosynthesis and/or LPA1 receptor represents a novel, patentable approach to mitigating nerve-injury-induced neuropathic pain.

Pain associated with chemotherapy is a major dose limiting toxicity of many small molecule chemotherapeutic agents. Indeed, many cases of chemotherapy-induced pain have been reported. For instance, paclitaxel (TAXOL), an anti-neoplastic agent derived from the Pacific yew tree *Taxus brevifolia*, is used to treat a variety of cancers, including ovarian, breast, and non-small cell lung cancer. Paclitaxel's effectiveness, however, is limited by the highly incidental development of severe painful peripheral neuropathy such as numbness and burning pain. An antibody against a bioactive lipid correlated with such pain, for example, LPA (or a derivative of such an antibody that contains a lipid-binding portion thereof), could be administered in combination with paclitaxel in order to reduce the pain associated with the chemotherapeutic agent. As a result of ameliorating this dose-limiting toxicity, the amount of paclitaxel to be administered could be even higher (and thus even more effective) when used in combination with such a monoclonal antibody or antibody derivative. In some embodiments, the chemotherapeutic agent (or other drug) could be conjugated to or otherwise associated with the antibody or antibody derivative, for example, by covalently linking the small molecule chemotherapeutic agent to the antibody, by linking the small molecule chemotherapeutic to a multivalent scaffold to which is also linked a monoclonal antibody or at least one bioactive lipid binding domain derived from a monoclonal antibody specifically reactive against the target bioactive lipid, etc. Diabetic neuropathy in type 1 and 2 diabetes in both humans and animal models is characterized by pathophysiological changes in all components (sensory, motor and autonomic) of the peripheral nervous system. In addition to the changes of primary afferent nerves, central sensitization is believed to be an important mechanism underlying persistent pain, including neuropathic and inflammatory pain. G. Baranauskas, A. Nistri (1998) Prog Neurobiol 54, 349; T. J. Coderre, R. Melzack (1992) J Neurosci 12, 3665; R. Dubner, M. A. Ruda (1992) Trends Neurosci 15, 96; M. J. Millan (1999) Prog Neurobiol 57, 1; C. J. Woolf, S. W. Thompson, (1991) Pain 44, 293.

Recently, a role for LPA has been proposed in central sensitization in persistent pain. Specifically, it was demonstrated that stimulation of primary afferent fibers causes production of LPA in the spinal cord. M. Inoue et al. (2008) J Neurochem 107, 1556. Conversion of LPC to LPA by ATX has been proposed to be a major source of LPA in the CNS responsible for the neuropathic pain. L. Ma et al. (2010) J Pharmacol Exp Ther 333, 540.

At the cellular level, LPA is a potent inducer of morphological changes in neuronal and glial cells. Kingsbury, et al. (2003), Nat Neurosci 6, 1292-9; Jalink, et al. (1993), Cell Growth Differ 4, 247-55; Tigyi, G. & Miledi, R. (1992), J Biol Chem 267, 21360-7 (1992); Fukushima, et al. (2000), Dev Biol 228, 6-18; Yuan, X. B. et al. (2003) Nat Cell Biol 5, 38-45; Fukushima, et al. (2007), Neurochem Int 50, 302-7.

In primary astrocytes, as well as in glioma-derived cell lines, LPA causes reversal of process outgrowth ('stellation'), a process directed by active RhoA and accompanied by reassembly and activation of focal adhesion proteins. Ramakers, G. J. & Moolenaar, W. H. (1998), Exp Cell Res, 245: 252-62. A role for LPA in myelination is also suggested by the finding that LPA promotes cell-cell adhesion and survival in Schwann cells. Weiner, et al. (2001), J Neurosci. 21:7069-78; Ramer, et al (2004), J Neurosci. 24:10796-805.

3. Antibody Generation and Characterization

The instant invention relates to use of anti-LPA antibodies and antibody fragments in the treatment of pain. The generation and characterization of murine and humanized monoclonal antibodies to LPA (and LPA-binding fragments thereof) have been described in several patent applications, including U.S. Patent Application Publication No. 20100034814, which is commonly owned with the instant application and is incorporated herein in its entirety.

4. Pharmaceutical Formulations, Dosing and Routes of Administration

One way to control the amount of undesirable LPA in a patient is by providing a composition that comprises one or more anti-LPA antibodies or antibody fragments to bind one or more LPAs, thereby acting as therapeutic "sponges" that reduce the level of free undesirable LPA. When a compound is stated to be "free," the compound is not in any way restricted from reaching the site or sites where it exerts its undesirable effects. Typically, a free compound is present in blood and tissue, which either is or contains the site(s) of action of the free compound, or from which a compound can freely migrate to its site(s) of action. A free compound may also be available to be acted upon by any enzyme that converts the compound into an undesirable compound.

Anti-LPA antibodies and antibody fragments may be formulated in a pharmaceutical composition that is useful for a variety of purposes, including the treatment of diseases, disorders or physical trauma. Pharmaceutical compositions suitable for antibodies to bioactive lipids (or fragments thereof) are disclosed in US application publication US20100098700, which is commonly assigned with the instant application and is incorporated herein in its entirety.

Pharmaceutical compositions comprising one or more anti-LPA antibodies and antibody fragments of the invention may be incorporated into kits and medical devices for such treatment. Medical devices may be used to administer the pharmaceutical compositions of the invention to a patient in need thereof, and according to one embodiment of the invention, kits are provided that include such devices. Such devices and kits may be designed for routine administration, including self-administration, of the pharmaceutical compositions of the invention. Such devices and kits may also be designed for emergency use, for example, in ambulances or emergency rooms, or during surgery, or in activities where injury is possible but where full medical attention may not be immediately forthcoming (for example, hiking and camping, or combat situations).

Therapeutic formulations of the antibody are prepared for storage by mixing the antibody or antibody fragment having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™, or polyethylene glycol (PEG).

The formulation herein may also contain more than one active compound as necessary for the particular indication being treated, preferably those with complementary activities that do not adversely affect each other. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

The formulations to be used for in vivo administration must be sterile. This is readily accomplished for instance by filtration through sterile filtration membranes.

Sustained-release preparations may be prepared. Suitable examples of sustained-release preparations include semipermeable matrices of solid hydrophobic polymers containing the antibody, which matrices are in the form of shaped articles, e.g., films, or microcapsule. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and γ-ethyl-L-glutamate, non-degradable ethylene-vinyl acetate, degradable lactic acid-glycolic acid copolymers such as the Lupron Depot.™. (injectable microspheres composed of lactic acid-glycolic acid copolymer and leuprolide acetate), and poly-D-(–)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

For therapeutic applications, the anti-LPA agents, e.g., antibodies and/or antibody fragments, of the invention are administered to a mammal, preferably a human, in a pharmaceutically acceptable dosage form such as those discussed above, including those that may be administered to a human parenterally (including intravenous, intraarterial, subcutaneous, intraperitoneal or intramuscular injection or infusion) or by intracranial, intrathecal, intra-cerebrospinal, subcutaneous, intra-articular, intrasynovial, oral, topical, intratracheal or inhalation routes.

For the prevention or treatment of disease, the appropriate dosage of antibody (or antibody fragment) will depend on the type of disease to be treated, as defined above, the severity and course of the disease, whether the antibody (or fragment thereof) is administered for preventive or therapeutic purposes, previous therapy, the patient's clinical history and response to the antibody or antibody fragment, and the discretion of the attending physician. The composition containing the anti-LPA antibody or antibody fragment is suitably administered to the patient at one time or over a series of treatments.

Depending on the type and severity of the disease, about 1 µg/kg to about 50 mg/kg (e.g., 0.1-20 mg/kg) of antibody is an initial candidate dosage for administration to the patient, whether, for example, by one or more separate administrations, or by continuous infusion. A typical daily or weekly dosage might range from about 1 µg/kg to about 20 mg/kg or more, depending on the factors mentioned above. For repeated administrations over several days or longer, depending on the condition, the treatment is repeated until a desired suppression of disease symptoms occurs. However, other dosage regimens may be useful. The progress of this therapy is easily monitored by conventional techniques and assays, including, for example, radiographic imaging. Detection methods using the antibody to determine LPA levels in bodily fluids or tissues may be used in order to optimize patient exposure to the therapeutic antibody.

According to another embodiment of the invention, the composition comprising an agent, e.g, a mAb or Fab, that interferes with LPA activity is administered as a monotherapy, while in other preferred embodiments, the composition comprising the agent that interferes with LPA activity is administered as part of a combination therapy. In some cases the effectiveness of the antibody in preventing or treating disease may be improved by administering the antibody serially or in combination with another agent that is effective for those purposes, such as a chemotherapeutic drug for treatment of cancer or a conventional analgesic.

Such other agents may be present in the composition being administered or may be administered separately. Also, the antibody is suitably administered serially or in combination with the other agent or modality.

5. Kits and Articles of Manufacture

In another aspect of the invention, an article of manufacture containing materials useful for the treatment of pain is provided. The article of manufacture or kit comprises a container and a label. Suitable containers include, for example, bottles, vials, syringes, and test tubes. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). The active agent in the composition is the anti-LPA antibody. The label on, or associated with, the container indicates that the composition is used for treating the condition of choice. The article of manufacture may further comprise a second container comprising a pharmaceutically-acceptable buffer, such as phosphate-buffered saline, Ringer's solution and dextrose solution. It may further include other materials desirable from a commercial and user standpoint, including other buffers, diluents, filters, needles, syringes, and package inserts with instructions for use.

The invention will be better understood by reference to the following Examples, which are intended to merely illustrate the best mode now known for practicing the invention. The scope of the invention is not to be considered limited thereto.

EXAMPLES

The invention will be further described by reference to the following detailed examples. These Examples are in no way to be considered to limit the scope of the invention in any manner.

Example 1

Monoclonal Antibodies to LPA

Murine monoclonal antibodies to LPA were made as described in U.S. Patent Application Publication No. 20100034814, which is commonly owned with the instant application and is incorporated herein in its entirety and for all purposes. Six hybridoma clones were selected for characterization based on their superior biochemical and biological properties. Mouse hybridoma cell lines 504B3-6C2, 504B7.1, 504B58/3F8, 504A63.1 and 504B3A6 (corresponding to clones referred to herein as B3, B7, B58, A63, and B3A6, respectively) were received on May 8, 2007 by the American Type Culture Collection (ATCC Patent Depository, 10801 University Blvd., Manassas, Va. 20110) for patent deposit purposes on behalf of LPath Inc. and were granted deposit numbers PTA-8417, PTA-8420, PTA-8418, PTA-8419 and PTA-8416, respectively. All anti-LPA antibodies and portions thereof referred to herein were derived from these cell lines.

Direct Binding Kinetics

The binding of 6 anti-LPA mAbs (B3, B7, B58, A63, B3A6, D22) to 12:0 and 18:1 LPA (0.1 uM) was measured by ELISA. $EC_{50}$ values were calculated from titration curves using 6 increasing concentrations of purified mAbs (0 to 0.4 ug/ml). $EC_{50}$ represents the effective antibody concentration with 50% of the maximum binding. Max denotes the maximal binding (expressed as OD450). Results are shown in Table 1, below.

TABLE 1

Direct Binding Kinetics of Anti-LPA mAbs

| | | B3 | B7 | B58 | D22 | A63 | B3A6 |
|---|---|---|---|---|---|---|---|
| 12:0 LPA | $EC_{50}$ (nM) | 1.420 | 0.413 | 0.554 | 1.307 | 0.280 | 0.344 |
| | Max (OD450) | 1.809 | 1.395 | 1.352 | 0.449 | 1.269 | 1.316 |
| 18:1 LPA | $EC_{50}$ (nM) | 1.067 | 0.274 | 0.245 | 0.176 | 0.298 | 0.469 |
| | Max (OD450) | 1.264 | 0.973 | 0.847 | 0.353 | 1.302 | 1.027 |

The kinetics parameters $k_a$ (association rate constant), $k_d$ (disassociation rate constant) and $K_D$ (association equilibrium constant) were determined for the 6 lead candidates using the BIAcore 3000 Biosensor machine. In this study, LPA was immobilized on the sensor surface and the anti-LPA mAbs were flowed in solution across the surface. As shown, all six mAbs bound LPA with similar $K_D$ values ranging from 0.34 to 3.8 pM and similar kinetic parameters.

The Anti-LPA Murine mAbs Exhibit High Affinity to LPA

LPA was immobilized to the sensor chip at densities ranging 150 resonance units. Dilutions of each mAb were passed over the immobilized LPA and kinetic constants were obtained by nonlinear regression of association/dissociation phases. Errors are given as the standard deviation using at least three determinations in duplicate runs. Results are shown in Table 2, below. Apparent affinities were determined by $K_D=k_a/k_d$.

TABLE 2

Affinity of anti-LPA mAb for LPA

| mAbs | $k_a$ (M$^{-1}$ s$^{-1}$) | $k_d$ (s$^{-1}$) | $K_D$ (pM) |
|---|---|---|---|
| A63 | $4.4 \pm 1.0 \times 10^5$ | $1 \times 10^{-6}$ | $2.3 \pm 0.5$ |
| B3 | $7.0 \pm 1.5 \times 10^5$ | $1 \times 10^{-6}$ | $1.4 \pm 0.3$ |
| B7 | $6.2 \pm 0.1 \times 10^5$ | $1 \times 10^{-6}$ | $1.6 \pm 0.1$ |
| D22 | $3.0 \pm 0.9 \times 10^4$ | $1 \times 10^{-6}$ | $33 \pm 10$ |
| B3A6 | $1.2 \pm 0.9 \times 10^6$ | $1.9 \pm 0.4 \times 10^{-5}$ | $16 \pm 1.2$ |

$k_a$ = Association rate constant in M$^{-1}$s$^{-1}$
$k_d$ = Dissociation rate constant in s$^{-1}$ Specificity Profile of Six Anti-LPA mAbs.

Many isoforms of LPA have been identified to be biologically active and it is preferable that the mAb recognize all of them to some extent to be of therapeutic relevance. The specificity of the anti-LPA mAbs was evaluated utilizing a competition assay in which the competitor lipid was added to the antibody-immobilized lipid mixture.

Competition ELISA assays were performed with the anti-LPA mAbs to assess their specificity. 18:1 LPA was captured on ELISA plates. Each competitor lipid (up to 10 uM) was serially diluted in BSA (1 mg/ml)-PBS and then incubated with the mAbs (3 nM). Mixtures were then transferred to LPA coated wells and the amount of bound antibody was measured with a secondary antibody. Data are normalized to maximum signal ($A_{450}$) and are expressed as percent inhibition. Assays were performed in triplicate. IC$_{50}$: Half maximum inhibition concentration; MI: Maximum inhibition (% of binding in the absence of inhibitor); ---: not estimated because of weak inhibition. A high inhibition result indicates recognition of the competitor lipid by the antibody. As shown in Table 3, below, all the anti-LPA mAbs recognized the different LPA isoforms.

LPA related biolipids such as distearoyl-phosphatidic acid, lysophosphatidylcholine, S1P, ceramide and ceramide-1-phosphate. None of the antibodies demonstrated cross-reactivity to distearoyl PA and LPC, the immediate metabolic precursor of LPA.

Example 2

Cloning of the Murine Anti-LPA Antibodies—Overview

Chimeric antibodies to LPA were generated using the variable domains (Fv) containing the active LPA binding regions of one of three murine antibodies from hybridomas with the Fc region of a human IgG1 immunoglobulin. As those in the art will appreciate, "humanized" antibodies can be generated by grafting the complementarity determining regions (CDRs, e.g. CDR1-4) of the murine anti-LPA mAbs with human antibody framework regions (e.g., Fr1, Fr4, etc.) such as the framework regions of an IgG1.

The overall strategy for cloning of the murine mAb against LPA consisted of cloning the murine variable domains of both the light chain (VL) and the heavy chain (VH) from each antibody. The consensus sequences of the genes show that the constant region fragment is consistent with a gamma isotype and that the light chain is consistent with a kappa isotype. The murine variable domains were cloned together with the constant domain of the human antibody light chain (CL) and with the constant domain of the human heavy chain (CH1, CH2, and CH3), resulting in a chimeric antibody construct. This process and the resulting chimeric antibodies are described in further detail in U.S. Patent Application Publication No. 20100034814, which is commonly owned with the instant application and is incorporated herein in its entirety.

Example 3

Murine Antibody B7

Murine antibody clone B7 has high affinity for the signaling lipid LPA ($K_D$ of 1-50 pM as demonstrated by surface plasmon resonance in the BiaCore assay, and in a direct binding ELISA assay); in addition, B7 demonstrates high specificity for LPA, having shown no binding affinity for over

TABLE 3

Specificity profile of anti-LPA mAbs.

| | 14:0 LPA | | 16:0 LPA | | 18:1 LPA | | 18:2 LPA | | 20:4 LPA | |
|---|---|---|---|---|---|---|---|---|---|---|
| | IC$_{50}$ uM | MI % | IC$_{50}$ uM | MI % | IC$_{50}$ uM | MI % | IC$_{50}$ uM | MI % | IC$_{50}$ uM | MI % |
| B3 | 0.02 | 72.3 | 0.05 | 70.3 | 0.287 | 83 | 0.064 | 72.5 | 0.02 | 67.1 |
| B7 | 0.105 | 61.3 | 0.483 | 62.9 | >2.0 | 100 | 1.487 | 100 | 0.161 | 67 |
| B58 | 0.26 | 63.9 | 5.698 | >100 | 1.5 | 79.3 | 1.240 | 92.6 | 0.304 | 79.8 |
| B104 | 0.32 | 23.1 | 1.557 | 26.5 | 28.648 | >100 | 1.591 | 36 | 0.32 | 20.1 |
| D22 | 0.164 | 34.9 | 0.543 | 31 | 1.489 | 47.7 | 0.331 | 31.4 | 0.164 | 29.5 |
| A63 | 1.147 | 31.9 | 5.994 | 45.7 | — | — | — | — | 0.119 | 14.5 |
| B3A6 | 0.108 | 59.9 | 1.151 | 81.1 | 1.897 | 87.6 | — | — | 0.131 | 44.9 |

Interestingly, the anti-LPA mAbs were able to discriminate between 12:0 (lauroyl), 14:0 (myristoyl), 16:0 (palmitoyl), 18:1 (oleoyl), 18:2 (linoleoyl) and 20:4 (arachidonoyl) LPAs. A desirable EC$_{50}$ rank order for ultimate drug development is 18:2>18:1>20:4 for unsaturated lipids and 14:0>16:0>18:0 for the saturated lipids, along with high specificity. The specificity of the anti-LPA mAbs was assessed for their binding to 100 different bioactive lipids and proteins, including over 20 bioactive lipids, some of which are structurally similar to LPA. The murine antibody is a full-length IgG1k isotype antibody composed of two identical light chains and two identical heavy chains with a total molecular weight of 155.5 kDa. The biophysical properties are summarized in Table 4, below.

TABLE 4

General Properties of Murine antibody B7

| | |
|---|---|
| Identity | B7 (also referred to as LT3000 or Lpathomab) |
| Antibody isotype | Murine IgG1k |
| Specificity | Lysophosphatidic acid (LPA) |
| Molecular weight | 155.5 kDa |
| OD of 1 mg/mL | 1.35 (solution at 280 nm) |
| $K_D$ | 1-50 pM |
| Apparent Tm | 67° C. at pH7.4 |
| Appearance | Clear if dissolved in 1× PBS buffer (6.6 mM phosphate, 154 mM sodium chloride, pH 7.4) |
| Solubility | >40 mg/mL in 6.6 mM phosphate, 154 mM sodium chloride, pH 7.4 |

B7 has also shown biological activity in preliminary cell based assays such as cytokine release, migration and invasion; these are summarized in Table 5, below, along with data showing specificity of B7 for LPA isoforms and other bioactive lipids, and in vitro biological effects.

TABLE 5

LT3000 (B7 antibody)

| A. Competitor Lipid | 14:0 LPA | 16:0 LPA | 18:1 LPA | 18:2 LPA | 20:4 LPA |
|---|---|---|---|---|---|
| $IC_{50}$ (mM) | 0.105 | 0.483 | >2.0 | 1.487 | 0.161 |
| MI (%) | 61.3 | 62.9 | 100 | 100 | 67 |

| B. Competitor Lipid | LPC | S1P | C1P | Cer | DSPA |
|---|---|---|---|---|---|
| MI (%) | 0 | 2.7 | 1.0 | 1 | 0 |

| C. Cell based assay | LPA isoform | % Inhibition (over LPA taken as 100) |
|---|---|---|
| Migration | 18:1 | 35* |
| Invasion | 14:0 | 95* |
| IL-8 Release | 18:1 | 20 |
| IL-6 Release | 18:1 | 23* |
| | | % Induction (over LPA + TAXOL taken as 100) |
| Apoptosis | 18:1 | 79 |

A. Competition ELISA assay was performed with B7 and 5 LPA isoforms. 18:1 LPA was captured on ELISA plates. Each competitor lipid (up to 10 mM) was serially diluted in BSA/PBS and incubated with 3 nM B7. Mixtures were then transferred to LPA coated wells and the amount of bound antibody was measured.
B. Competition ELISA was performed to assess specificity of B7. Data were normalized to maximum signal ($A_{450}$) and were expressed as percent inhibition (n = 3). $IC_{50}$: half maximum inhibition concentration; MI %: maximum inhibition (% of binding in the absence of inhibitor).
C. Migration assay: B7 (150 mg/mL) reduced SKOV3 cell migration triggered by 1 mM LPA (n = 3); Invasion assay: B7 (15 mg/mL) blocked SKOV3 cell invasion triggered by 2 mM LPA (n = 2); Cytokine release of human IL-8 and IL-6: B7 (300-600 mg/mL, respectively) reduced 1 mM LPA-induced release of pro-angiogenic and metastatic IL-8 and IL-6 in SKOV3 conditioned media (n = 3). Apoptosis: SKOV3 cells were treated with 1 mM Taxol; 1 mM LPA blocked Taxol induced caspase-3 activation. The addition to B7 (150 mg/mL) blocked LPA-induced protection from apoptosis (n = 1). Data Analysis: Student-t test, *denotes p < 0.05.

The potent and specific binding of B7/LT3000 to LPA results in reduced availability of extracellular LPA (decrease in effective concentration of LPA) with potentially therapeutic effects.

A second murine anti-LPA antibody, B3, was also subjected to binding analysis as shown in Table 6, below.

TABLE 6

Biochemical characteristics of B3 antibody

| A. BIACORE | High density surface | Low density surface |
|---|---|---|
| Lipid Chip | 12:0 LPA | 18:0 LPA |
| $K_D$ (pM), site 1 (site2) | 61 (32) | 1.6 (0.3) |

| B. Competition Lipid Cocktail ($C_{16}$:$C_{18}$:$C_{18:1}$:$C_{18:2}$:$C_{20:4}$, ratio 3:2:5:11:2) | (µM) |
|---|---|
| $IC_{50}$ | 0.263 |

| C. Neutralization Assay | |
|---|---|
| B3 antibody (nmol) | LPA (nmol) |
| 0 | 0.16 |
| 0.5 | 0.0428 |
| 1 | 0.0148 |
| 2 | under limit of detection |

A. Biacore analysis for B3 antibody. 12:0 and 18:0 isoforms of LPA were immobilized onto GLC sensor chips; solutions of B3 were passed over the chips and sensograms were obtained for both 12:0 and 18:0 LPA chips. Resulted sensograms showed complex binding kinetics of the antibody due to monovalent and bivalent antibody binding capacities. $K_D$ values were calculated approximately for both LPA 12 and LPA 18.
B. Competition ELISA assay was performed with B3 and a cocktail of LPA isoforms ($C_{16}$:$C_{18}$:$C_{18:1}$:$C_{18:2}$:$C_{20:4}$ in ratio 3:2:5:11:2). Competitor/Cocktail lipid (up to 10 µM) was serially diluted in BSA/PBS and incubated with 0.5 µg/mL B3. Mixtures were then transferred to a LPA coated well plate and the amount of bound antibody was measured. Data were normalized to maximum signal ($A_{450}$) and were expressed as $IC_{50}$ (half maximum inhibition concentration).
C. Neutralization assay: Increasing concentrations of B3 were conjugated to a gel. Mouse plasma was then activated to increase endogenous levels of LPA. Activated plasma samples were then incubated with the increasing concentrations of the antibody-gel complex. LPA leftover that did not complex to the antibody was then determined by ELISA. LPA was sponged up by B3 in an antibody concentration dependent way.

Example 4

Humanization of Lpathomab (B7, LT3000)

The variable domains of the murine anti-LPA monoclonal antibody B7 were humanized by grafting the murine CDRs into human framework regions (FR), as fully described in U.S. Patent Application Publication No. 20100034814 and U.S. patent application Ser. No. 12/761,584 and foreign equivalent PCT/US10/31339, which are commonly assigned with the instant application, and the contents of which are incorporated herein in their entirety, with the goal of producing an antibody that retains high affinity, specificity and binding capacity for LPA.

Engineering of the Humanized Variants

The murine anti-LPA antibody was humanized by grafting of the Kabat CDRs from LT3000 $V_H$ and $V_L$ into acceptor human frameworks. Seven humanized variants were transiently expressed in HEK 293 cells in serum-free conditions, purified and then characterized in a panel of assays. Plasmids containing sequences of each light chain and heavy chain were transfected into mammalian cells for production. After 5 days of culture, the mAb titer was determined using quantitative ELISA. All combinations of the heavy and light chains yielded between 2-12 ug of antibody per ml of cell culture.

A three-dimensional (3D) model containing the humanized VL and VH sequences was constructed to identify FR residues juxtaposed to residues that form the CDRs. These FR residues potentially influence the CDR loop structure and the ability of the antibody to retain high affinity and specificity for the antigen. Based on this analysis, 6 residues in AJ002773 and 3 residues in DQ187679 were identified, deemed significantly different from LT3000, and considered for mutation back to the murine sequence. Framework selection and backmutation identification was conducted by DataMabs, LLP, Radlett, Hertfordshire, UK. The role of these back mutations on LPA binding, thermostability and cytokine released were investigated to identify the lead candidate for development of a fully humanized, anti-LPA monoclonal antibody.

Expression of the Humanized Variants

The humanized variants were transiently expressed in HEK 293 cells in serum-free conditions, purified and then characterized in a panel of assays. Plasmids containing sequences of each light chain (pATH500 series) and heavy chain (pATH600 series) were transfected into mammalian cells for production. After 5 days of culture, the mAb titer was determined using quantitative ELISA. All combinations of the heavy and light chains yielded between 2-12 ug of antibody per ml of cell culture. SDS-PAGE under reducing conditions revealed two bands at 25 kDa and 50 kDa with high purity (>98%), consistent with the expected masses of the light and heavy chains. A single band was observed under non-reducing conditions with the expected mass of ~150 KDa.

Characterization of the Humanized Variants

The biophysical properties of the humanized variants were characterized for their binding affinity, binding capacity, yield, potency and stability. All the humanized anti-LPA mAb variants exhibited binding affinity in the low picomolar range similar to the chimeric anti-LPA antibody (also known as LT3010) and the murine antibody (LT3000). All of the humanized variants exhibited a $T_M$ similar to or higher than that of LT3000, and most had a Tm of approximately 71° C. With regard to specificity, the humanized variants demonstrated similar specificity profiles to that of LT3000. For example, LT3000 demonstrated no cross-reactivity to lyso-phosphatidyl choline (LPC), phosphatidic acid (PA), various isoforms of lysophosphatidic acid (14:0 and 18:1 LPA, cyclic phosphatidic acid (cPA), and phosphatidylcholine (PC).

Antibody Expression and Production in Mammalian Cells

The murine antibody genes were cloned from hybridomas. Synthetic genes containing the human framework sequences and the murine CDRs were assembled from synthetic oligonucleotides and cloned into pCR4Blunt-TOPO using blunt restriction sites. After sequencing and observing 100% sequence congruence, the heavy and light chains were cloned and expressed as a full length IgG1 chimeric antibody using the pConGamma vector for the heavy chain gene and pConKappa vector for the light chain gene (Lonza Biologics, Portsmouth N.H.). The expression cassette for each of these genes contained a promoter, a Kozak sequence, and a terminator. These plasmids were transformed into *E. coli* (One Shot Top 10 chemically competent *E. coli* cells, Invitrogen, Cat No. C4040-10), grown in LB media and stocked in glycerol. Large scale plasmid DNA was prepared as described by the manufacturer (Qiagen, endotoxin-free MAXIPREP™ kit, Cat. No 12362). Plasmids were transfected into the human embryonic kidney cell line 293F using 293fectin and using 293F-FreeStyle Media for culture. The transfected cultures expressed approximately 2-12 mg/L of humanized antibody.

Antibody Purification

Monoclonal antibodies were purified from culture supernatants using protein A affinity chromatography. Aliquots containing 0.5 ml of ProSep-vA-Ultra resin (Millipore, Cat. No 115115827) were added to gravity-flow disposable columns (Pierce, Cat. No 29924) and equilibrated with 10-15 ml of binding buffer (Pierce, Cat. No 21001). Culture supernatants containing transiently expressed humanized antibody were diluted 1:1 with binding buffer and passed over the resin. The antibody retained on the column was washed with 15 ml of binding buffer, eluted with low pH elution buffer (Pierce, Cat. No 21004) and collected in 1 ml fractions containing 100 ul of binding buffer to neutralize the pH. Fractions with absorbance (280 nm)>0.1 were dialyzed overnight (Slide-A-Lyzer Cassettes, 3500 MWCO, Pierce, Cat. No 66382) against 1 liter of PBS buffer (Cellgro, Cat. No 021-030). The dialyzed samples were concentrated using centricon-YM50 (Amicon, Cat. No 4225) concentrators and filtered through 0.22 uM cellulose acetate membranes (Costar, Cat. No 8160). The purity of each preparation was accessed using SDS-PAGE.

Quantitative ELISA

The antibody titer was determined using a quantitative ELISA. Goat-anti human IgG-Fc antibody (Bethyl A80-104A, 1 mg/ml) was diluted 1:100 in carbonate buffer (100 mM $NaHCO_3$, 33.6 mM $Na_2CO_3$, pH 9.5). Plates were coated by incubating 100 ul/well of coating solution at 37° C. for 1 hour. The plates were washed 4× with TBS-T (50 mM Tris, 0.14 M NaCl, 0.05% tween-20, pH 8.0) and blocked with 200 ul/well TBS/BSA (50 mM Tris, 0.14 M NaCl, 1% BSA, pH 8.0) for 1 hour at 37° C. Samples and standard were prepared on non-binding plates with enough volume to run in duplicate. The standard was prepared by diluting human reference serum (Bethyl RS10-110; 4 mg/ml) in TBS-T/BSA (50 mM Tris, 0.14 NaCl, 1% BSA, 0.05% Tween-20, pH 8.0) to the following concentrations: 500 ng/ml, 250 ng/ml, 125 ng/ml, 62.5 ng/ml, 31.25 ng/ml, 15.625 ng/ml, 7.8125 ng/ml, and 0.0 ng/ml. Samples were prepared by making appropriate dilutions in TBS-T/BSA, such that the optical density (OD) of the samples fell within the range of the standard; the most linear range being from 125 ng/ml 15.625 ng/ml. After washing the plates 4× with TBS-T, 100 ul of the standard/samples preparation was added to each well and incubated at 37° C. for 1 hour. Next the plates were washed 4× with TBS-T and incubated for 1 hour at 37° C. with 100 ul/well of HRP-goat anti-human IgG antibody (Bethyl A80-104P, 1 mg/ml) diluted 1:150,000 in TBS-T/BSA. The plates were washed 4× with TBS-T and developed using 100 ul/well of TMB substrate chilled to 4° C. After 7 minutes, the reaction was stopped with 1M $H_2SO_4$ (100 ul/well). The OD was measured at 450 nm, and the data was analyzed using Graphpad Prizm software. The standard curve was fit using a four parameter equation and used to calculate the human IgG content in the samples.

Direct Binding ELISA

The LPA-binding affinities of the humanized antibodies were determined using a direct binding ELISA assay. Microtiter ELISA plates (Costar) were coated overnight with 1.0 ug/ml C12:0 LPA conjugated to Imject maleimide activated bovine serum albumin (BSA) (Pierce Co.) diluted in 0.1 M carbonate buffer (pH 9.5) at 37° C. for 1 h. Plates were washed with PBS (137 mM NaCl, 2.68 mM KCl, 10.1 mM $Na_2HPO_4$, 1.76 mM $KH_2PO_4$; pH 7.4) and blocked with PBS/BSA/tween-20 for 1 hr at room temp or overnight at 4° C. For the primary incubation (1 hr at room temperature), a dilution series of the anti-LPA antibodies (0.4 ug/mL, 0.2 ug/mL, 0.1 ug/mL, 0.05 ug/mL, 0.0125 ug/mL, and 0 ug/mL) was added to the microplate (100 ml per well). Plates were washed and incubated with 100 ul per well of HRP conjugated goat anti-human (H+L) diluted 1:20,000 (Jackson, cat#109-035-003) for 1 hr at room temperature. After washing, the peroxidase was developed with tetramethylbenzidine substrate (Sigma, cat No T0440) and stopped by adding 1 M $H_2SO_4$. The optical density (OD) was measured at 450 nm using a Thermo Multiskan EX. The $EC_{50}$ (half-maximal binding concentration) was determined by a least-squares fit of the dose-response curves with a four parameter equation using the Graphpad Prism software.

The $EC_{50}$ of the humanized antibody, LT3015, was determined to be 75.6 ng/mL, as compared to the murine antibody, LT3000, which had an $EC_{50}$ of 65.3 ng/mL.

LPA Competition ELISA

The specificity of the humanized antibody was determined by competition ELISA. C18:0 LPA coating material was diluted to 0.33 ug/ml with carbonate buffer (100 mM NaHCO3, 33.6 mM Na2CO3, pH 9.5). Plates were coated with 100 ul/well of coating solution and incubated at 37° C. for 1 hour. The plates were washed 4 times with PBS (100 mM Na2HPO4, 20 mM KH2PO4, 27 mM KCl, 1.37 mM NaCl, pH 7.4) and blocked with 150 ul/well of PBS, 1% BSA, 0.1% tween-20 for 1 h at room temperature. The humanized, anti-LPA antibodies were tested against lipid competitors (14:0 LPA (Avanti, Cat. No 857120), 18:1 LPA (Avanti, Cat. No 857130), 18:1 LPC (Avanti, Cat. No 845875), cLPA (Avanti, Cat. No 857328), 18:1 PA (Avanti, Cat. No 840875), PC (Avanti, Cat. No 850454) at 5 uM, 2.5 uM, 1.25 uM, 0.625 uM, and 0.0 uM. The antibody was diluted to 0.5 ug/ml in PBS, 0.1% tween-20 and combined with the lipid samples at a 1:3 ratio of antibody to sample on a non-binding plate. The plates were washed 4 times with PBS and incubated for 1 hour at room temperature with 100 ul/well of the primary antibody/lipid complex. Next the plates were washed 4 times with PBS and incubated for 1 h at room temperature with 100 ul/well of HRP-conjugated goat anti-human antibody diluted 1:20,000 in PBS, 1% BSA, 0.1% tween-20. Again the plates were washed 4 times with PBS and developed using TMB substrate (100 ul/well) at 4° C. After 8 minutes, the reaction was stopped with 100 ul/well of 1M H2SO4. The optical density (OD) was measured at 450 nm using a Thermo Multiskan EX. Raw data were transferred to GraphPad software for analysis.

The $IC_{50}$ for the humanized mAb LT3015 was determined to be 0.08 uM, whereas the $IC_{50}$ for the corresponding murine antibody, LT3000, was 0.28 uM.

Thermostability

The thermostability of the humanized antibodies was studied by measuring their LPA-binding affinity ($EC_{50}$) after heating using the direct binding ELISA. Antibodies dissolved in PBS (Cellgo, Cat. No 021-040) were diluted to 25 ug/ml and incubated at 60° C., 65° C., 70° C., 75° C. and 80° C. for 10 min. Prior to increasing the temperature, 10 ul of each sample was removed and diluted with 90 ul of PBS and stored on ice. The samples were then vortexed briefly and the insoluble material was removed by centrifugation for 1 min at 13,000 rpm. The binding activity of the supernatant was determined using the direct LPA-binding ELISA and compared to a control, which consisted of the same sample without heat treatment.

The Tm for the humanized antibody, LT3015, was determined to be 71.5° C., higher than that of the murine parent antibody, LT3000, which had a Tm of 67° C.

Surface Plasmon Resonance

All binding data were collected on a ProteOn optical biosensor (BioRad, Hercules Calif.). 12:0 LPA-thiol and 18:0 LPA-thiol were coupled to a maleimide modified GLC sensor chip (Cat. No 176-5011). First, the GLC chip was activated with an equal mixture of sulfo-NHS/EDC for seven minutes followed by a 7 minute blocking step with ethyldiamine. Next sulfo-MBS (Pierce Co., cat #22312) was passed over the surfaces at a concentration of 0.5 mM in HBS running buffer (10 mM HEPES, 150 mM NaCl, 0.005% tween-20, pH 7.4). LPA-thiol was diluted into the HBS running buffer to a concentration of 10, 1 and 0.1 uM and injected for 7 minutes producing 3 different density LPA surfaces (~100, ~300 and ~1400 RU). Next, binding data for the humanized antibodies was collected using a 3-fold dilution series starting with 25 nM as the highest concentration (original stocks were each diluted 1 to 100). Surfaces were regenerated with a 10 second pulse of 100 mM HCl. All data were collected at 25° C. Controls were processed using a reference surface as well as blank injections. The response data from each surface showed complex binding behavior which a likely caused by various degrees of multivalent binding. In order to extract estimates of the binding constants, data from the varying antibody concentrations were globally fit using 1-site and 2-site models. This produced estimates of the affinity for the bivalent (site 1) and monovalent site (site 2).

LPA Molar Binding Capacity

The molar ratio of LPA:mAb was determined using a displacement assay. Borosilicate tubes (Fisherbrand, Cat. No 14-961-26) were coated with 5 nanomoles of biotinylated LPA (50 ug of lipid (Echelon Biosciences, Cat. No L-012B, Lot No F-66-136 were suspended in 705 ul of 1:1 chloroform: methanol yielding a 100 uM solution) using a dry nitrogen stream. The coated tubes were incubated with 75 ul (125 pmoles) of antibody dissolved in PBS (Cellgro, Cat. No 021-030) at room temperature. After 3 hours of incubation, the LPA:mAb complexes were separated from free lipid using protein desalting columns (Pierce, Cat, No 89849), and the molar concentration of bound biotinylated LPA was determined using the HABA/Avidin displacement assay (Pierce, Cat. No 28010) according to the manufacturer's instructions.

Measurement of LPA-Induced IL-6 and IL-8 Release in SKOV3 Cells

Anti-LPA antibodies inhibit the LPA-dependant release of human CXCL8/IL-8 in conditioned media of SKOV3 ovarian cells, indicating that these antibodies are biologically active. SKOV3 cells (Lot No 4255558, passage 14) were harvested with 2 ml of 1× Trypsin EDTA (Mediatech Inc, Cat. No 25-053-CV) and resuspended in 8 ml of complete medium (10% FBS, Mediatech Inc. Cat. no 35-011-CV). The cells were centrifuged for 5 min (11,000 rpm) and re-suspended in 5 ml of complete medium. Cells were counted in duplicate with 0.4% Trypan blue (10 ul cells plus 90 ul Trypan blue, Invitrogen, Cat. No 15250-061) using a hemocytometer. In a 96-well plate, $1 \times 10^5$ cells per well were seeded (final volume 100 ul/well). The cells were allowed to attach and form a confluent monolayer by incubating overnight at 37° C. On the following day, cells were gently washed two times with minimum media (1 mg/ml BSA in McCoy's medium with L-glutamine, Mediatech, Cat. No 10-050-CV). The media was adjusted to 1% penicillin/streptomycin (Mediatech, Cat. No 30-002 CI) and 2.2 g/L sodium-bicarbonate (Mediatech, Cat. No 25-035-CI). Next, the cells were serum-starved at 37° C. for exactly 24 h, followed by cytokine stimulation with 1 uM C18:1 LPA (Avanti, Cat. No 857130) dissolved in 1 mg/ml BSA/PBS (Calbiochem, Cat. No 126575) which was pre-incubated in presence or absence of humanized LPA antibody LT3015 (150, 300 or 600 ug/mL) for one hour. Treatments were then added to the cells. After 22 h of cytokine stimulation, the cells were centrifuged for 5 min (13,500 rpm) at 4° C. and the supernatants (cell-conditioned media) were collected. The CXCL8/IL-8 levels in each supernatant were measured using the Quantikine human CXCL8/IL-8 ELISA kit according to vendor instructions (R&D Systems, Minneapolis Minn., Cat. No D8000C). The IL-6 levels were measured by ELISA using the Quantikine human IL-6 immunoassay kit (R&D systems, Cat. No. D6050). Data were analyzed by one-way ANOVA followed by Bonferroni's post test and expressed as human IL-8 or human IL-6 fold increase. Data are shown in Table 7 and Table 8 below.

TABLE 7

Inhibition of human IL-8 release by humanized anti-LPA antibody LT3015

| Stimulus condition | Human IL-8 Fold Increase (approx). |
|---|---|
| NT (no treatment) | 1 |
| 1 uM LPA | 7.1## |
| LPA + LT3015, 150 ug/mL | 5.7 |
| LPA + LT3015, 300 ug/mL | 4.5** |
| LPA + LT3015, 600 ug/mL | 2.7** |
| LT3015, 300 ug/mL | 1.1 |
| FBS (10%) | 20.1 |

(*p < 0.05, **p < 0.001 and ##p < 0.001, n = 3)

TABLE 8

Inhibition of human IL-6 release by humanized anti-LPA antibody LT3015

| Stimulus condition | Human IL-6 Fold Increase (approx). |
|---|---|
| NT (no treatment) | 1 |
| 1 uM LPA | 29## |
| LPA + LT3015, 150 ug/mL | 22.1 |
| LPA + LT3015, 300 ug/mL | 15.7* |
| LPA + LT3015, 600 ug/mL | 10.8** |
| LT3015, 300 ug/mL | 1.1 |
| FBS (10%) | 69.2 |

(*p < 0.05, **p < 0.001 and ##p < 0.001, n = 3)

Activity of LT3015 in Disease Models:

LT3015 was shown to prevention of ovarian tumor cell migration in the scratch assay, and further was shown to reduce ovarian tumor SKOV3 progression and circulating cytokines in biological fluids of mice. For further details see U.S. application Ser. No. 12/761,584, filed 16 Apr. 2010, which is commonly owned with the instant invention and is incorporated herein by reference in its entirety.

Example 5

Creation of the Vector pATH3015 for Cell Line Development

LT3015 is a recombinant, humanized, monoclonal antibody that binds with high affinity to the bioactive lipid lysophosphatidic acid (LPA). LT3015 is a full-length IgG1k isotype antibody composed of two identical light chains and two identical heavy chains with a total molecular weight of 150 kDa. The heavy chain contains an N-linked glycosylation site. The two heavy chains are covalently coupled to each other through two intermolecular disulfide bonds, consistent with the structure of a human IgG1.

LT3015 was originally derived from a murine monoclonal antibody which was produced using hybridomas generated from mice immunized with LPA. The humanization of the murine antibody involved the insertion of the six murine complementarity determining regions (CDRs) in place of those of a human antibody framework selected for its structure similarity to the murine parent antibody. A series of substitutions were made in the framework to engineer the humanized antibody. These substitutions are called back mutations and replace human with murine residues that are involved in the interaction with the antigen. The final humanized version contains six murine back mutation in the human framework of variable domain of the heavy chain (pATH602) and three murine back mutations in the human framework of the variable domain of the light chain (pATH502).

The variable domains of the humanized anti-LPA monoclonal antibody were cloned into the vector IgG1k of the Lonza Biologics' GS gene expression system to generate the vector pATH3015. This expression system consists of an expression vector carrying the constant domains of the antibody genes and the selectable marker glutamine synthetase (GS). GS is the enzyme responsible for the biosynthesis of glutamine from glutamate and ammonia. The vector carrying both the antibody genes and the selectable marker were transfected into the Chinese Hamster Ovary (CHOK1SV) cell line providing sufficient glutamine for the cells to survive without exogenous glutamine. In addition, the specific GS inhibitor, methionine sulphoximine (MSX) was supplemented in the medium to inhibit endogenous GS activity such that only the cell lines with GS activity provided by the vector could survive. The transfected cells were selected for their ability to grow in glutamine-free medium in the presence of MSX.

Further details of the cloning steps of the variable domains of the humanized anti-LPA monoclonal antibody into the double gene vector IgG1κ of the Lonza Biologic's GS gene expression system to generate pATH3015 may be found in U.S. application Ser. No. 12/761,584, filed 16 Apr. 2010, which is commonly owned with the instant application and is incorporated herein by reference in its entirety.

pATH3015 was introduced by electroporation into the Lonza proprietary Chinese Hamster Ovary (CHOK1SV) host cell line adapted for growth in serum-free medium. The cell line derived from this transfection is designated LH2 and is used to produce drug substance. The expressed drug LT3015 has the following characteristics:

TABLE 9

| Characteristics of LT3015 | |
|---|---|
| Drug Substance | LT3015 |
| DNA | pATH3015 |
| Isotype | IgG1κ |
| Molecular Substitutions | 6 murine back mutation in the heavy chain |
|  | 3 murine back mutations in the light chain |
| Specificity | LPA |
| Expression System | Lonza Biologics' GS gene expression system |
| Potency | in vitro and in vivo potency |

Example 6

Humanized Anti-LPA Variable Region Sequences

Additional humanized anti-LPA variants of murine antibody B7 and murine antibody B3 heavy chains and of the B3 heavy chain were generated as described above.

pATH3016 was produced similarly to pATH3015. As described above, the heavy chains of pATH3015 and 3016 are identical (derived from pATH602, having six backmutations), but pATH3016 light chain (derived from pATH506) contains fewer backmutations. The humanized monoclonal antibody produced from pATH3016 is LT3016. Both pATH3015 and pATH3016 were deposited with the American Type Culture Collection (Manassas Va.) and have ATCC Patent Deposit Designations PTA-9219 and PTA-9220, respectively.

Activity of the Humanized Variants

Five humanized variants (LT3011, LT3013, LT3014, LT3015 and LT3016) were further assessed in in vitro cell assays. LPA is known to play an important role in eliciting the release of interleukin-8 (IL-8) from cancer cells. LT3000 reduced IL-8 release from ovarian cancer cells in a concentration-dependent manner. The humanized variants exhibited a similar reduction of IL-8 release compared to LT3000.

Some humanized variants were also tested for their effect on microvessel density (MVD) in a Matrigel tube formation assay for neovascularization. Both were shown to decrease MVD formation.

TABLE 10

Quantitation of microblood vessel density using CD31 immunostain with H&E counterstaining in matrigel plugs.

|  | Control | LT3000 murine (8 mg/kg) | LT3000 murine (2 mg/kg) | Humanized variant #1 (LT3015) (8 mg/kg) | Humanized variant #1 (LT3015) (2 mg/kg) | Humanized variant #2 (LT3016) (2 mg/kg) |
|---|---|---|---|---|---|---|
| Average | 64.2 | 41.5 | 34 | 34.4 | 49 | 50.8 |
| S.E. | 8.0 | 14.2 | 13.7 | 4.2 | 31.5 | 18.8 |
| N = | 5 | 4 | 5 | 5 | 5 | 6 |
| Percent Inhibition |  | 35.4 | 47.0 | 46.4 | 23.7 | 20.8 |

Humanized anti-LPA antibody LT3015 (also referred to as "Lpathomab") was chosen for further characterization. The humanized mAb retains the binding, specificity and thermostability of the murine parent antibody, B7.

Another humanized anti-LPA variant, LT3114, was also chosen for further characterization and comparison with LT3015. LT3114 was humanized based on the murine monoclonal antibody B3.

For convenience, a comparison of the variants of B7 (light and heavy chains and combinations thereof) is shown in Table 11 and a comparison of the variants of B3 is shown in Table 12.

TABLE 11

Chimeric and humanized LPA variants of B7

| mAb name | Light Chain | | Heavy Chain | |
|---|---|---|---|---|
|  | pATH | Back mutations | pATH | Back mutations |
| LT3010 B7 chimeric | 510 | none | 610 | None |
| LT3011 | 502 | I2V, Q45K, Y87F | 603 | S24A, I28G, M48I |
| LT3012 | 502 | I2V, Q45K, Y87F | 604 | I28G, M48I, V67A, I69L |
| LT3013 | 506 | I2V | 603 | S24A, I28G, M48I |
| LT3014 | 506 | I2V | 604 | I28G, M48I, V67A, I69L |
| LT3015 | 502 | I2V, Q45K, Y87F | 602 | S24A, I28G, V37I, M48I, V67A, I69L |
| LT3016 | 506 | I2V | 602 | S24A, I28G, V37I, M48I, V67A, I69L |

TABLE 12

Chimeric and humanized LPA variants of B3 light and heavy chains

| mAb name | Light Chain | | Heavy Chain | |
|---|---|---|---|---|
|  | pATH | Back mutations | pATH | Back mutations |
| B3 chimeric |  | none |  | None |
|  | 700 | I2V, T24R, G26S, V27cL, H27dK, I27eT, Q45K, L54R, Y87F |  |  |
|  | 701 | I2V, T24R, G26S, V27cL, H27dK, I27eT, L54R |  |  |
|  | 702 | I2V, T24R, G26S, V27cL, H27dK, I27eT, Q45K, Y49F, L54R, Y87F |  |  |
|  |  |  | 800 | S24A, I28G, V37I, M48I, N52Y, G53D, D55G, T57I, V67A, I69L, G97A, N100cY |
|  |  |  | 801 | S24A, I28A, I30T, N52Y, G53D, D55G, T57I, G97A, N100cY |
|  |  |  | 802 | S24A, I28A, I30T, M48I, N52Y, G53D, D55G, T57I, V67A, I69L, G97A, N100cY |
|  |  |  | 803 | S24A, Y27D, I28A, I30T, N52Y, G53D, D55G, T57I, K73R, G97A, N100cY |
|  |  |  | 804 | S24A, Y27D, I28A, I30T, M48I, N52Y, G53D, D55G, T57I, V67A, I69L, K73R, G97A, N100cY |
| LT3114 Humanized antibody variant | 702 | I2V, T24R, G26S, V27cL, H27dK, I27eT, Q45K, Y49F, L54R, Y87F | 804 | S24A, Y27D, I28A, I30T, M48I, N52Y, G53D, D55G, T57I, V67A, I69L, K73R, G97A, N100cY |

Development and Characterization of LT3114 and LT3015:

Lpathomab was humanized with the goal of producing a humanized antibody that retains high affinity and specificity for binding LPA. Humanization of the murine antibody was achieved by replacing the six complimentarily determining regions (CDRs) of the IgGk1 heavy and light variable domains of selected human antibody frameworks with the Kabat-defined CDRs from the murine anti-LPA mAb, Lpathomab. A series of back mutations were made in the frameworks to maximize the interaction of the humanized antibody with the antigen. Several humanized variants were engineered and expressed in mammalian cells and were shown to bind LPA very similarly to the murine Lpathomab. The humanized variants were characterized for their binding affinity for LPA and their cross-reactivity to related lipids. Specificity of the humanized anti-LPA antibodies, LT3015, LT3114 and murine mAb, B3, was measured in an ELISA-based competition binding assay. Briefly, the antibodies were captured on ELISA plates precoated with goat-anti-human or mouse IgG. A series of dilutions of the competing lipid were allowed to bind in the presence of a fixed amount of biotin-labeled 18:0 LPA. Bound labeled LPA was then detected using streptavidin conjugated to horseradish peroxidase.

Figure 1B:
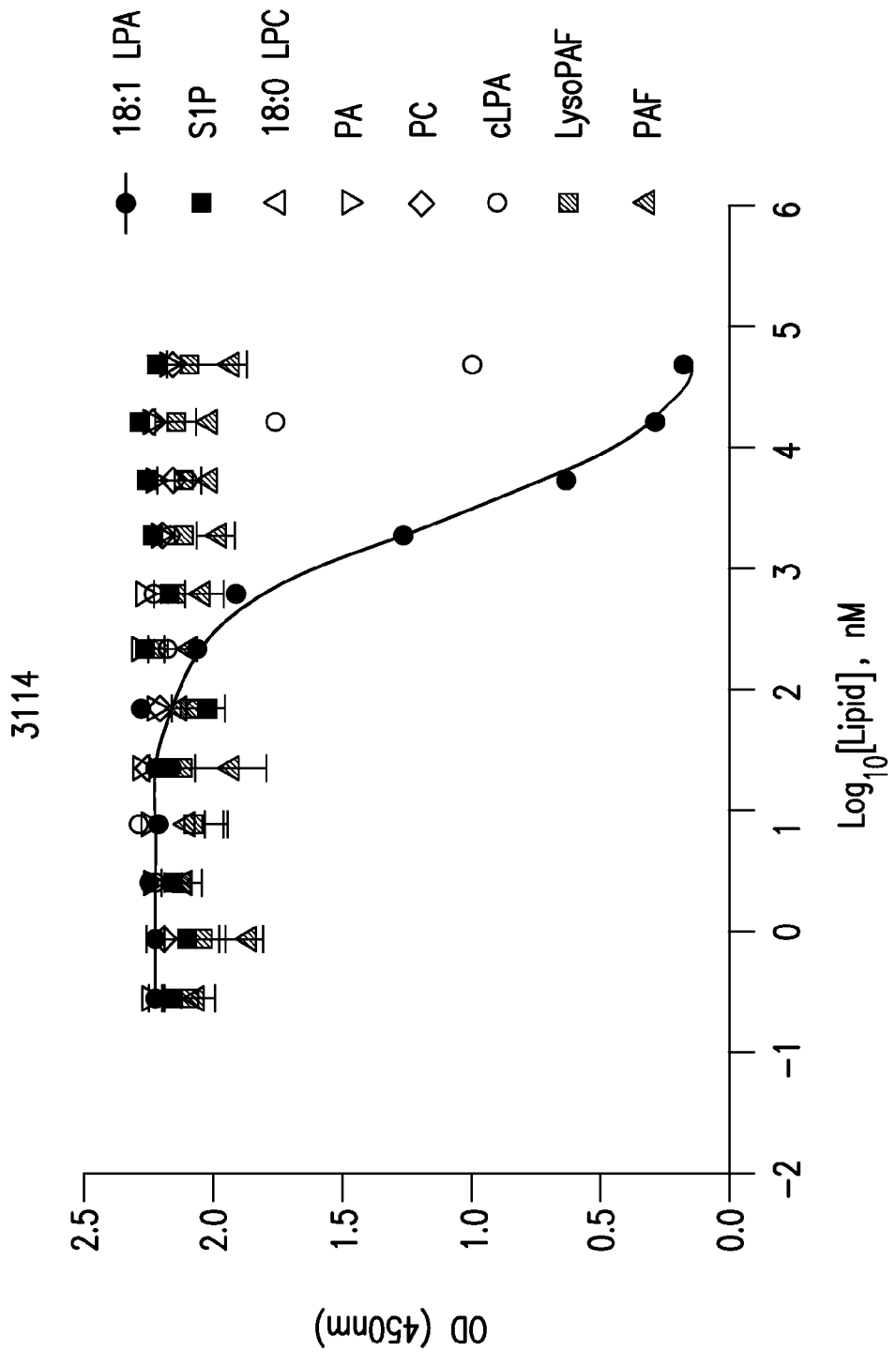
Figure 1C:
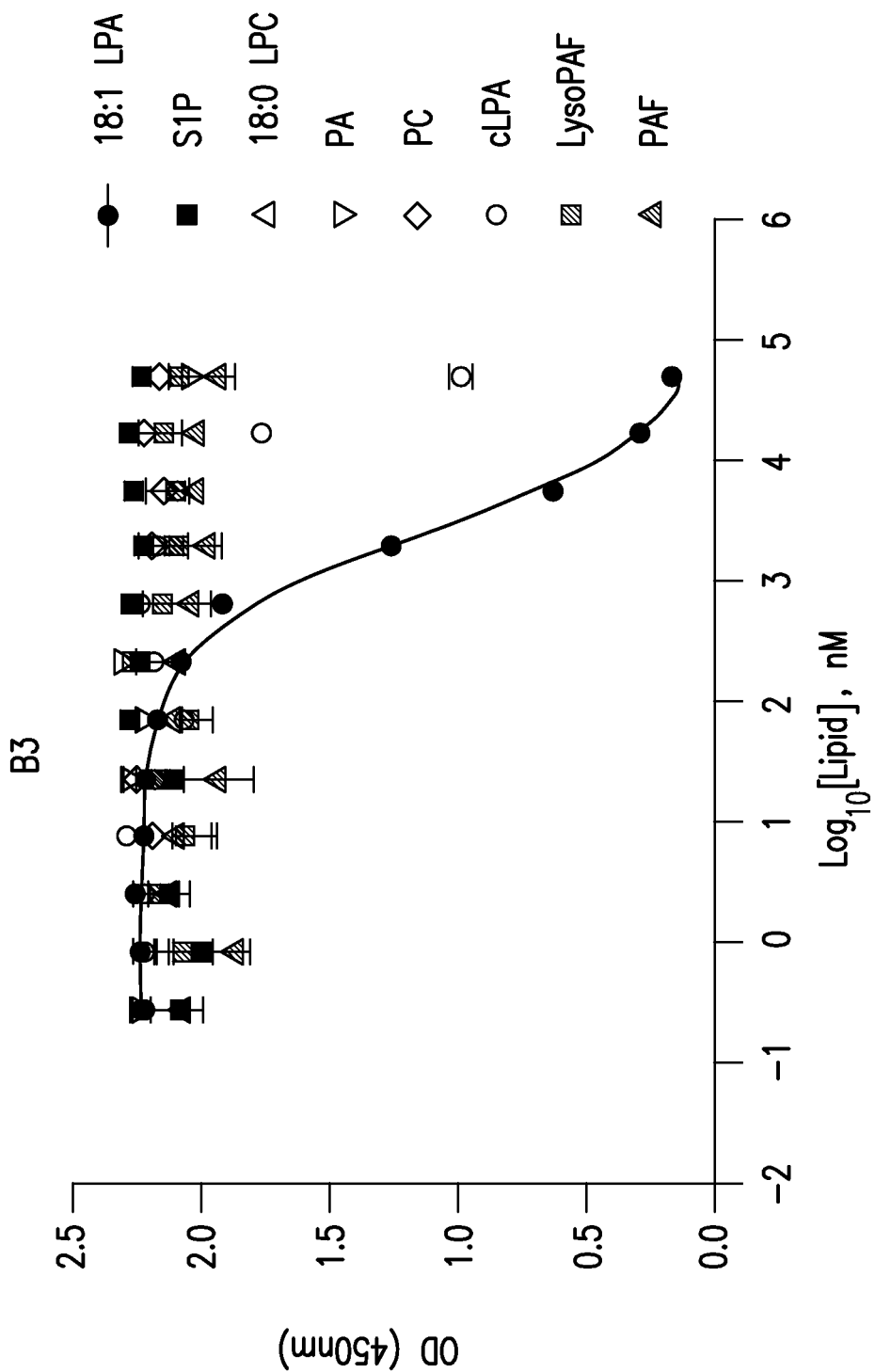

With regard to specificity, the humanized variants demonstrated similar specificity profiles to that of Lpathomab including no cross-reactivity to LPC, PA, PC, platelet activating factor (PAF) or lyso-PAF and minimal cross-reactivity with cyclic LPA (cLPA) by competition ELISA (FIG. 1).

Figure 2A:
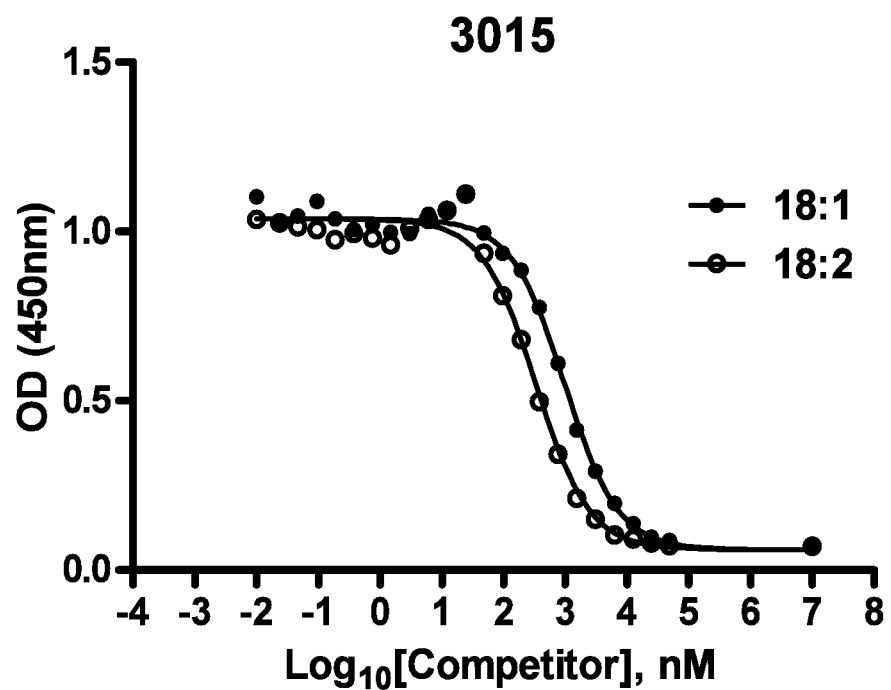
FIGS. 2a, 2b and 2c are line graphs showing the binding affinities of the humanized anti-LPA antibodies, LT3015, LT3114 and the murine anti-LPA mAb, B3, respectively, for various LPA isoforms, as measured in an ELISA-based competition binding assay.
Figure 2B:
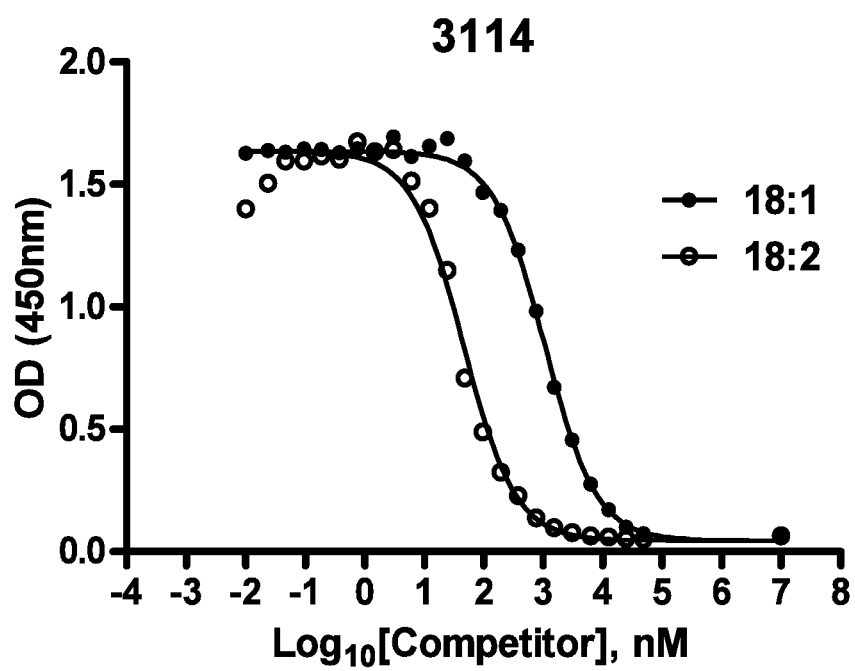
Figure 2C:
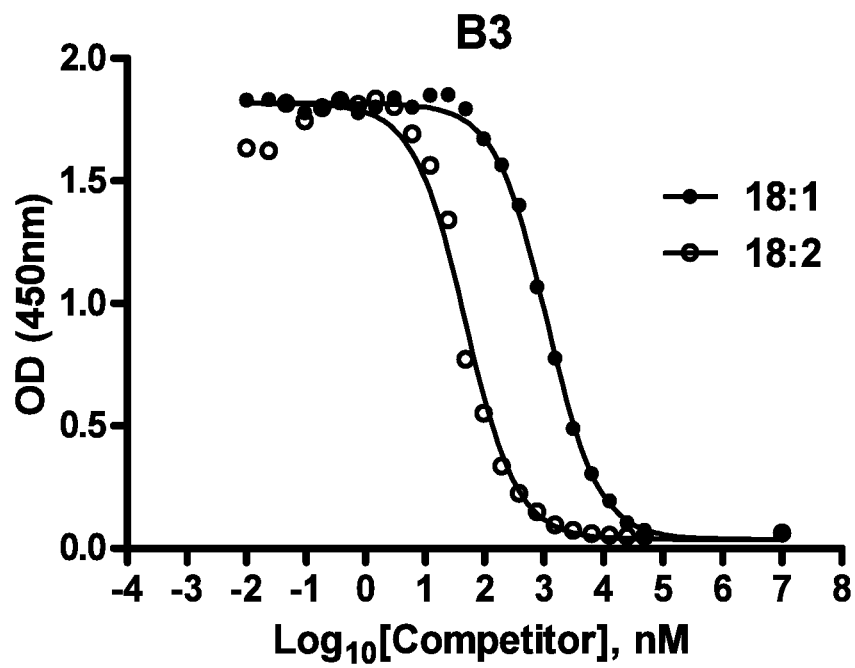

The competition binding ELISA was also used to compare the affinity of the different antibodies for different isoforms of LPA. Affinities of the antibodies for native 18:1 and 18:2 LPA were measured in an ELISA-based competition binding assay. Briefly, the antibodies were captured on ELISA plates precoated with goat-anti-human or mouse IgG. A series of dilutions of the native lipid were allowed to bind in the presence of a fixed amount of biotin-labeled 18:0 LPA. Bound labeled LPA was then detected using streptavidin conjugated to horseradish peroxidase. The Ki for each antibody binding to the native lipids was determined by fitting the competition binding data using the formula of Cheng and Prusoff in GraphPad Prism software and the Kd of each antibody for the biotin-labeled LPA determined in a separate saturation binding ELISA experiment. Representative data for the two humanized antibody candidates, LT3114 and LT3015, and the original murine anti-LPA antibody (designated B3) are shown in FIG. 2. These data show the competition binding curves for 18:1 and 18:2 LPA. The humanized antibody variant, LT3114, and the murine antibody, B3, from which the LT3114 CDRs were obtained, have essentially identical binding characteristics for native lipid, with a Ki of 15 nM for 18:2 LPA and 360 nM for 18:1 LPA. The Ki of the LT3015 humanized antibody variant for the two LPA isoforms is somewhat lower at 200 nM for 18:2 and 600 nM for 18:1 LPA. Binding to the 16:0, 18:0 and 20:4 LPA isoforms was also examined. In each case, the binding by humanized antibody LT3114 was identical to that attained with the original murine B3 antibody.

2. Humanized Anti-LPA Antibodies LT3114 and LT3015 Inhibit the Biological Activity of LPA.

It has been demonstrated that Lpathomab is able to block the binding of LPA to the LPA1 receptor and prevent cellular activation. The abilities of the humanized mAbs, LT3114 and LT3015, to block the stimulation by LPA in LPA1 overexpressing cells were tested. Increasing concentrations (0-1,500 µg/mL) of murine antibody B3 and humanized antibodies LT3114 and LT3015 were added together with 18:0, 18:1, 18:2 or 20:4 LPA to LPA1 receptor transfected cells and tested for their abilities to block receptor signaling. All three antibodies effectively inhibited LPA1 receptor signaling in response to each lipid tested.

Example 7

Preliminary Animal Pharmacokinetics of Lpathomab

Preliminary PK studies were conducted with Lpathomab. For IV dosed groups, mice were injected with a single 30 mg/kg dose and sacrificed at time points up to 15 days. Antibody was also given via i.p. administration and animals were sacrificed during the first 24 hrs to compare levels of mAb in the blood over this period of time for different routes of delivery. Pharmacokinetic parameters were assessed by Win-Nonlin. Three mice were sacrificed at each time point and plasma samples were collected and analyzed for mAb levels by ELISA. The half-life of Lpathomab in mice was determined to be 102 hrs (4.25 days) by i.v. administration. Moreover, the antibody is fully distributed to the blood within 6-12 hrs when given i.p., suggesting that the i.p. administration is suitable.

TABLE 13

Pharmacokinetic profile of Lpathomab in mice
Pharmacokinetic Parameters

| Group | Treatment (mg/kg) | Route | | Estimate | SD | CV % |
|---|---|---|---|---|---|---|
| 1 | 30 | IV | AUC | 88.35 | 60.23 | 68.18 |
| | | | K10-HL | 102.7 | 77.48 | 75.91 |
| | | | Cmax | 0.6 | 0.13 | 21.71 |
| | | | Cl | 0.34 | 0.23 | 68.24 |
| | | | AUMC | 13009.8 | 18549.2 | 142.58 |
| | | | MRT | 147.25 | 111.78 | 75.91 |
| | | | Vss | 50 | 10.86 | 21.73 |

Software used to calculate the parameters: WinNonlin v1.1
AUC           Area under the curve
K10-HL       Elimination half-life
Cmax          Dose related peak value
Cl               Clearance
AUMC        Area under the first moment curve
MRT           Mean residence time
Vss             Apparent volume of distribution, steady state Example 8

Anti-LPA mAB Inhibits LPA-Induced IL-6 Release

IL-6 is a potent pain-generating inflammatory mediator. IL-6 is produced in the rat spinal cord following peripheral nerve injury, with levels of IL-6 levels correlating directly with the intensity of allodynia. Arruda, et al. (2000), Brain Res. 879:216-25. IL-6 levels increase during stress or inflammation, and rheumatoid arthritis is associated with increased levels of IL-6 in synovial fluid. Matsumoto, et al (2006), Rheumatol. Int. 26:1096-1100; Desgeorges, et al. (1997), J. Rheumatol. 24:1510-1516. Neuropathic pain is prevented in IL-6 knockout mice. Xu, et al (1997) Cytokine 9:1028-1033. In primary astrocytes, treatment with LPA (1 uM) causes IL-6 release. An experiment was conducted to evaluate the effect of anti-LPA antibody on IL-6 release in primary astrocytes.

Rat primary astrocytes were purchased from Cambrex (Charles City, Iowa) and cultured following vendor instructions. For IL-6 release assay, cells were seeded in a 96-well plate at the density of 1×104 cells per well and serum starved in media without serum for 24 hrs. After serum-starvation, primary astrocytes were treated with 1 mM LPA (solubilized in 1 mg/mL fatty acid-free BSA in PBS) previously incubated in the presence or absence of murine anti-LPA monoclonal antibody B3 (150 or 300 mg/mL antibody (1:1 or 1:2 molar ratio mAb:LPA; 1 hr at 37° C. in 5% CO2 humidified incubator). After 24 hr, conditioned media were collected and tested by human IL-6 ELISA (Rat IL-6 Quantikine Kit, R&D systems, Minneapolis Minn.) following vendor instructions. IL-6 values (pg/ml) were calculated using GraphPad software (La Jolla, Calif.).

Cell conditioned media from human primary astrocytes were tested for IL-6 levels after 24 hrs of incubation with 1 mM LPA in presence or absence of molar ratio concentrations of B3 antibody (1:1 or 1:2 mAb:LPA). Treatment with LPA plus antibody to LPA (murine antibody B3) at a ratio of 2:1 not only blocked the IL-6 release but lowered IL-6 levels to approximately half the control level. LPA plus antibody at a ratio of 1:1 caused nearly as great a reduction in IL-6 levels. Thus anti-LPA antibody blocks the release of IL-6 that occurs in response to astrocyte treatment with LPA.

Example 9

Antibody to LPA Reduces Allodynia in Diabetes-Induced Neuropathic Pain Model

Studies were performed in the rat model of streptozotocin-induced type 1 (insulin deficient) diabetes using tactile allodynia and hyperalgesia during the formalin test as behavioral indices of diabetes-induced neuropathic pain. All experimental procedures have been published. Calcutt N A, Freshwater J D, O'Brien J S (2000), Anesthesiology 93:1271-1278; Jolivalt C G, Ramos K M, Herbetsson K, Esch F S, Calcutt N A (2006), Pain 121:14-21.

Female Sprague-Dawley rats (Harlan Industries, San Diego Calif.) weighing 225-250 grams each were maintained at room temperature, between 65 to 82° F. with relative humidity between 30 to 70%. The room was illuminated with fluorescent lighting on a daily 12 hour light/dark cycle. All animals were maintained 2/cage with free access to dry food and municipal water.

Insulin deficient diabetes was induced following an overnight fast by a single IP injection of streptozotocin (55 mg/kg) dissolved in 0.9% sterile saline. Hyperglycemia was confirmed 4 days later and also prior to behavioral testing in a sample of blood obtained by tail prick using a strip operated reflectance meter. All animals were observed daily and weighed regularly during the study period.

Tactile Response Threshold:

Rats were transferred to a testing cage with a wire mesh bottom and allowed to acclimate. Von Frey filaments (Stoelting, Wood Dale Ill.) were used to determine the 50% mechanical threshold for foot withdrawal. A series of filaments, starting with one possessing a buckling weight of 2.0 g, were applied in sequence to the plantar surface of the right hindpaw with a pressure that causes the filament to buckle. Lifting of the paw was recorded as a positive response and the next lightest filament chosen for the next measurement. Absence of a response after 5 seconds prompted use of the next filament of increasing weight. This paradigm was continued until four measurements were made after an initial change in the behavior or until five consecutive negative (given the score of 15 g) or four positive (score of 0.25 g) scores occurred. The resulting sequence of positive and negative scores was used to interpolate the 50% response threshold. Only rats with a 50% tactile response threshold below 6 g were considered allodynic and brought forward for drug testing.

Formalin Test:

Rats were restrained manually and formalin (50 µl of 0.2% or 0.5% solution) injected sub-dermally into the hindpaw dorsum. Rats were then placed in an observation chamber and flinching behaviors counted in 1-minute blocks every 5 minutes for 1 hour.

Tissue Collection:

Blood was removed from restrained rats by tail prick to confirm hyperglycemia in diabetic rats using a strip-operated reflectance meter. Blood (0.3-0.5 ml per sample) can also be drawn into heparin-coated tubes on ice, centrifuged (1500 g, 2° C., 10 minutes), and plasma stored at −70° C. for subsequent assay. CSF (20-50 µl) was collected and stored at −70° C. Portions of the peripheral neuraxis and spinal cord were removed into fixative or stored at −70° C. at autopsy for subsequent assay.

Experimental Design

Four groups of diabetic rats and 1 group of control rats were established and tested for allodynia after 1 week of hyperglycemia. Rats were implanted with an IT catheter and treatment was by both IV (tail vein) and IT injection. Rats received twice weekly treatment by each route (Mon/Thu for IT, Tues/Fri for IV) during weeks 2 and 3. Tactile allodynia was tested at the start of week 4 (3-4 days after the last treatment) and then, if tactile allodyna was present in treated rats, at 1, 3 and 6 hr after IT (Mon) and IV (Tues) treatments. Otherwise untreated diabetic rats received a single treatment with gabapentin with subsequent measurement of tactile allodynia at 1, 3 and 6 hr post-drug, to serve as a positive treatment control. At the conclusion of the study, all rats received a final injection of anti-LPA antibody (IV and/or IT route to be determined based upon tactile test data) or gabapentin at a chosen time before paw formalin injection (0.2%), with evoked flinching followed for up to 1 hour. Animals were euthanized at the end of formalin testing and tissue collected for storage as described above.

Pilot Study (Preliminary Results)

A pilot study was done in which rats were treated for 2 weeks with murine anti-LPA antibody B3 after 4 weeks of diabetes and the pain withdrawal threshold was determined. Nondiabetic mice were used as controls. In this preliminary study, the anti-LPA antibody B3 increased the paw withdrawal threshold in diabetic rats, indicating a reduction in allodynia in rats with diabetes-induced neuropathic pain. Based on these favorable results, a diabetic neuropathy prevention study was designed and conducted as described below.

Figure 3:
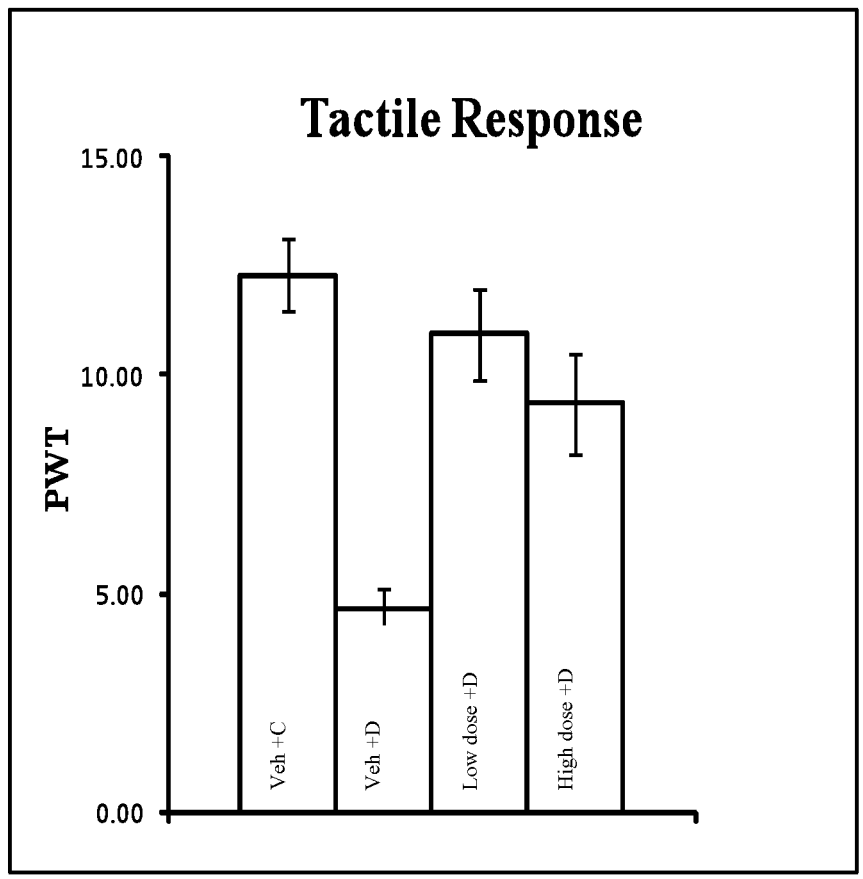
FIG. 3.

Diabetic Neuropathy Prevention Study:

To investigate the efficacy of murine antibody B3 in preventing the development of diabetic induced neuropathic pain, three groups of diabetic rats were established by treatment with STZ. Starting two weeks after the onset of diabetes, but prior to the manifestation of tactile allodynia, animals were dosed both intravenously and intrathecally to ensure antibody access to both the peripheral and central nervous system compartments, as the literature is unclear as to which or both compartments exhibit dysregulated LPA levels. The dosing regimens for the treatment groups were: two groups of test animals received 10 mg/kg of intravenously administered antibody twice a week. In addition to the intravenously administered antibody, animals received antibody twice weekly via an intrathecal catheter. One group of animals ("Low dose+D") received 2 µg antibody and one group of animals ("high dose+D") received 10 µg antibody intrathecally. One group of diabetic animals received vehicle alone ("Veh+D"). Nondiabetic rats were used as controls ("Veh+C"). The tactile response threshold was measured at the start of week 3, 4 days after the last treatment. The results are shown in FIG. 3. Anti-LPA antibody B3 increased the paw withdrawal threshold (PWT) in diabetic rats to a level similar to that observed in non-diabetic rats, indicating a marked reduction in allodynia in rats with diabetes-induced neuropathic pain.

Diabetic Neuropathy Intervention Study:

Based on encouraging results in the prevention study, the nine control diabetic rats from it were then used to assess the reversibility of the already-established diabetic-induced neuropathic pain and to discriminate between intravenous and intrathecal administration of anti-LPA antibody B3. The rats received the following treatments on different days: gabapentin (intraperitoneal) as a control agent on day 1, Lpathomab i.t. on day 3, Lpathomab i.v. on day 6 and the combination (i.t.+i.v.) on day 12. After each dosing, subsequent measurements of tactile allodynia (PWT response) at 1, 3 and 6 hr were recorded as described above for the prevention study. All animals were euthanized at the end of the study and tissues were collected and stored for further analyses.

Figure 4A:
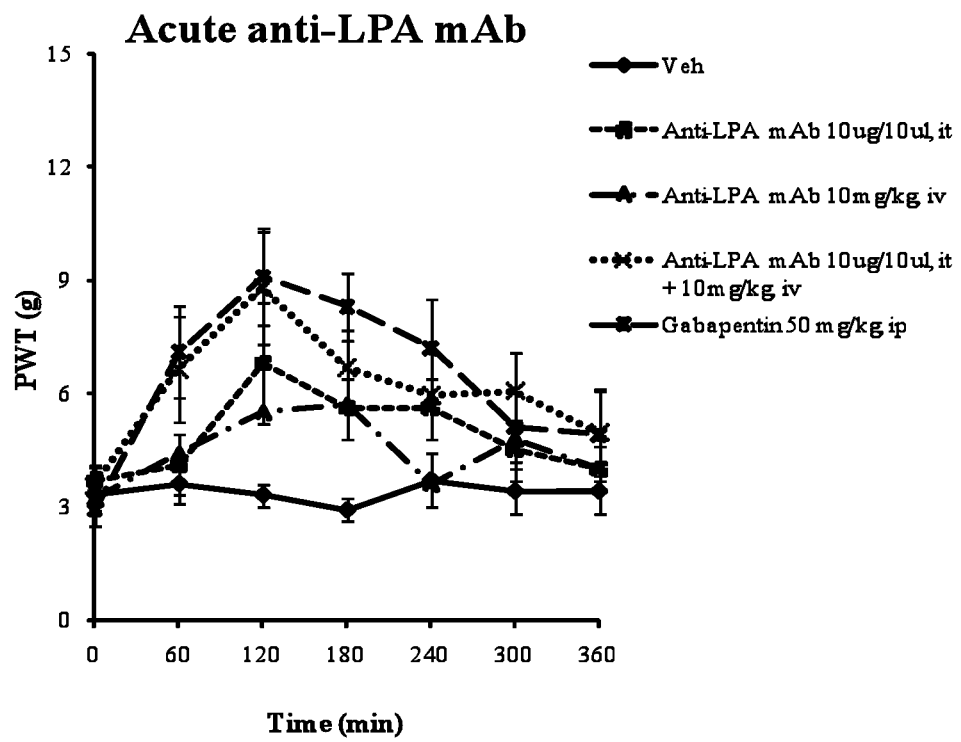
FIG. 4A is a line graph of a temporal course showing the effect of anti-LPA antibody treatment on paw withdrawal latency (PWL), a measure of pain.
Figure 4B:
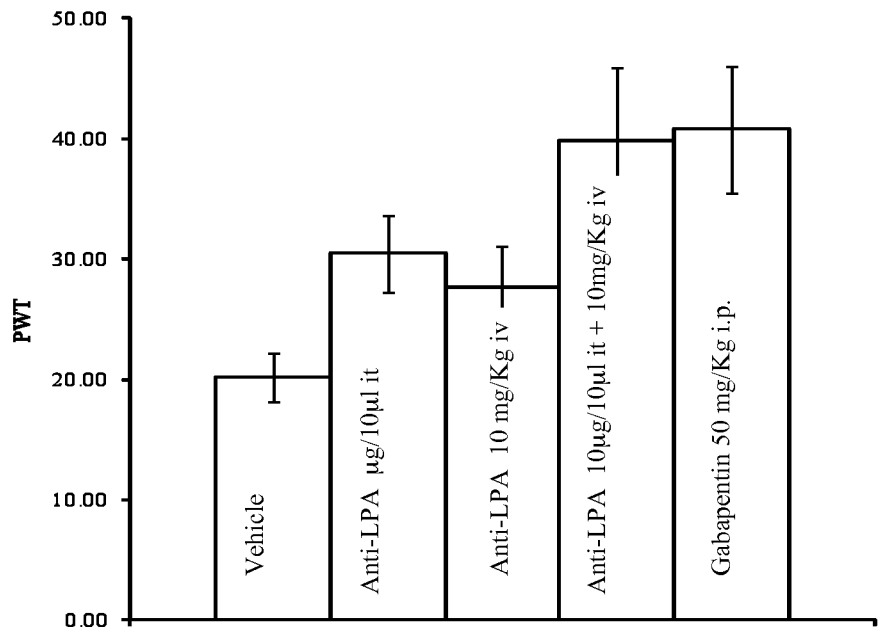
FIG. 4B is a bar graph showing area under the curve for paw withdrawal threshold. Gabapentin is used as positive control.

The results of this study are shown in FIG. 4. Both a time course graph (FIG. 4a) and an area under the curve (AUC) graph (FIG. 4b) for paw withdrawal threshold are provided. This preliminary intervention study demonstrates that a single dose of antibody was as effective as gabapentin in ameliorating established diabetic induced neuropathic pain. Both intravenous antibody administration and intrathecal administration were efficacious when compared to vehicle. Efficacy after intravenous dosing is generally considered to demonstrate involvement of peripheral nervous system mechanisms while a response seen after i.t. dosing is suggestive of central nervous system involvement. The ability of Lpathomab to mitigate pain responses from both routes of administration could suggest that LPA mediates both peripheral and central mechanisms of pain transmission. This is supported by the observed additive effect when animals were dosed with Lpathomab via both routes of administration in combination.

Example 10

Anti-LPA Antibody in Sciatic Nerve Injury Model of Neuropathic Pain

Lysophosphatidic acid (LPA) is an endogenous bioactive agent that mediates multiple cellular responses including proliferation, differentiation, angiogenesis, motility, and protection from apoptosis in a variety of cell types. LPA initiates neuropathic pain and underlying machineries through LPA1 receptor signaling in mice with partial sciatic nerve injury (Ueda at al., Nature Med, 10(7):712-8 2004). In fact, LPA1-null mice lose various nerve injury-induced neuropathic pain and its underlying mechanisms such as demyelination, down-regulation of myelin proteins and up-regulation of $Ca_v$ a2d-1 and spinal PKCg. The sciatic nerve injury-induced demyelination was observed in sciatic nerve (SCN) and dorsal root (DR), but not spinal nerve (SN), and the demyelination was abolished in DR, but not SCN in LPA1 receptor knock-out mice. When spinal slices were stimulated by substance P plus NMDA, but not by either one, there was a marked time-dependent increase in the levels of LPA, which was converted from newly produced lysophosphatidyl choline (LPC) through an action of autotaxin (Inoue, M. et al. (2008) J Neurochem, 107(6):1556-65). Thus, it is evident that intense stimulation of sensory fibers leads to LPA production, which in turn leads to a demyelination of dorsal root fibers. In addition to the sciatic nerve injury-induced model of peripheral neuropathic pain, spinal cord injury-induced central neuropathic pain and central stress-induced chronic pain models have been developed.

Anti-LPA antibody was assessed in a sciatic nerve injury-induced model of peripheral neuropathic pain (Seltzer, et al. (1990), Pain, 43(2), 205-218), and could also be assessed in models of spinal cord injury-induced central neuropathic pain and central stress-induced chronic pain. This study was conducted in the laboratory of Dr. Hiroshi Ueda at Nagasaki University.

In Vivo Studies

Six-week-old male and female C57BL/6J mice weighing 18-22 g were used. These mice were individually kept in a room maintained at 24±2° C., humidity 60±5%, and ad libitum feeding of a standard laboratory diet and tap water before use.

1) Partial Sciatic Nerve Injury (PSNI) Model

Mice were deeply anesthetized with 50 mg/kg pentobarbital. The common sciatic nerve of the right (or left) hindlimb was exposed at the level of the high thigh through a small incision, and the dorsal one half of the nerve thickness was tightly ligated with a silk suture.

2) Spinal Cord Injury (SCI) Model

Under pentobarbital (50 mg/kg) anesthesia, the dorsal surface of the dura mater is exposed after laminectomy of mice at the ninth thoracic spinal vertebrae. Spinal cord injury is produced at spinal segment of T9 using a commercially available SCI device (40 kdyn using Infinite Horizon impactor, Precision Systems & Instrumentation, Fairfax Station Va.).

3) Intermittent Cold Stress (ICS) Model

Two mice per group are kept in a cold room at 4±2° C. at 4:30 p.m. on day 1, feeding and agar instead of water. Mice are placed on a stainless steel mesh and covered with Plexiglas cage. At 10:00 a.m. the next morning, mice are transferred to the normal temperature room at 24±2° C. After they are placed at the normal temperature for 30 min, mice are put in the cold room again for 30 min. These processes are repeated until 4:30 p.m. Mice are then put in the cold room overnight. After the same treatments on the next day, mice are finally taken out from the cold room at 10:00 a.m.

Anti-LPA antibody (B3) was supplied at a minimum concentration of 0.2 μg/μL diluted in artificial cerebrospinal fluid (aCSF) comprising 125 mM NaCl, 3.8 mM KCl, 2.0 mM CaCl2, 1.0 mM MgCl2, 1.2 mM KH2PO4, 26 mM NaHCO3 and 10 mM D-glucose (pH 7.4).

1) PSNI Model

Anti-LPA Antibody Injection:

The intrathecal (i.c.v. or i.t.) injections of anti-LPA antibody were performed free hand between spinal L5 and L6 segments. The i.c.v. or i.t. injections were given in a volume of 5 μl (1 μg).

Nociception Test:

The paw pressure test was carried out using a digital von Frey apparatus test (Anesthesiometer, IITC Inc., Woodland Hills, USA). In this experiment, the threshold (in grams) of given pressure to cause the paw withdrawal behavior of mouse was evaluated. The thermal paw withdrawal test [Hargreaves, et al. (1988), Pain 32:77-88] was carried out using a thermal stimulus (IITC Inc., Woodland Hills, Calif., USA). These behavioral experiments were conducted in mice at 1, 3, 7 and 14 days postligation.

Immunohistochemistry for Protein Kinase Cγ and Caα2δ1:

After nociception test (day 14), mice are deeply anesthetized with i.p. pentobarbital and perfused transcardially with K+free PBS followed by 4% paraformaldehyde (PFA). The dorsal root ganglion (DRG) and spinal cord between L4-L5 segments is removed and post-fixed in 4% PFA. For immunostaining of isoform of protein kinase C (PKC) and Ca 2 1, the sections are then reacted with a rabbit polyclonal antibody. The sections are then incubated with a FITC-conjugated anti-rabbit IgG.

Toluidin Blue Staining and Transmission Electron Microscopy for Demyelination

DR fibers are fixed with 2.5% glutaraldehyde. The fixed DR fibers are postfixed with 2% osmium tetroxide, dehydrated in graded alcohol series, and embedded in Epon812. Thin sections (1 m) are cut from each block, stained with alkaline Toluidine blue, and examined by light microscopy. Ultrathin sections (80 nm thick) are cut with an Ultracut S (Leica, Austria), and then stained with uranyl acetate and Lead citrate, respectively. The stained sections are observed under an electron microscope (JEM-1200EX; JEOL, Tokyo, Japan).

2) SCI Model

Anti-LPA Antibody Injection:

The intracerebroventricular (i.c.v. or i.t.) injections of anti-LPA antibody are carried out into the right lateral ventricle of mice. The i.c.v. or i.t. injections are given in a volume of 5 µl (1 µg) 1-5 times.

Nociception Test:

The paw pressure test and thermal paw withdrawal test are carried out at 2, 4, 8 and 12 weeks after SCI.

3) ICS Model

Anti-LPA Antibody Injection:

The i.c.v. or i.t. injections of anti-LPA antibody are given in a volume of 5 µl (1 µg) 1-5 times.

Nociception Test:

The paw pressure test and thermal paw withdrawal test are carried out at 1, 3, 5, 12, and 19 days after ICS.

The results of a preliminary PSNI experiment are shown in FIG. 5.

1. Prophylactic experiment (FIG. 5A): Mice were injected with antibody to LPA (B3) (1 ug, intrathecally) one hour before partial sciatic nerve injury, which induces peripheral neuropathic pain [Seltzer, et al. (1990), Pain, 43(2), 205-218]. The injury was performed on only one hindlimb per animal, and pain responses were measured on the injured (ipsilateral) and uninjured (contralateral) sides. The thermal paw withdrawal latency (PWL) test (Hargreaves, et al., 1988) was used to quantitate the pain response. Briefly, a thermal beam was focused on the hind limb foot pads of mice placed on a glass surface and the withdrawal response latency was measured (in seconds). Thus, a higher (longer time) response indicates less pain and a lower (shorter time) response indicates more pain.

Figure 5A:
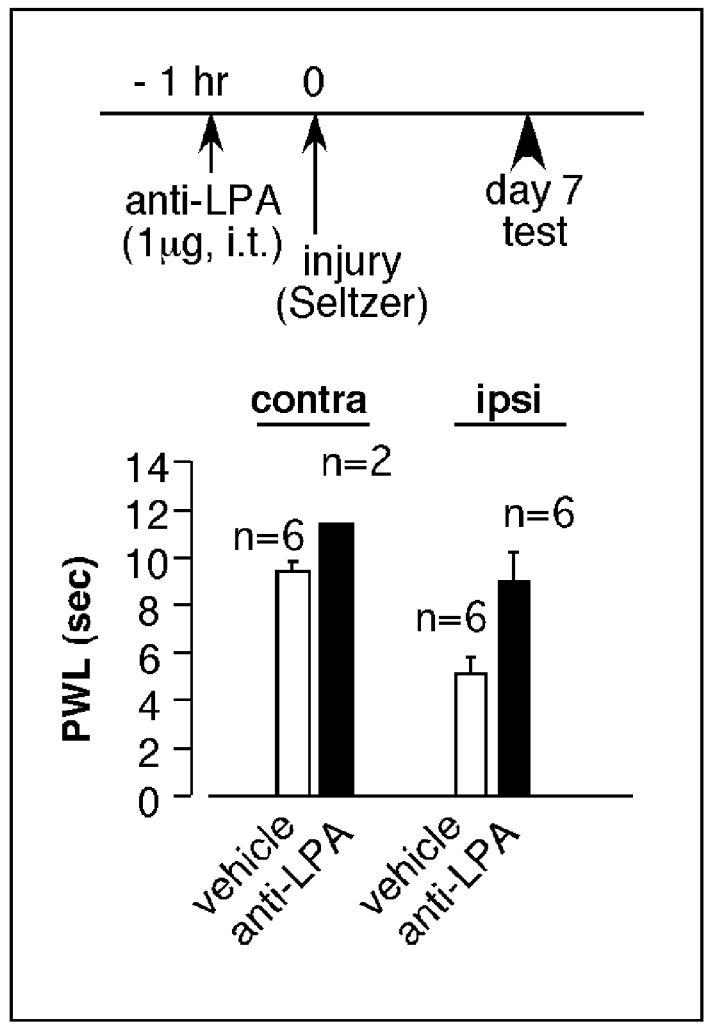
FIG. 5A is a time line showing the effect of prophylactic anti-LPA antibody treatment on paw withdrawal latency (PWL), a measure of pain.

FIG. 5A shows that the partial sciatic nerve injury causes a dramatically increased pain response (shortened PWL times) on the injured side ("ipsi") compared to the uninjured side ("contra") in the absence of antibody treatment (comparison of the white bars). This effect is prevented by treatment with anti-LPA antibody (B3) (black bars).

Figure 5B:
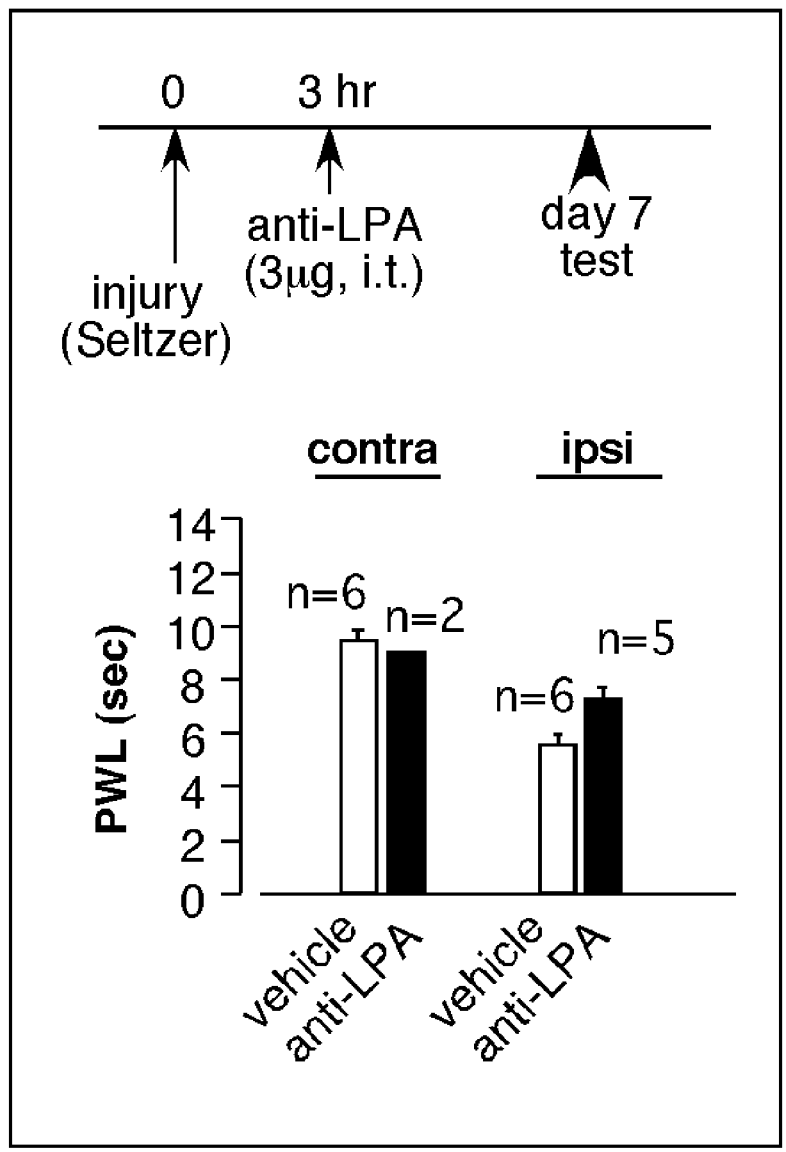
FIG. 5B is a bar graph showing the effect of interventional anti-LPA antibody treatment on PWL. Both the prophylactic and interventional treatments decreased pain in this model.

2. Interventional experiment (FIG. 5B): Mice were injected with antibody to LPA (B3) (3 ug, intrathecally) three hours after partial sciatic nerve injury (ibid.). FIG. 5B shows that, as above, the partial sciatic nerve injury causes a dramatically increased pain response (shortened PWL times) on the injured side ("ipsi") compared to the uninjured side ("contra") in the absence of antibody treatment (comparison of the white bars). This effect is at least partially reversed by treatment post-injury with anti-LPA antibody (B3) (black bars).

These experiments validate LPA as a target for nerve-injury induced neuropathic pain, and suggest that inhibitors of LPA such as antibodies that reduce the effective concentration of LPA are therapeutically useful in relief of neuropathic pain.

Figure 6A:
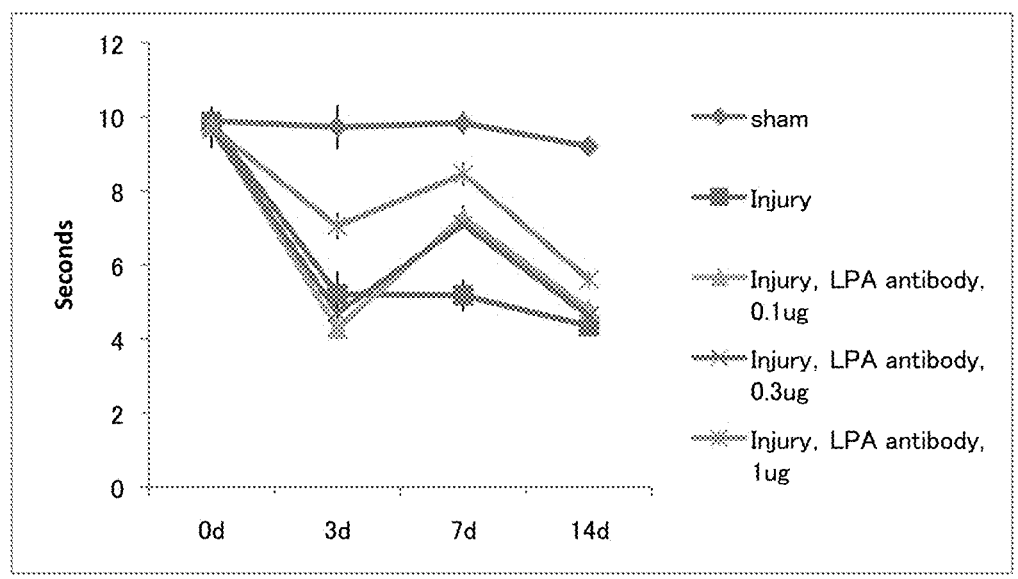
FIG. 6a shows the effect of three doses of anti-LPA antibody on thermal pain withdrawal (Hargreaves assay) over 14 days.
Figure 6B:
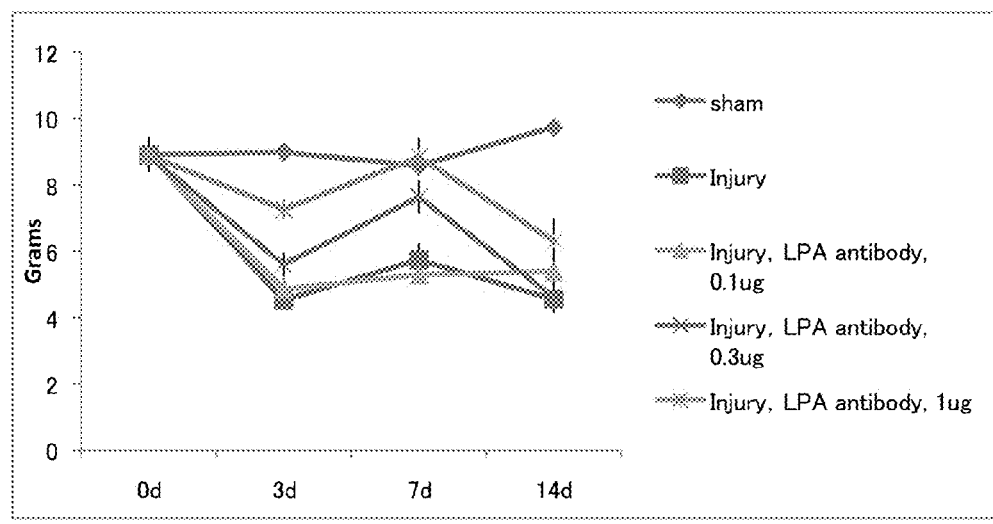
FIG. 6b shows the effect of three doses of anti-LPA antibody on paw pressure over 14 days.

In a follow-on time course experiment, mice were deeply anesthetized with 50 mg/kg pentobarbital. The common sciatic nerve of the right (or left) hind limb was exposed at the level of the high thigh through a small incision, and the dorsal one half of the nerve thickness was tightly ligated with a silk suture. The intrathecal (i.t.) injections of anti-LPA antibody were given one hour before injury, and were performed free hand between spinal L5 and L6 segments. The i.t. injections were given in a volume of 5 µl. The thermal paw withdrawal (Hargreaves) and paw pressure tests for nociception behavior was carried out up to 14 days post-ligation. Lpathomab was found to reduce neuropathic pain for a week or more in sciatic nerve injury-induced peripheral neuropathy (FIG. 6).

Example 11

Effect of Anti-LPA Antibody in a Rat Model of Adjuvant-Induced Arthritis (AIA)

Inflammation was established in female Lewis rate (150-200 g). 10 animals per dose group were injected subcutaneously in the tail with 3 mg of heat-killed *Mycobacterium buytricum* suspended in paraffin oil (3 mg/0.150 ml) on day 0. Control animals were injected with paraffin oil only. Rats were assigned numbers and body weights were followed each week. By day 9-10 rats manifested signs of disease and baselines were taken by measuring paw edema (volume) with a plethysmometer. In diseased rats a paw volume of 0.200 ml greater than paw volume in control rats (1.2 ml) was required for inclusion in the study. Animals were randomized based on paw edema and then received vehicle, isotype control, or humanized anti-LPA antibody LT3015. Paw volume was measured seven days and eleven days after antibody dosing. $ED_{50}$ and $ED_{80}$ data were calculated based on the data from eleven days following dosing. Vocalization as a measurement of pain was evaluated in the study rats on the final day of the study. Terminal blood collection was performed. Plasma samples were analyzed for antibody concentration. Plasma and paw fluid samples were analyzed for cytokines, eicosanoids, or other inflammatory mediators of interest. Paws were collected at termination for possible histological evaluation.

Dosing: Dosing began once disease manifested, approximately d11-25. Dosing was every 3 days, intraperitoneally, for approximately 5 doses.

Groups: 4 groups=32 rats total, as follows:
1. Negative Control—paraffin oil only—Vehicle
2. Positive Control—Naproxen 10 mg/kg daily, by mouth
3. Isotype Control—40 mg/kg unrelated antibody every 3 days
4. Anti-LPA antibody LT3015—40 mg/kg every 3 days
5. Anti-LPA antibody LT3015—8 mg/kg every 3 days
6. Anti-LPA antibody LT3015—1.6 mg/kg every 3 days.

Figure 7:
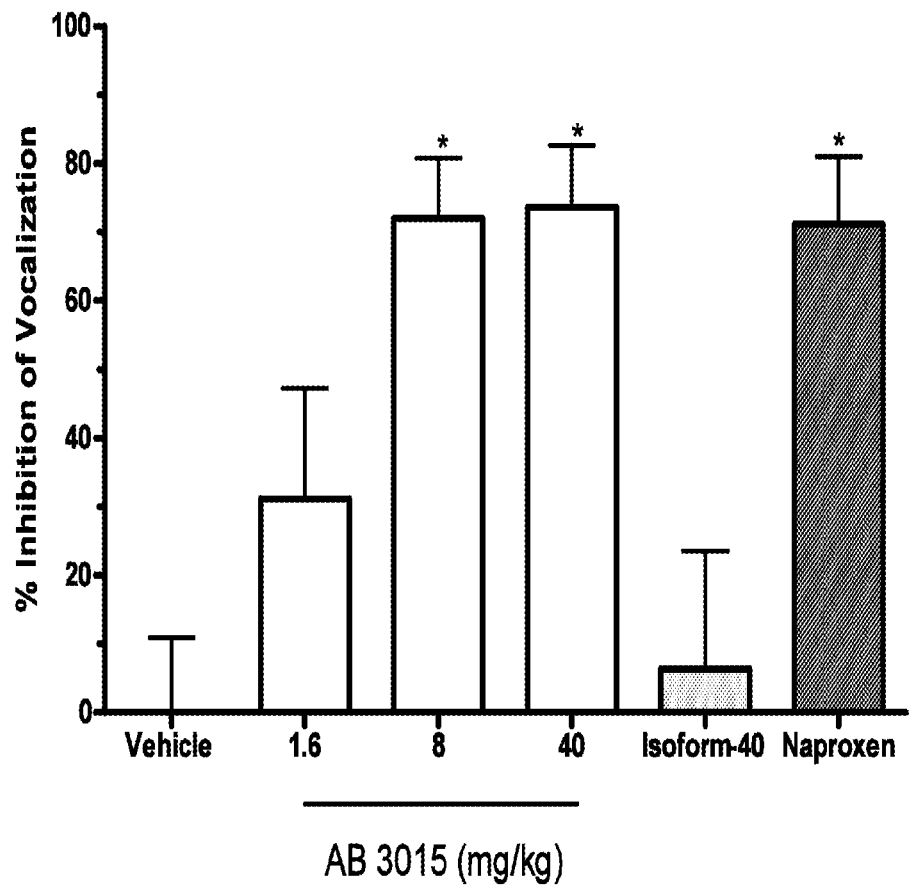
FIG. 7.

In this study, treatment with humanized anti-LPA antibody (LT3015) was found to reverse the pain vocalization response in the rat AIA model of arthritis. This is shown in FIG. 7. The bars indicate reduction in vocalization. Vehicle alone and isoform control did not decrease vocalization; while the medium (8 mg/kg) and high (40 mg/kg) doses of anti-LPA antibody reduced vocalization by 70-75%, as did the positive control, Naproxen. The low dose (1.6 mg/kg) of LT3015 reduced vocalizations by approximately 30%, showing a dose dependent effect.

Example 12

Evaluation of Anti-LPA Antibody in Paclitaxel-Induced Neuropathic Pain

Neuropathic pain is a problematic and often dose-limiting side effect of paclitaxel (TAXOL) treatment for cancer. The role of LPA in paclitaxel-induced neuropathic pain, and the ability of the anti-LPA antibody B3 to mitigate this pain, was evaluated. This study was conducted in the laboratory of Dr Daniela Salvemini, St. Louis University School of Medicine.
Material and Methods:
Experimental Animals:

Male Sprague Dawley rats (200-210 g starting weight) from Harlan (Indianapolis, Ind.) were housed 3-4 per cage in a controlled environment (12 h light/dark cycle) with food and water available ad libitum. All experiments were performed in accordance with the International Association for the Study of Pain and the National Institutes of Health guidelines on laboratory animal welfare and the recommendations by Saint Louis University Institutional Animal Care and Use Committee. All experiments were conducted with the experimenters blinded to treatment conditions.
Paclitaxel-Induced Neuropathic Pain and Drug Administration:

This is a well characterized rat model developed by Bennett in which repeated intraperitoneal (i.p) injections of low doses of paclitaxel induce neuropathic pain (mechano-allodynia) with little systemic toxicity or motor impairment. The behavioral responses last for several weeks to months, thus modeling painful neuropathies in patients. Flatters, S. J. & Bennett, G. J. (2006). Pain 122, 245-257; Jin, H. W., et al. (2008) Exp Neurol 210, 229-237; Polomano, R. C., et al. (2001) Pain 94, 293-304. Paclitaxel or its vehicle (Cremophor EL and 95% dehydrated ethanol in 1:1 ratio) was injected i.p in rats on four alternate days that is day (D) 0, 2, 4 and 6 at 1 mg/kg on with a final cumulative dose of 4 mg/kg. 1-3 The following experimental test substances were used: the murine anti-LPA antibody B3 and an isotype control antibody, LT1015; these were dissolved in saline and provided by Lpath in individual vials. Experimental test substances were given intravenously (i.v) at 25 mg/kg according to a dosing regimen designed by Lpath as follows (and see experimental design, schematic in power point format). Experimental test substances were given one day before (D-1) the first injection of paclitaxel, and subsequently on D2, D5, D8, D11 and D14 after the first injection of paclitaxel. Vehicle that was used to dissolve test substance (saline) was injected according to the same dosing paradigm in paclitaxel-treated group or its respective vehicle. If injections of experimental test substances coincided with the injection of paclitaxel (i.e. D2), experimental test substances were delivered 15 min before paclitaxel. Mechanical withdrawal thresholds were assessed with an electronic version of the von Frey test (dynamic plantar aesthesiometer, model 37450; Ugo Basile, Milan, Italy) on D-1 before experimental test substance injection, the day after (D0) and before the first i.p. injection of paclitaxel and subsequently on D12 and D16. To this end, each rat was placed in a Plexiglas chamber (28×40×35-cm, wire mesh floor) and allowed to acclimate for fifteen minutes. After acclimation, a servo-controlled mechanical stimulus (a pointed metallic filament) was applied to the plantar surface, which exerts a progressively increasing punctate pressure, reaching up to 50 g within 10 s. The pressure evoking a clear voluntary hind-paw withdrawal response was recorded automatically and taken as the mechanical threshold index. Mechanical threshold was assessed three times at each time point to yield a mean value, which is reported as mean absolute threshold (grams, g). The development of mechano-allodynia was evidenced by a significant (P<0.05) reduction in mechanical mean absolute paw-withdrawal thresholds (grams, g) at forces that failed to elicit withdrawal responses before paclitaxel treatment (baseline). Because paclitaxel treatment results in bilateral allodynia and thresholds did not differ between left and right hind paws at any time point in any group, values from both paws were averaged for further analysis and data presentation. A total of four groups were used with n=3 rats/group.
Group 1: Vehicle instead of paclitaxel+saline
Group 2: Paclitaxel+saline
Group 3: Paclitaxel+504B3
Group 4: Paclitaxel+LT1015

Figure 8:
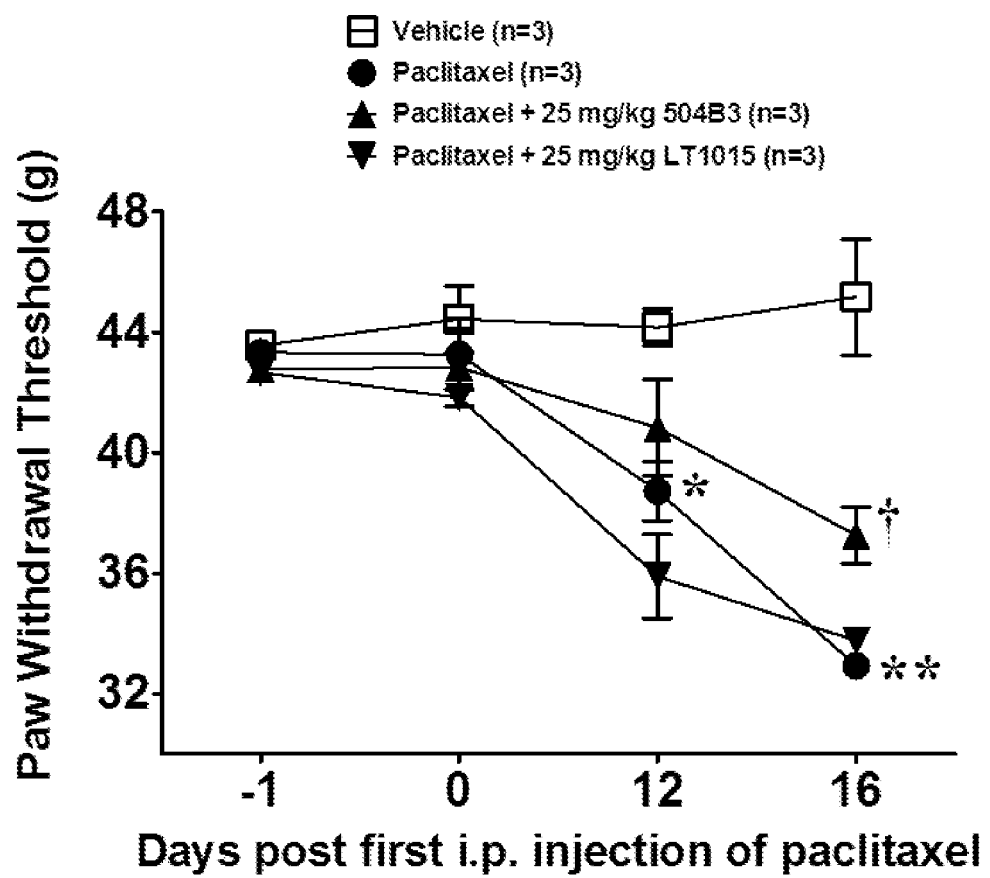
FIG. 8.

Paw withdrawal threshold (g) on (D-1) and before i.v injection of experimental test substances or their vehicle (saline) were (mean+/s.em): 43.6±0.296, 43.3±0.376, 42.8±0.120 and 42.7±0.203, respectively.
Statistical Analysis:

Data are expressed as mean±SEM for 3 animals per group and analyzed by two-tailed, two-way ANOVA with Bonferroni post hoc comparisons to the paclitaxel group. *P<0.05, **P<0.001 paclitaxel vs. vehicle group.
Results Effects of anti-LPA antibody B3 and control antibody on paclitaxel-induced neuropathic pain: When compared to the vehicle treated group, administration of paclitaxel led to the development of mechano-allodynia (FIG. 8). The development of mechano-allodynia at 16 h was significantly attenuated by anti-LPA antibody B3, but not by isotype control LT1015 (FIG. 8).

All of the compositions and methods described and claimed herein can be made and executed without undue experimentation in light of the present disclosure. While the compositions and methods of this invention have been described in terms of preferred embodiments, it will be apparent to those of skill in the art that variations may be applied to the compositions and methods. All such similar substitutes and modifications apparent to those skilled in the art are deemed to be within the spirit and scope of the invention as defined by the appended claims.

All patents, patent applications, and publications mentioned in the specification are indicative of the levels of those of ordinary skill in the art to which the invention pertains. All patents, patent applications, and publications, including those to which priority or another benefit is claimed, are herein incorporated by reference to the same extent as if each individual publication was specifically and individually indicated to be incorporated by reference.

The invention illustratively described herein suitably may be practiced in the absence of any element(s) not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A method of reducing neuropathic pain or pain associated with chemotherapy, comprising administering to a subject having neuropathic pain or pain associated with chemotherapy, an antibody or antibody fragment that binds and neutralizes lysophosphatidic acid, thereby reducing said neuropathic pain or pain associated with chemotherapy.

2. A method according to claim 1 wherein the antibody or antibody fragment is a monoclonal antibody or monoclonal antibody fragment.

3. A method according to claim 2 wherein the antibody or antibody fragment is a humanized monoclonal antibody or antibody fragment of a humanized monoclonal antibody.

4. A method according to claim 1 wherein the subject is a human subject.

* * * * *